United States Patent
Kottas et al.

(10) Patent No.: US 9,184,397 B2
(45) Date of Patent: *Nov. 10, 2015

(54) HETEROLEPTIC IRIDIUM COMPLEXES AS DOPANTS

(71) Applicant: Universal Display Corporation, Ewing, NJ (US)

(72) Inventors: Gregg Kottas, Ewing, NJ (US); Nasrin Ansari, Monmouth Jct., NJ (US); Zeinab Elshenawy, Holland, PA (US); Alan DeAngelis, Pennington, NJ (US); Chuanjun Xia, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/156,808

(22) Filed: Jan. 16, 2014

(65) Prior Publication Data

US 2014/0159028 A1    Jun. 12, 2014

Related U.S. Application Data

(63) Continuation of application No. 13/193,221, filed on Jul. 28, 2011, now Pat. No. 8,709,615, and a continuation-in-part of application No. 12/727,615, filed on Mar. 19, 2010, now Pat. No. 8,722,205.

(60) Provisional application No. 61/162,746, filed on Mar. 23, 2009.

(51) Int. Cl.
*H01L 51/54* (2006.01)
*C09K 11/06* (2006.01)
(Continued)

(52) U.S. Cl.
CPC ........ *H01L 51/0085* (2013.01); *C07F 15/0033* (2013.01); *C09K 11/06* (2013.01); *H01L 51/50* (2013.01); *H05B 33/14* (2013.01); *C09K 2211/1007* (2013.01); *C09K 2211/1029* (2013.01); *C09K 2211/1088* (2013.01); *C09K 2211/185* (2013.01); *H01L 51/0054* (2013.01); *H01L 51/0074* (2013.01); *H01L 51/5016* (2013.01)

(58) Field of Classification Search
None
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| CN | 1680366 | 10/2005 |
| EP | 0650955 | 5/1995 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Marie R. Yamnitzky
(74) *Attorney, Agent, or Firm* — Duane Morris LLP

(57) ABSTRACT

Novel phosphorescent heteroleptic iridium complexes with phenylpyridine and dibenzo-containing ligands are provided. Alkyl substitution at specific positions on the ligands gives rise to compounds with improved OLED properties, including saturated green emission.

22 Claims, 3 Drawing Sheets

Formula I

(51) Int. Cl.
*H01L 51/00* (2006.01)
*H05B 33/14* (2006.01)
*C07F 15/00* (2006.01)
*H01L 51/50* (2006.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,893,743 B2 | 5/2005 | Sato et al. |
| 6,921,915 B2 | 7/2005 | Takiguchi et al. |
| 6,953,628 B2 | 10/2005 | Kamatani et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,635,526 B2 | 12/2009 | Stossel et al. |
| 7,955,716 B2 | 6/2011 | Nomura et al. |
| 8,709,615 B2 * | 4/2014 | Kottas et al. ............... 428/690 |
| 8,722,205 B2 * | 5/2014 | Xia et al. ............... 428/690 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0013905 A1 | 1/2004 | Tsuboyama et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2006/0287498 A1 | 12/2006 | Morishita et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0244004 A1 | 9/2010 | Xia et al. |

FOREIGN PATENT DOCUMENTS

| | | |
|---|---|---|
| EP | 01238981 | 9/2002 |
| EP | 1349435 | 10/2003 |
| EP | 1725079 | 11/2006 |
| EP | 1820801 | 8/2007 |
| EP | 2034538 | 3/2009 |
| JP | 200511610 | 1/2005 |
| JP | 2005029782 | 2/2005 |
| JP | 2006179895 | 7/2006 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2004111066 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009030981 | 3/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

(56) References Cited

OTHER PUBLICATIONS

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3, (2007).

Baldo et al. "Highly Efficient Phosphorescent Emission from Organic Electroluminescent Devices" Nature, vol. 395, 151-154, (1998).

Baldo et al. "Very high-efficiency green organic light-emitting devices based on electrophosphorescence" Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1:15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III)Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., "1,2,4-Triazole Derivative as an Electron Transport Layer in Organic Electroluminescent Devices," Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7)1 704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91:209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Llght-Emitting Diodes with Phosphorescent Platinum Complexes Containing NΛCΛN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177, (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl, Phys. Lett., 51(12):913-915 (1987).

Tung, Yung-Liang et al., "Organic Light-Emitting Diodes Based on Charge-Neutral Ru II PHosphorescent Emitters " Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., "A Novel Class of Phosphorescent Gold(III) Alkynyl-Based Organic Light-Emitting Devices with Tunable Colour," Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

Formula I

HETEROLEPTIC IRIDIUM COMPLEXES AS DOPANTS

CROSS-REFERENCE TO RELATED APPLICATIONS

This application is a continuation of U.S. patent application Ser. No. 13/193,221 filed Jul. 28, 2011, now U.S. Pat. No. 8,709,615, and a continuation-in-part of U.S. patent application Ser. No. 12/727,615, filed Mar. 19, 2010, now U.S. Pat. No. 8,722,205, which claims priority to U.S. Provisional Application No. 61/162,476, filed Mar. 23, 2009, the entire contents of which are incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to heteroleptic iridium complexes suitable for inclusion in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

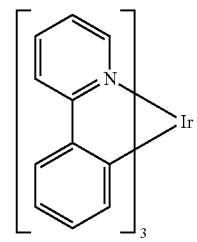

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect, a compound having the formula:

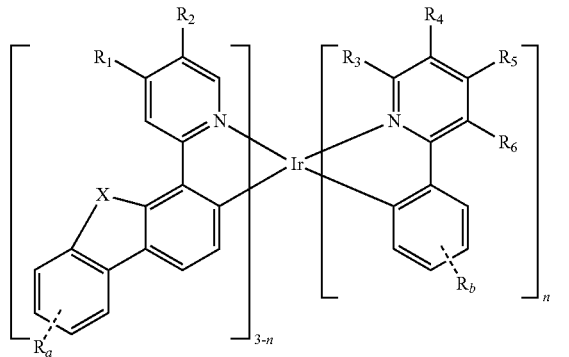

Formula I is provided. $R_1$ and $R_2$ are optionally linked and the sum of the number of carbon atoms in $R_1$ and $R_2$ is at least 2. $R_3$, $R_4$, $R_5$, $R_6$ are optionally linked, and $R_a$ and $R_b$ represent mono-, di-, tri- or tetra-substitution. X is selected from the group consisting of BR, NR, PR, O, S, Se, C=O, S=O, SO$_2$, CRR', SiRR', and GeRR', and $R_a$, $R_b$, R, R', $R_1$, $R_2$, $R_3$, $R_4$, $R_5$, and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2.

In one aspect, n is 2. In one aspect, X is O. In one aspect, $R_1$ is hydrogen and $R_2$ is alkyl. In another aspect, $R_1$ is alkyl and $R_2$ is hydrogen. In one aspect, $R_1$ and $R_2$ are alkyl. In one aspect, $R_1$ and $R_2$ contain one or more deuterium atoms. In another aspect, $R_1$ or $R_2$ are independently selected from the group consisting of branched alkyl, cyclic alkyl, bicyclic alkyl, and multicyclic alkyl. In one aspect, $R_1$ or $R_2$ is isopropyl.

In one aspect, $R_1$ or $R_2$ contain one or more deuterium atoms. In one aspect, $R_3$, $R_4$, $R_5$ and $R_6$ are independently selected from the group consisting of hydrogen, deuterium, alkyl, aryl, and combinations thereof. In another aspect, at least one of $R_3$, $R_4$, $R_5$ and $R_6$ comprises a branched alkyl, cyclic alkyl, bicyclic alkyl, or a multicyclic alkyl. In one aspect, $R_3$, $R_4$, $R_5$ or $R_6$ contain one or more deuterium atoms.

In one aspect, the compound is selected from the group consisting of Compound 53, Compounds 157-159, Compound 165, Compound 174, Compound 175, Compounds 184-185, Compound 314, Compound 321, Compounds 625-628, Compound 633, Compound 643, Compounds 652-653, and Compounds 1145-1146.

In one aspect, a first device is provided. The first device comprises a first organic light-emitting device, further comprising an anode, a cathode, and an organic layer, disposed between the anode and the cathode, comprising a compound having the formula:

Formula I $R_1$ and $R_2$ are optionally linked and the sum of the number of carbon atoms in $R_1$ and $R_2$ is at least 2. $R_3$, $R_4$, $R_5$, $R_6$ are optionally linked, and $R_a$ and $R_b$ represent mono-, di-, tri- or tetra-substitution. X is selected from the group consisting of BR, NR, PR, O, S, Se, C=O, S=O, SO$_2$, CRR', SiRR', and GeRR', and $R_a$, $R_b$, R, R', $R_1$, $R_2$, $R_3$, $R_4$, $R_5$, and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2.

In one aspect, the first device is a consumer product. In another aspect, the first device is an organic light-emitting device. In another aspect, the first device comprises a lighting panel. In one aspect, the organic layer is an emissive layer and the compound is an emissive dopant. In another aspect, the organic layer is an emissive layer and the compound is a non-emissive dopant.

In one aspect, the organic layer further comprises a host. In another aspect, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $C\equiv CC_nH_{2n+1}$, $Ar_1$, $Ar_1$—$Ar_2$, $C_nH_{2n}$—$Ar_1$, or no substitution, wherein $Ar_1$ and $Ar_2$ are independently selected from the group consisting of benzene, biphenyl, naphthalene, triphenylene, carbazole, and heteroaromatic analogs thereof, and wherein n is from 1 to 10.

In one aspect, the host has the formula

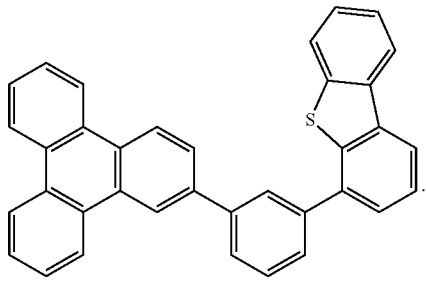 [SMILES: c1cc(-c2ccc3c4ccccc4c4ccccc4c3c2)cc(-c2cccc3c2sc2ccccc23)c1]

In another aspect, the host is selected from the group consisting of:

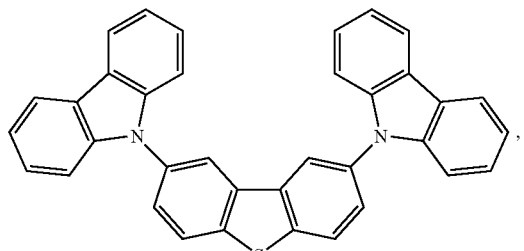

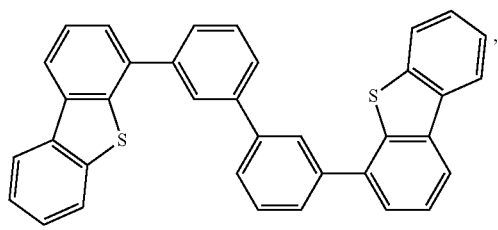

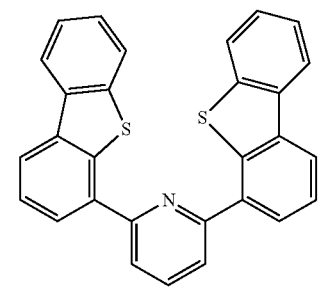

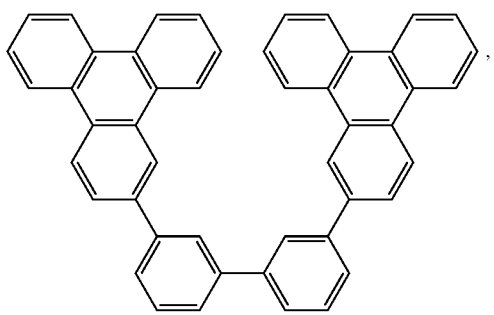

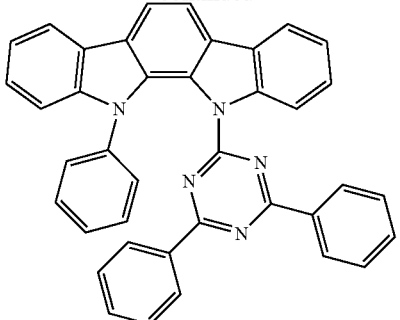

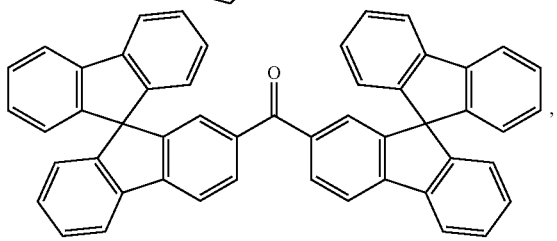

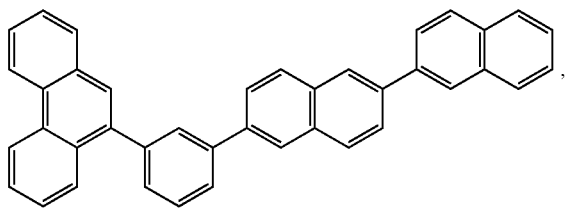 [SMILES: c1cc(-c2ccc3cc(-c4ccc5ccccc5c4)ccc3c2)cc(-c2cc3ccccc3c3ccccc23)c1]

and combinations thereof.

In one aspect, the host is a metal complex.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
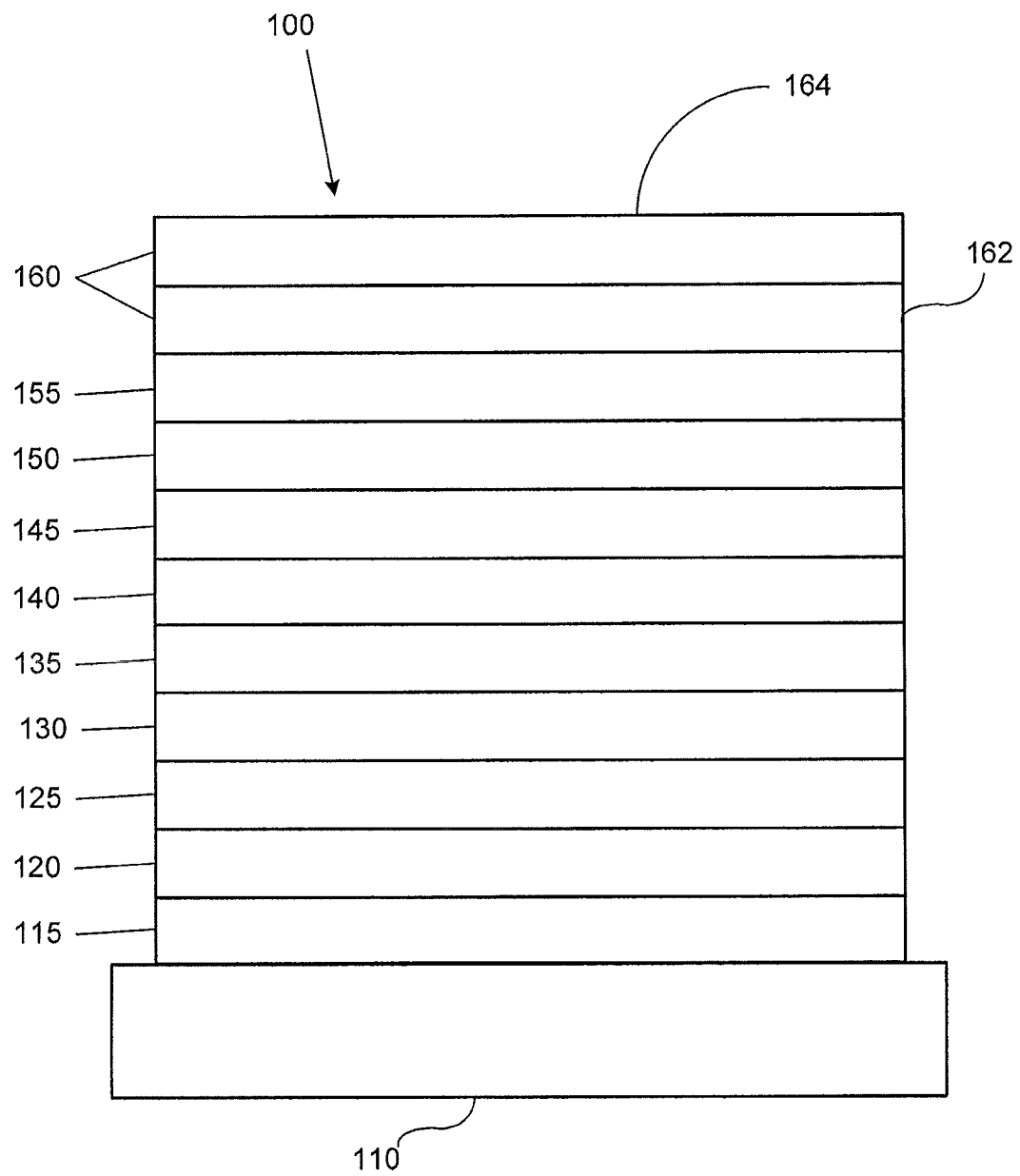
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
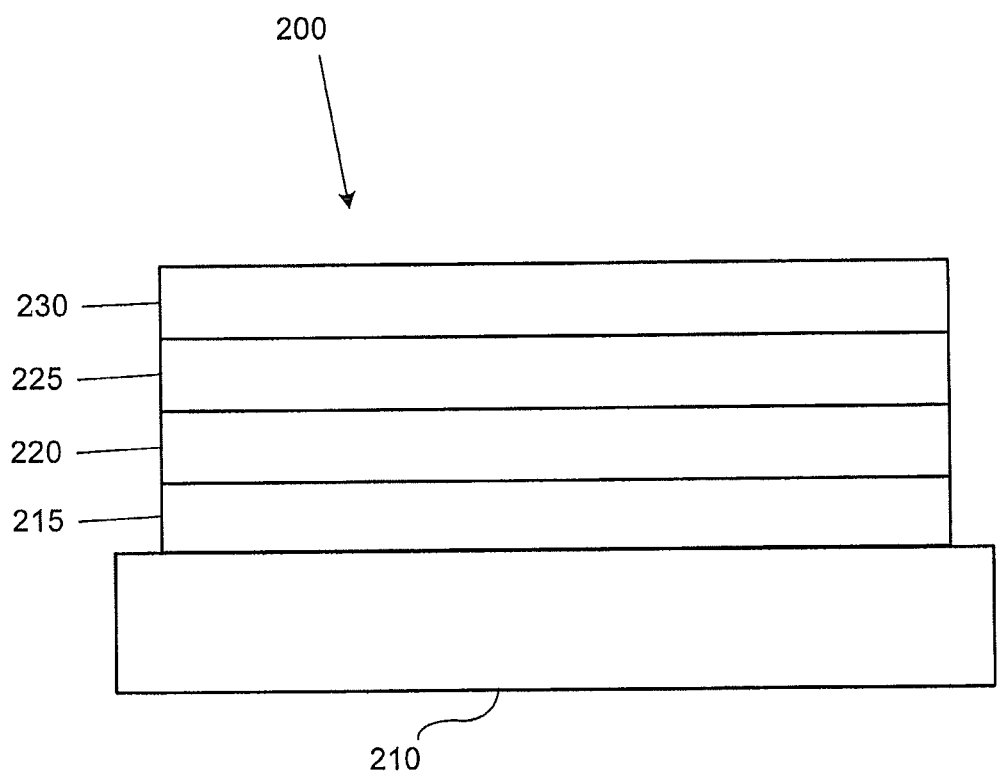
FIG. 2 shows an inverted organic light-emitting device that does not have a separate electron transport layer.
Figure 3:
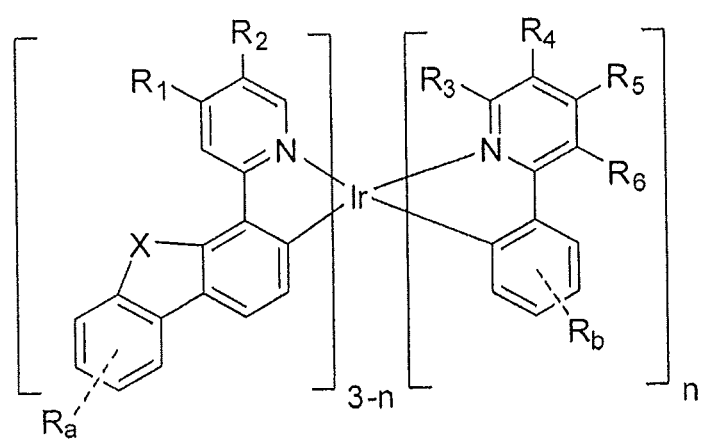
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment, a compound having the formula:

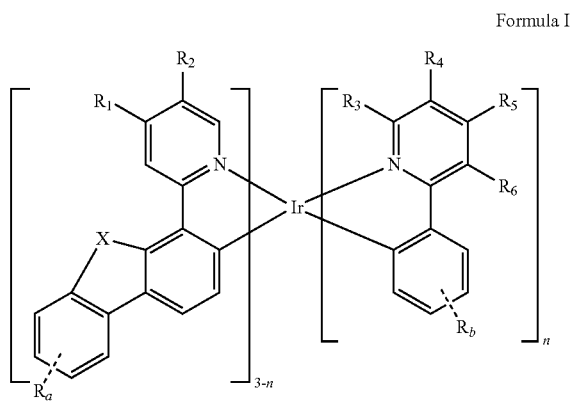

Formula I is provided. $R_1$ and $R_2$ are optionally linked and the sum of the number of carbon atoms in $R_1$ and $R_2$ is at least 2. Thus, both $R_1$ and $R_2$ both represent a substituent with at least one carbon. If $R_1$ does not represent substituent containing carbon, then $R_2$ must represent a substituent containing at least two carbons and vice versa. $R_3$, $R_4$, $R_5$, $R_6$ are optionally linked, and $R_a$ and $R_b$ represent mono-, di-, tri- or tetra-substitution. X is selected from the group consisting of BR, NR, PR, O, S, Se, C=O, S=O, SO$_2$, CRR', SiRR', and GeRR', and $R_a$, $R_b$, R, R', $R_1$, $R_2$, $R_3$, $R_4$, $R_5$, and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2.

In one embodiment, n is 2. In one embodiment, X is O. In one embodiment, $R_1$ is hydrogen and $R_2$ is alkyl. In another embodiment, $R_1$ is alkyl and $R_2$ is hydrogen. In one embodiment, $R_1$ and $R_2$ are alkyl. In another embodiment, $R_1$ or $R_2$ are independently selected from the group consisting of branched alkyl, cyclic alkyl, bicyclic alkyl, and multicyclic alkyl. In one embodiment, $R_1$ or $R_2$ is iso-propyl. Substitution at the 4- and 5-positions of either pyridine ring in the compounds of Formula I can give rise to compounds with desirable properties such as saturated green emission, high efficiencies, and long device lifetimes when incorporated in OLED devices. The photophysical and device properties of devices incorporating these compounds may be tuned by varying the nature of the substituent at the 4- or 5-position on the pyridine. The 4-position on a pyridine ring in the compound of Formula I is the position occupied by the $R_5$ or $R_1$ substituent, whereas the 5-position is the position occupied by the $R_4$ or $R_2$ substituent.

As used herein, fragments containing the following structure:

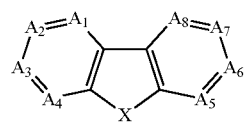

are called DBX groups, i.e. dibenzo X, where X is any of the atoms or groups described herein. Atoms A1-A8 can comprise nitrogen or carbon.

In one embodiment, $R_1$ or $R_2$ contain one or more deuterium atoms. In one embodiment, $R_1$ and $R_2$ contain one or more deuterium atoms. In one embodiment, $R_3$, $R_4$, $R_5$ and $R_6$ are independently selected from the group consisting of hydrogen, deuterium, alkyl, aryl, and combinations thereof. In another embodiment, at least one of $R_3$, $R_4$, $R_5$ and $R_6$ comprises a branched alkyl, cyclic alkyl, bicyclic alkyl, or a multicyclic alkyl. In one embodiment, $R_3$, $R_4$, $R_5$ or $R_6$ contain one or more deuterium atoms. Without being bound by theory, incorporation of deuterium is thought to improve stability of compounds due the greater bond strength of the carbon-deuterium (C-D) bond versus the carbon-hydrogen (C—H) bond. Therefore, compounds wherein labile C—H bonds are replaced by C-D bonds, higher stability can be expected. Without being bound by theory, it is believed that incorporation of deuterium atoms on the alkyl groups of ligands for iridium complexes, the resulting complexes can have longer device lifetimes.

In one embodiment, the compound is selected from the group consisting of:

Compound 53

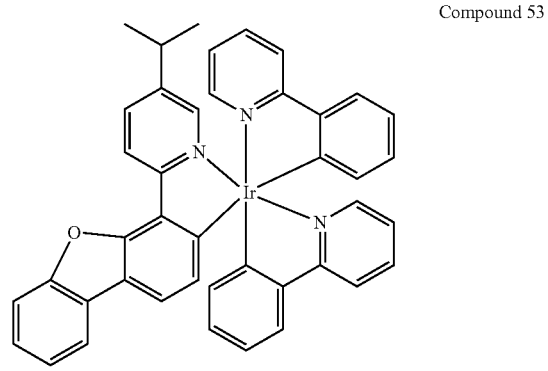

Compound 157
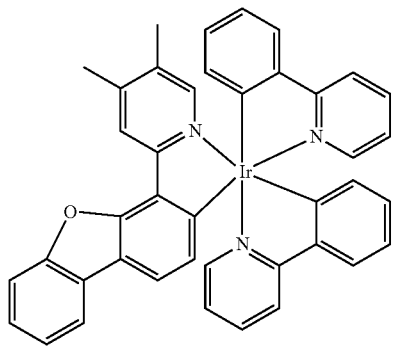
Compound 158
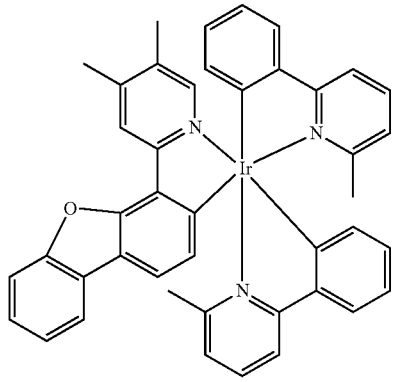
Compound 159
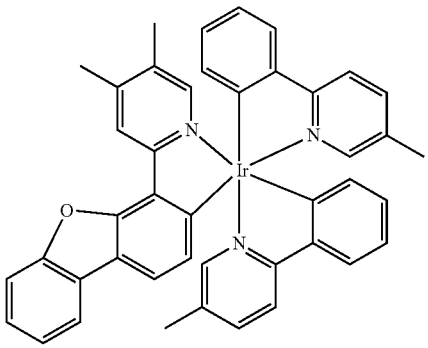
Compound 165
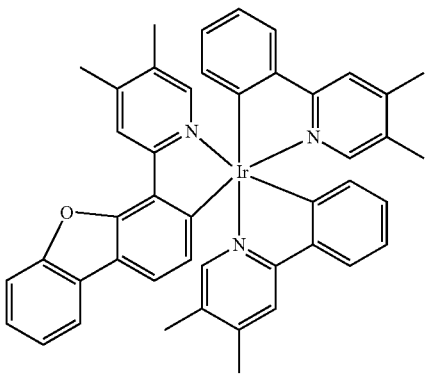
Compound 174
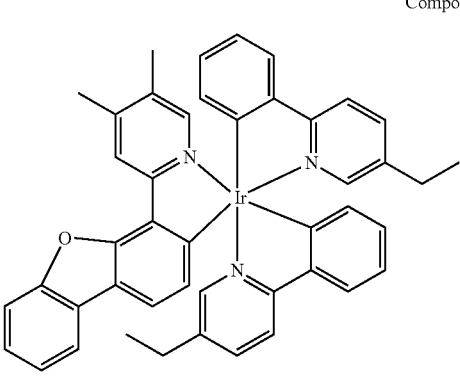
Compound 175
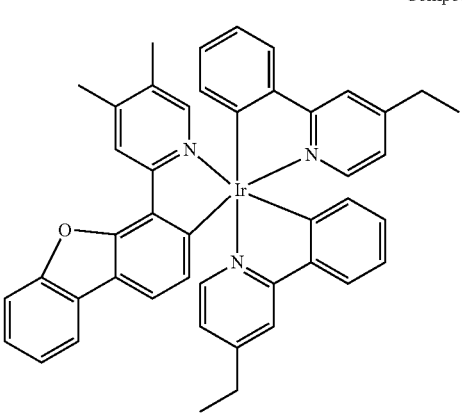
Compound 184
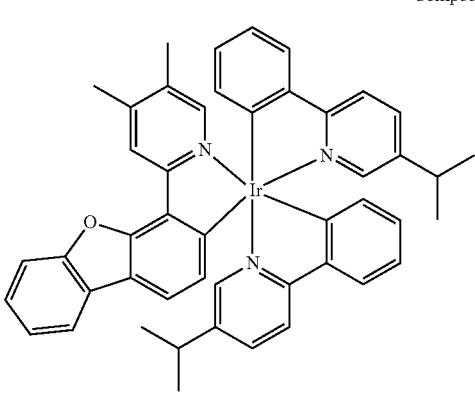
Compound 185
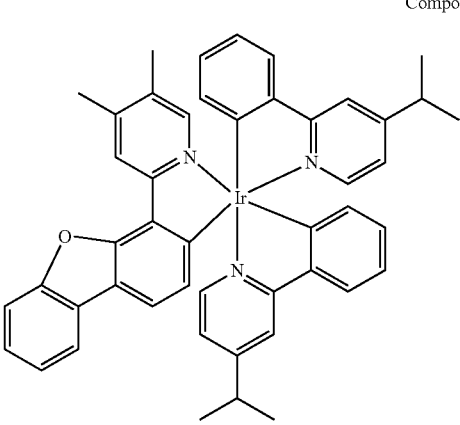

-continued
Compound 314
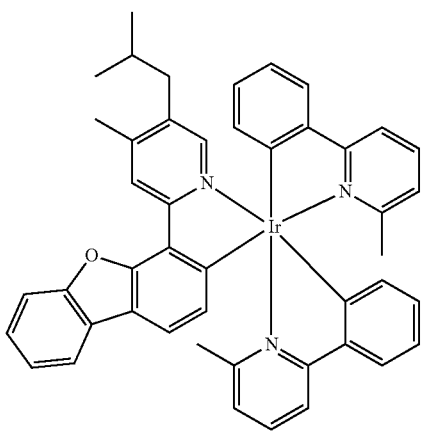
Compound 321
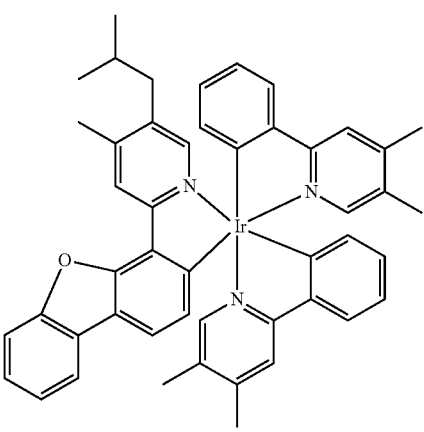
Compound 625
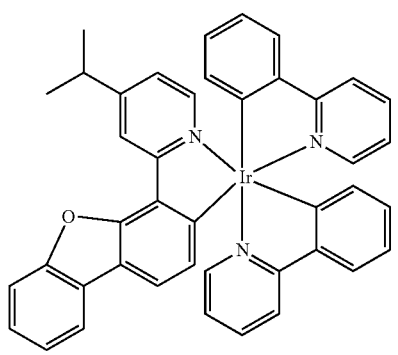
Compound 626
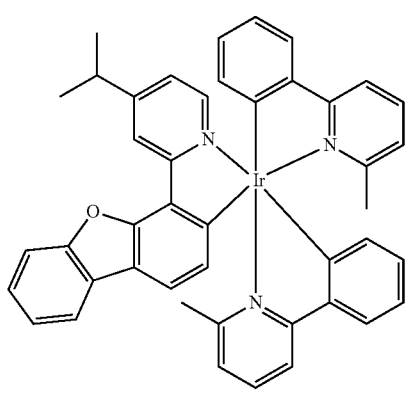
-continued
Compound 627
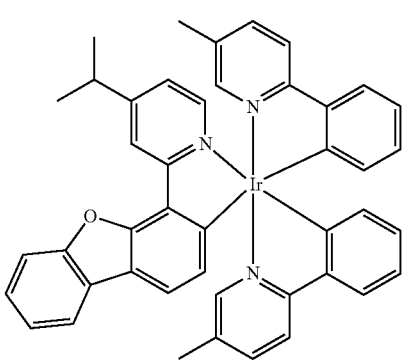
Compound 628
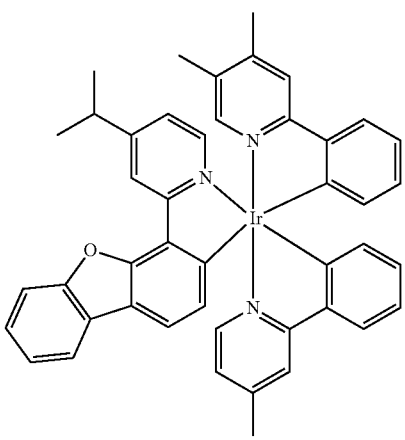
Compound 633
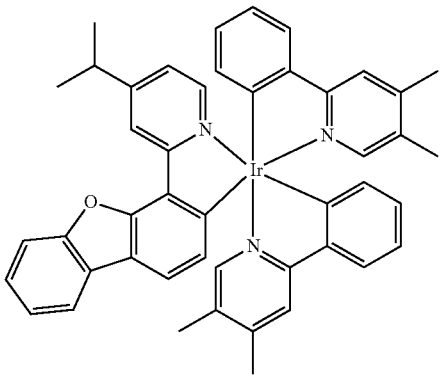
Compound 643
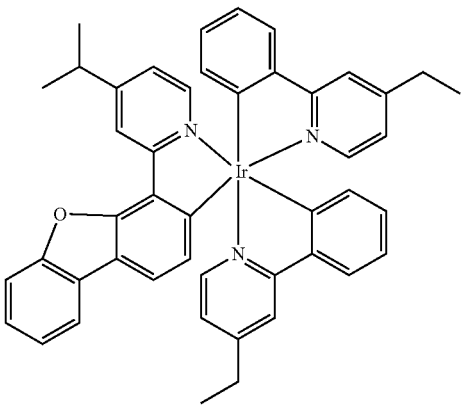

-continued

Compound 652

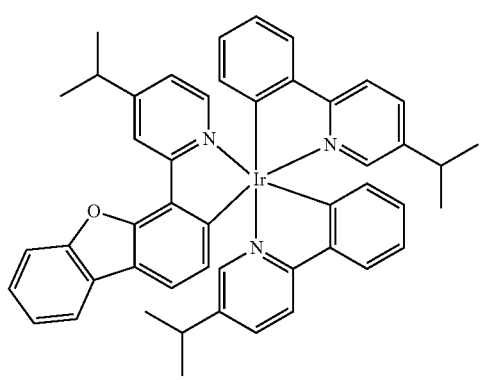

Compound 653

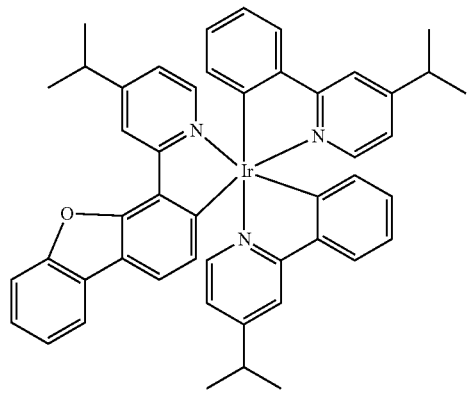

-continued

Compound 1145

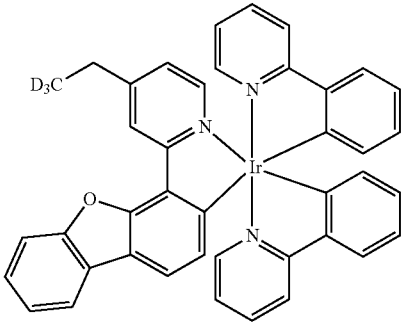

Compound 1146

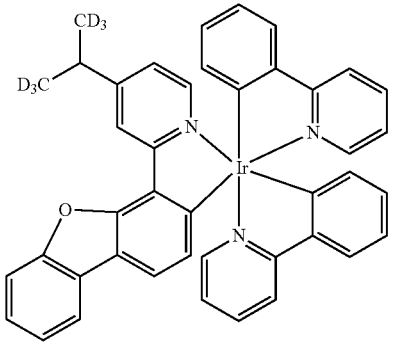

In one embodiment, suitable $R_1$-$R_6$ groups in the compounds of Formula I include the configurations of substituents in Table 1.

TABLE 1

| Compound # | $R_1$ | $R_2$ | $R_3$ | $R_4$ | $R_5$ | $R_6$ |
|---|---|---|---|---|---|---|
| 1. | H | Ethyl | H | H | H | H |
| 2. | H | Ethyl | Methyl | H | H | H |
| 3. | H | Ethyl | H | Methyl | H | H |
| 4. | H | Ethyl | H | H | Methyl | H |
| 5. | H | Ethyl | H | H | H | Methyl |
| 6. | H | Ethyl | Methyl | Methyl | H | H |
| 7. | H | Ethyl | Methyl | H | Methyl | H |
| 8. | H | Ethyl | Methyl | H | H | Methyl |
| 9. | H | Ethyl | H | Methyl | Methyl | H |
| 10. | H | Ethyl | H | Methyl | H | Methyl |
| 11. | H | Ethyl | H | H | Methyl | Methyl |
| 12. | H | Ethyl | Methyl | Methyl | Methyl | H |
| 13. | H | Ethyl | Methyl | Methyl | H | Methyl |
| 14. | H | Ethyl | Methyl | H | Methyl | Methyl |
| 15. | H | Ethyl | H | Methyl | Methyl | Methyl |
| 16. | H | Ethyl | Methyl | Methyl | Methyl | Methyl |
| 17. | H | Ethyl | Ethyl | H | H | H |
| 18. | H | Ethyl | H | Ethyl | H | H |
| 19. | H | Ethyl | H | H | Ethyl | H |
| 20. | H | Ethyl | H | H | H | Ethyl |
| 21. | H | Ethyl | Methyl | Ethyl | H | H |
| 22. | H | Ethyl | Methyl | H | Ethyl | H |
| 23. | H | Ethyl | Methyl | H | H | Ethyl |
| 24. | H | Ethyl | H | Ethyl | Methyl | H |
| 25. | H | Ethyl | H | Ethyl | Ethyl | H |
| 26. | H | Ethyl | H | Methyl | Ethyl | H |
| 27. | H | Ethyl | Isopropyl | H | H | H |
| 28. | H | Ethyl | H | Isopropyl | H | H |
| 29. | H | Ethyl | H | H | Isopropyl | H |
| 30. | H | Ethyl | H | H | H | Isopropyl |
| 31. | H | Ethyl | Methyl | Isopropyl | H | H |
| 32. | H | Ethyl | Methyl | H | Isopropyl | H |
| 33. | H | Ethyl | Methyl | H | H | Isopropyl |
| 34. | H | Ethyl | H | Isopropyl | Methyl | H |
| 35. | H | Ethyl | H | Isopropyl | Isopropyl | H |

TABLE 1-continued

| Compound # | $R_1$ | $R_2$ | $R_3$ | $R_4$ | $R_5$ | $R_6$ |
|---|---|---|---|---|---|---|
| 36. | H | Ethyl | H | Methyl | Isopropyl | H |
| 37. | H | Ethyl | H | Isopropyl | Ethyl | H |
| 38. | H | Ethyl | H | Ethyl | Isopropyl | H |
| 39. | H | Ethyl | Isobutyl | H | H | H |
| 40. | H | Ethyl | H | Isobutyl | H | H |
| 41. | H | Ethyl | H | H | Isobutyl | H |
| 42. | H | Ethyl | H | H | H | Isobutyl |
| 43. | H | Ethyl | Methyl | Isobutyl | H | H |
| 44. | H | Ethyl | Methyl | H | Isobutyl | H |
| 45. | H | Ethyl | Methyl | H | H | Isobutyl |
| 46. | H | Ethyl | H | Isobutyl | Methyl | H |
| 47. | H | Ethyl | H | Isobutyl | Isobutyl | H |
| 48. | H | Ethyl | H | Methyl | Isobutyl | H |
| 49. | H | Ethyl | H | Isobutyl | Ethyl | H |
| 50. | H | Ethyl | H | Ethyl | Isobutyl | H |
| 51. | H | Ethyl | H | Isobutyl | Isopropyl | H |
| 52. | H | Ethyl | H | Isopropyl | Isobutyl | H |
| 53. | H | Isopropyl | H | H | H | H |
| 54. | H | Isopropyl | Methyl | H | H | H |
| 55. | H | Isopropyl | H | Methyl | H | H |
| 56. | H | Isopropyl | H | H | Methyl | H |
| 57. | H | Isopropyl | H | H | H | Methyl |
| 58. | H | Isopropyl | Methyl | Methyl | H | H |
| 59. | H | Isopropyl | Methyl | H | Methyl | H |
| 60. | H | Isopropyl | Methyl | H | H | Methyl |
| 61. | H | Isopropyl | H | Methyl | Methyl | H |
| 62. | H | Isopropyl | H | Methyl | H | Methyl |
| 63. | H | Isopropyl | H | H | Methyl | Methyl |
| 64. | H | Isopropyl | Methyl | Methyl | Methyl | H |
| 65. | H | Isopropyl | Methyl | Methyl | H | Methyl |
| 66. | H | Isopropyl | Methyl | H | Methyl | Methyl |
| 67. | H | Isopropyl | H | Methyl | Methyl | Methyl |
| 68. | H | Isopropyl | Methyl | Methyl | Methyl | Methyl |
| 69. | H | Isopropyl | Ethyl | H | H | H |
| 70. | H | Isopropyl | H | Ethyl | H | H |
| 71. | H | Isopropyl | H | H | Ethyl | H |
| 72. | H | Isopropyl | H | H | H | Ethyl |
| 73. | H | Isopropyl | Methyl | Ethyl | H | H |
| 74. | H | Isopropyl | Methyl | H | Ethyl | H |
| 75. | H | Isopropyl | Methyl | H | H | Ethyl |
| 76. | H | Isopropyl | H | Ethyl | Methyl | H |
| 77. | H | Isopropyl | H | Ethyl | Ethyl | H |
| 78. | H | Isopropyl | H | Methyl | Ethyl | H |
| 79. | H | Isopropyl | Isopropyl | H | H | H |
| 80. | H | Isopropyl | H | Isopropyl | H | H |
| 81. | H | Isopropyl | H | H | Isopropyl | H |
| 82. | H | Isopropyl | H | H | H | Isopropyl |
| 83. | H | Isopropyl | Methyl | Isopropyl | H | H |
| 84. | H | Isopropyl | Methyl | H | Isopropyl | H |
| 85. | H | Isopropyl | Methyl | H | H | Isopropyl |
| 86. | H | Isopropyl | H | Isopropyl | Methyl | H |
| 87. | H | Isopropyl | H | Isopropyl | Isopropyl | H |
| 88. | H | Isopropyl | H | Methyl | Isopropyl | H |
| 89. | H | Isopropyl | H | Isopropyl | Ethyl | H |
| 90. | H | Isopropyl | H | Ethyl | Isopropyl | H |
| 91. | H | Isopropyl | Isobutyl | H | H | H |
| 92. | H | Isopropyl | H | Isobutyl | H | H |
| 93. | H | Isopropyl | H | H | Isobutyl | H |
| 94. | H | Isopropyl | H | H | H | Isobutyl |
| 95. | H | Isopropyl | Methyl | Isobutyl | H | H |
| 96. | H | Isopropyl | Methyl | H | Isobutyl | H |
| 97. | H | Isopropyl | Methyl | H | H | Isobutyl |
| 98. | H | Isopropyl | H | Isobutyl | Methyl | H |
| 99. | H | Isopropyl | H | Isobutyl | Isobutyl | H |
| 100. | H | Isopropyl | H | Methyl | Isobutyl | H |
| 101. | H | Isopropyl | H | Isobutyl | Ethyl | H |
| 102. | H | Isopropyl | H | Ethyl | Isobutyl | H |
| 103. | H | Isopropyl | H | Isobutyl | Isopropyl | H |
| 104. | H | Isopropyl | H | Isopropyl | Isobutyl | H |
| 105. | H | Isobutyl | H | H | H | H |
| 106. | H | Isobutyl | Methyl | H | H | H |
| 107. | H | Isobutyl | H | Methyl | H | H |
| 108. | H | Isobutyl | H | H | Methyl | H |
| 109. | H | Isobutyl | H | H | H | Methyl |
| 110. | H | Isobutyl | Methyl | Methyl | H | H |
| 111. | H | Isobutyl | Methyl | H | Methyl | H |
| 112. | H | Isobutyl | Methyl | H | H | Methyl |
| 113. | H | Isobutyl | H | Methyl | Methyl | H |

TABLE 1-continued

| Compound # | R₁ | R₂ | R₃ | R₄ | R₅ | R₆ |
|---|---|---|---|---|---|---|
| 114. | H | Isobutyl | H | Methyl | H | Methyl |
| 115. | H | Isobutyl | H | H | Methyl | Methyl |
| 116. | H | Isobutyl | Methyl | Methyl | Methyl | H |
| 117. | H | Isobutyl | Methyl | Methyl | H | Methyl |
| 118. | H | Isobutyl | Methyl | H | Methyl | Methyl |
| 119. | H | Isobutyl | H | Methyl | Methyl | Methyl |
| 120. | H | Isobutyl | Methyl | Methyl | Methyl | Methyl |
| 121. | H | Isobutyl | Ethyl | H | H | H |
| 122. | H | Isobutyl | H | Ethyl | H | H |
| 123. | H | Isobutyl | H | H | Ethyl | H |
| 124. | H | Isobutyl | H | H | H | Ethyl |
| 125. | H | Isobutyl | Methyl | Ethyl | H | H |
| 126. | H | Isobutyl | Methyl | H | Ethyl | H |
| 127. | H | Isobutyl | Methyl | H | H | Ethyl |
| 128. | H | Isobutyl | H | Ethyl | Methyl | H |
| 129. | H | Isobutyl | H | Ethyl | Ethyl | H |
| 130. | H | Isobutyl | H | Methyl | Ethyl | H |
| 131. | H | Isobutyl | Isopropyl | H | H | H |
| 132. | H | Isobutyl | H | Isopropyl | H | H |
| 133. | H | Isobutyl | H | H | Isopropyl | H |
| 134. | H | Isobutyl | H | H | H | Isopropyl |
| 135. | H | Isobutyl | Methyl | Isopropyl | H | H |
| 136. | H | Isobutyl | Methyl | H | Isopropyl | H |
| 137. | H | Isobutyl | Methyl | H | H | Isopropyl |
| 138. | H | Isobutyl | H | Isopropyl | Methyl | H |
| 139. | H | Isobutyl | H | Isopropyl | Isopropyl | H |
| 140. | H | Isobutyl | H | Methyl | Isopropyl | H |
| 141. | H | Isobutyl | H | Isopropyl | Ethyl | H |
| 142. | H | Isobutyl | H | Ethyl | Isopropyl | H |
| 143. | H | Isobutyl | Isobutyl | H | H | H |
| 144. | H | Isobutyl | H | Isobutyl | H | H |
| 145. | H | Isobutyl | H | H | Isobutyl | H |
| 146. | H | Isobutyl | H | H | H | Isobutyl |
| 147. | H | Isobutyl | Methyl | Isobutyl | H | H |
| 148. | H | Isobutyl | Methyl | H | Isobutyl | H |
| 149. | H | Isobutyl | Methyl | H | H | Isobutyl |
| 150. | H | Isobutyl | H | Isobutyl | Methyl | H |
| 151. | H | Isobutyl | H | Isobutyl | Isobutyl | H |
| 152. | H | Isobutyl | H | Methyl | Isobutyl | H |
| 153. | H | Isobutyl | H | Isobutyl | Ethyl | H |
| 154. | H | Isobutyl | H | Ethyl | Isobutyl | H |
| 155. | H | Isobutyl | H | Isobutyl | Isopropyl | H |
| 156. | H | Isobutyl | H | Isopropyl | Isobutyl | H |
| 157. | Methyl | Methyl | H | H | H | H |
| 158. | Methyl | Methyl | Methyl | H | H | H |
| 159. | Methyl | Methyl | H | Methyl | H | H |
| 160. | Methyl | Methyl | H | H | Methyl | H |
| 161. | Methyl | Methyl | H | H | H | Methyl |
| 162. | Methyl | Methyl | Methyl | Methyl | H | H |
| 163. | Methyl | Methyl | Methyl | H | Methyl | H |
| 164. | Methyl | Methyl | Methyl | H | H | Methyl |
| 165. | Methyl | Methyl | H | Methyl | Methyl | H |
| 166. | Methyl | Methyl | H | Methyl | H | Methyl |
| 167. | Methyl | Methyl | H | H | Methyl | Methyl |
| 168. | Methyl | Methyl | Methyl | Methyl | Methyl | H |
| 169. | Methyl | Methyl | Methyl | Methyl | H | Methyl |
| 170. | Methyl | Methyl | Methyl | H | Methyl | Methyl |
| 171. | Methyl | Methyl | H | Methyl | Methyl | Methyl |
| 172. | Methyl | Methyl | Methyl | Methyl | Methyl | Methyl |
| 173. | Methyl | Methyl | Ethyl | H | H | H |
| 174. | Methyl | Methyl | H | Ethyl | H | H |
| 175. | Methyl | Methyl | H | H | Ethyl | H |
| 176. | Methyl | Methyl | H | H | H | Ethyl |
| 177. | Methyl | Methyl | Methyl | Ethyl | H | H |
| 178. | Methyl | Methyl | Methyl | H | Ethyl | H |
| 179. | Methyl | Methyl | Methyl | H | H | Ethyl |
| 180. | Methyl | Methyl | H | Ethyl | Methyl | H |
| 181. | Methyl | Methyl | H | Ethyl | Ethyl | H |
| 182. | Methyl | Methyl | H | Methyl | Ethyl | H |
| 183. | Methyl | Methyl | Isopropyl | H | H | H |
| 184. | Methyl | Methyl | H | Isopropyl | H | H |
| 185. | Methyl | Methyl | H | H | Isopropyl | H |
| 186. | Methyl | Methyl | H | H | H | Isopropyl |
| 187. | Methyl | Methyl | Methyl | Isopropyl | H | H |
| 188. | Methyl | Methyl | Methyl | H | Isopropyl | H |
| 189. | Methyl | Methyl | Methyl | H | H | Isopropyl |
| 190. | Methyl | Methyl | H | Isopropyl | Methyl | H |
| 191. | Methyl | Methyl | H | Isopropyl | Isopropyl | H |

TABLE 1-continued

| Compound # | R₁ | R₂ | R₃ | R₄ | R₅ | R₆ |
|---|---|---|---|---|---|---|
| 192. | Methyl | Methyl | H | Methyl | Isopropyl | H |
| 193. | Methyl | Methyl | H | Isopropyl | Ethyl | H |
| 194. | Methyl | Methyl | H | Ethyl | Isopropyl | H |
| 195. | Methyl | Methyl | Isobutyl | H | H | H |
| 196. | Methyl | Methyl | H | Isobutyl | H | H |
| 197. | Methyl | Methyl | H | H | Isobutyl | H |
| 198. | Methyl | Methyl | H | H | H | Isobutyl |
| 199. | Methyl | Methyl | Methyl | Isobutyl | H | H |
| 200. | Methyl | Methyl | Methyl | H | Isobutyl | H |
| 201. | Methyl | Methyl | Methyl | H | H | Isobutyl |
| 202. | Methyl | Methyl | H | Isobutyl | Methyl | H |
| 203. | Methyl | Methyl | H | Isobutyl | Isobutyl | H |
| 204. | Methyl | Methyl | H | Methyl | Isobutyl | H |
| 205. | Methyl | Methyl | H | Isobutyl | Ethyl | H |
| 206. | Methyl | Methyl | H | Ethyl | Isobutyl | H |
| 207. | Methyl | Methyl | H | Isobutyl | Isopropyl | H |
| 208. | Methyl | Methyl | H | Isopropyl | Isobutyl | H |
| 209. | Methyl | Ethyl | H | H | H | H |
| 210. | Methyl | Ethyl | Methyl | H | H | H |
| 211. | Methyl | Ethyl | H | Methyl | H | H |
| 212. | Methyl | Ethyl | H | H | Methyl | H |
| 213. | Methyl | Ethyl | H | H | H | Methyl |
| 214. | Methyl | Ethyl | Methyl | Methyl | H | H |
| 215. | Methyl | Ethyl | Methyl | H | Methyl | H |
| 216. | Methyl | Ethyl | Methyl | H | H | Methyl |
| 217. | Methyl | Ethyl | H | Methyl | Methyl | H |
| 218. | Methyl | Ethyl | H | Methyl | H | Methyl |
| 219. | Methyl | Ethyl | H | H | Methyl | Methyl |
| 220. | Methyl | Ethyl | Methyl | Methyl | Methyl | H |
| 221. | Methyl | Ethyl | Methyl | Methyl | H | Methyl |
| 222. | Methyl | Ethyl | Methyl | H | Methyl | Methyl |
| 223. | Methyl | Ethyl | H | Methyl | Methyl | Methyl |
| 224. | Methyl | Ethyl | Methyl | Methyl | Methyl | Methyl |
| 225. | Methyl | Ethyl | Ethyl | H | H | H |
| 226. | Methyl | Ethyl | H | Ethyl | H | H |
| 227. | Methyl | Ethyl | H | H | Ethyl | H |
| 228. | Methyl | Ethyl | H | H | H | Ethyl |
| 229. | Methyl | Ethyl | Methyl | Ethyl | H | H |
| 230. | Methyl | Ethyl | Methyl | H | Ethyl | H |
| 231. | Methyl | Ethyl | Methyl | H | H | Ethyl |
| 232. | Methyl | Ethyl | H | Ethyl | Methyl | H |
| 233. | Methyl | Ethyl | H | Ethyl | Ethyl | H |
| 234. | Methyl | Ethyl | H | Methyl | Ethyl | H |
| 235. | Methyl | Ethyl | Isopropyl | H | H | H |
| 236. | Methyl | Ethyl | H | Isopropyl | H | H |
| 237. | Methyl | Ethyl | H | H | Isopropyl | H |
| 238. | Methyl | Ethyl | H | H | H | Isopropyl |
| 239. | Methyl | Ethyl | Methyl | Isopropyl | H | H |
| 240. | Methyl | Ethyl | Methyl | H | Isopropyl | H |
| 241. | Methyl | Ethyl | Methyl | H | H | Isopropyl |
| 242. | Methyl | Ethyl | H | Isopropyl | Methyl | H |
| 243. | Methyl | Ethyl | H | Isopropyl | Isopropyl | H |
| 244. | Methyl | Ethyl | H | Methyl | Isopropyl | H |
| 245. | Methyl | Ethyl | H | Isopropyl | Ethyl | H |
| 246. | Methyl | Ethyl | H | Ethyl | Isopropyl | H |
| 247. | Methyl | Ethyl | Isobutyl | H | H | H |
| 248. | Methyl | Ethyl | H | Isobutyl | H | H |
| 249. | Methyl | Ethyl | H | H | Isobutyl | H |
| 250. | Methyl | Ethyl | H | H | H | Isobutyl |
| 251. | Methyl | Ethyl | Methyl | Isobutyl | H | H |
| 252. | Methyl | Ethyl | Methyl | H | Isobutyl | H |
| 253. | Methyl | Ethyl | Methyl | H | H | Isobutyl |
| 254. | Methyl | Ethyl | H | Isobutyl | Methyl | H |
| 255. | Methyl | Ethyl | H | Isobutyl | Isobutyl | H |
| 256. | Methyl | Ethyl | H | Methyl | Isobutyl | H |
| 257. | Methyl | Ethyl | H | Isobutyl | Ethyl | H |
| 258. | Methyl | Ethyl | H | Ethyl | Isobutyl | H |
| 259. | Methyl | Ethyl | H | Isobutyl | Isopropyl | H |
| 260. | Methyl | Ethyl | H | Isopropyl | Isobutyl | H |
| 261. | Methyl | Isopropyl | H | H | H | H |
| 262. | Methyl | Isopropyl | Methyl | H | H | H |
| 263. | Methyl | Isopropyl | H | Methyl | H | H |
| 264. | Methyl | Isopropyl | H | H | Methyl | H |
| 265. | Methyl | Isopropyl | H | H | H | Methyl |
| 266. | Methyl | Isopropyl | Methyl | Methyl | H | H |
| 267. | Methyl | Isopropyl | Methyl | H | Methyl | H |
| 268. | Methyl | Isopropyl | Methyl | H | H | Methyl |
| 269. | Methyl | Isopropyl | H | Methyl | Methyl | H |

TABLE 1-continued

| Compound # | R₁ | R₂ | R₃ | R₄ | R₅ | R₆ |
|---|---|---|---|---|---|---|
| 270. | Methyl | Isopropyl | H | Methyl | H | Methyl |
| 271. | Methyl | Isopropyl | H | H | Methyl | Methyl |
| 272. | Methyl | Isopropyl | Methyl | Methyl | Methyl | H |
| 273. | Methyl | Isopropyl | Methyl | Methyl | H | Methyl |
| 274. | Methyl | Isopropyl | Methyl | H | Methyl | Methyl |
| 275. | Methyl | Isopropyl | H | Methyl | Methyl | Methyl |
| 276. | Methyl | Isopropyl | Methyl | Methyl | Methyl | Methyl |
| 277. | Methyl | Isopropyl | Ethyl | H | H | H |
| 278. | Methyl | Isopropyl | H | Ethyl | H | H |
| 279. | Methyl | Isopropyl | H | H | Ethyl | H |
| 280. | Methyl | Isopropyl | H | H | H | Ethyl |
| 281. | Methyl | Isopropyl | Methyl | Ethyl | H | H |
| 282. | Methyl | Isopropyl | Methyl | H | Ethyl | H |
| 283. | Methyl | Isopropyl | Methyl | H | H | Ethyl |
| 284. | Methyl | Isopropyl | H | Ethyl | Methyl | H |
| 285. | Methyl | Isopropyl | H | Ethyl | Ethyl | H |
| 286. | Methyl | Isopropyl | H | Methyl | Ethyl | H |
| 287. | Methyl | Isopropyl | Isopropyl | H | H | H |
| 288. | Methyl | Isopropyl | H | Isopropyl | H | H |
| 289. | Methyl | Isopropyl | H | H | Isopropyl | H |
| 290. | Methyl | Isopropyl | H | H | H | Isopropyl |
| 291. | Methyl | Isopropyl | Methyl | Isopropyl | H | H |
| 292. | Methyl | Isopropyl | Methyl | H | Isopropyl | H |
| 293. | Methyl | Isopropyl | Methyl | H | H | Isopropyl |
| 294. | Methyl | Isopropyl | H | Isopropyl | Methyl | H |
| 295. | Methyl | Isopropyl | H | Isopropyl | Isopropyl | H |
| 296. | Methyl | Isopropyl | H | Methyl | Isopropyl | H |
| 297. | Methyl | Isopropyl | H | Isopropyl | Ethyl | H |
| 298. | Methyl | Isopropyl | H | Ethyl | Isopropyl | H |
| 299. | Methyl | Isopropyl | Isobutyl | H | H | H |
| 300. | Methyl | Isopropyl | H | Isobutyl | H | H |
| 301. | Methyl | Isopropyl | H | H | Isobutyl | H |
| 302. | Methyl | Isopropyl | H | H | H | Isobutyl |
| 303. | Methyl | Isopropyl | Methyl | Isobutyl | H | H |
| 304. | Methyl | Isopropyl | Methyl | H | Isobutyl | H |
| 305. | Methyl | Isopropyl | Methyl | H | H | Isobutyl |
| 306. | Methyl | Isopropyl | H | Isobutyl | Methyl | H |
| 307. | Methyl | Isopropyl | H | Isobutyl | Isobutyl | H |
| 308. | Methyl | Isopropyl | H | Methyl | Isobutyl | H |
| 309. | Methyl | Isopropyl | H | Isobutyl | Ethyl | H |
| 310. | Methyl | Isopropyl | H | Ethyl | Isobutyl | H |
| 311. | Methyl | Isopropyl | H | Isobutyl | Isopropyl | H |
| 312. | Methyl | Isopropyl | H | Isopropyl | Isobutyl | H |
| 313. | Methyl | Isobutyl | H | H | H | H |
| 314. | Methyl | Isobutyl | Methyl | H | H | H |
| 315. | Methyl | Isobutyl | H | Methyl | H | H |
| 316. | Methyl | Isobutyl | H | H | Methyl | H |
| 317. | Methyl | Isobutyl | H | H | H | Methyl |
| 318. | Methyl | Isobutyl | Methyl | Methyl | H | H |
| 319. | Methyl | Isobutyl | Methyl | H | Methyl | H |
| 320. | Methyl | Isobutyl | Methyl | H | H | Methyl |
| 321. | Methyl | Isobutyl | H | Methyl | Methyl | H |
| 322. | Methyl | Isobutyl | H | Methyl | H | Methyl |
| 323. | Methyl | Isobutyl | H | H | Methyl | Methyl |
| 324. | Methyl | Isobutyl | Methyl | Methyl | Methyl | H |
| 325. | Methyl | Isobutyl | Methyl | Methyl | H | Methyl |
| 326. | Methyl | Isobutyl | Methyl | H | Methyl | Methyl |
| 327. | Methyl | Isobutyl | H | Methyl | Methyl | Methyl |
| 328. | Methyl | Isobutyl | Methyl | Methyl | Methyl | Methyl |
| 329. | Methyl | Isobutyl | Ethyl | H | H | H |
| 330. | Methyl | Isobutyl | H | Ethyl | H | H |
| 331. | Methyl | Isobutyl | H | H | Ethyl | H |
| 332. | Methyl | Isobutyl | H | H | H | Ethyl |
| 333. | Methyl | Isobutyl | Methyl | Ethyl | H | H |
| 334. | Methyl | Isobutyl | Methyl | H | Ethyl | H |
| 335. | Methyl | Isobutyl | Methyl | H | H | Ethyl |
| 336. | Methyl | Isobutyl | H | Ethyl | Methyl | H |
| 337. | Methyl | Isobutyl | H | Ethyl | Ethyl | H |
| 338. | Methyl | Isobutyl | H | Methyl | Ethyl | H |
| 339. | Methyl | Isobutyl | Isopropyl | H | H | H |
| 340. | Methyl | Isobutyl | H | Isopropyl | H | H |
| 341. | Methyl | Isobutyl | H | H | Isopropyl | H |
| 342. | Methyl | Isobutyl | H | H | H | Isopropyl |
| 343. | Methyl | Isobutyl | Methyl | Isopropyl | H | H |
| 344. | Methyl | Isobutyl | Methyl | H | Isopropyl | H |
| 345. | Methyl | Isobutyl | Methyl | H | H | Isopropyl |
| 346. | Methyl | Isobutyl | H | Isopropyl | Methyl | H |
| 347. | Methyl | Isobutyl | H | Isopropyl | Isopropyl | H |

TABLE 1-continued

| Compound # | $R_1$ | $R_2$ | $R_3$ | $R_4$ | $R_5$ | $R_6$ |
|---|---|---|---|---|---|---|
| 348. | Methyl | Isobutyl | H | Methyl | Isopropyl | H |
| 349. | Methyl | Isobutyl | H | Isopropyl | Ethyl | H |
| 350. | Methyl | Isobutyl | H | Ethyl | Isopropyl | H |
| 351. | Methyl | Isobutyl | Isobutyl | H | H | H |
| 352. | Methyl | Isobutyl | H | Isobutyl | H | H |
| 353. | Methyl | Isobutyl | H | H | Isobutyl | H |
| 354. | Methyl | Isobutyl | H | H | H | Isobutyl |
| 355. | Methyl | Isobutyl | Methyl | Isobutyl | H | H |
| 356. | Methyl | Isobutyl | Methyl | H | Isobutyl | H |
| 357. | Methyl | Isobutyl | Methyl | H | H | Isobutyl |
| 358. | Methyl | Isobutyl | H | Isobutyl | Methyl | H |
| 359. | Methyl | Isobutyl | H | Isobutyl | Isobutyl | H |
| 360. | Methyl | Isobutyl | H | Methyl | Isobutyl | H |
| 361. | Methyl | Isobutyl | H | Isobutyl | Ethyl | H |
| 362. | Methyl | Isobutyl | H | Ethyl | Isobutyl | H |
| 363. | Methyl | Isobutyl | H | Isobutyl | Isopropyl | H |
| 364. | Methyl | Isobutyl | H | Isopropyl | Isobutyl | H |
| 365. | Ethyl | H | H | H | H | H |
| 366. | Ethyl | H | Methyl | H | H | H |
| 367. | Ethyl | H | H | Methyl | H | H |
| 368. | Ethyl | H | H | H | Methyl | H |
| 369. | Ethyl | H | H | H | H | Methyl |
| 370. | Ethyl | H | Methyl | Methyl | H | H |
| 371. | Ethyl | H | Methyl | H | Methyl | H |
| 372. | Ethyl | H | Methyl | H | H | Methyl |
| 373. | Ethyl | H | H | Methyl | Methyl | H |
| 374. | Ethyl | H | H | Methyl | H | Methyl |
| 375. | Ethyl | H | H | H | Methyl | Methyl |
| 376. | Ethyl | H | Methyl | Methyl | Methyl | H |
| 377. | Ethyl | H | Methyl | Methyl | H | Methyl |
| 378. | Ethyl | H | Methyl | H | Methyl | Methyl |
| 379. | Ethyl | H | H | Methyl | Methyl | Methyl |
| 380. | Ethyl | H | Methyl | Methyl | Methyl | Methyl |
| 381. | Ethyl | H | Ethyl | H | H | H |
| 382. | Ethyl | H | H | Ethyl | H | H |
| 383. | Ethyl | H | H | H | Ethyl | H |
| 384. | Ethyl | H | H | H | H | Ethyl |
| 385. | Ethyl | H | Methyl | Ethyl | H | H |
| 386. | Ethyl | H | Methyl | H | Ethyl | H |
| 387. | Ethyl | H | Methyl | H | H | Ethyl |
| 388. | Ethyl | H | H | Ethyl | Methyl | H |
| 389. | Ethyl | H | H | Ethyl | Ethyl | H |
| 390. | Ethyl | H | H | Methyl | Ethyl | H |
| 391. | Ethyl | H | Isopropyl | H | H | H |
| 392. | Ethyl | H | H | Isopropyl | H | H |
| 393. | Ethyl | H | H | H | Isopropyl | H |
| 394. | Ethyl | H | H | H | H | Isopropyl |
| 395. | Ethyl | H | Methyl | Isopropyl | H | H |
| 396. | Ethyl | H | Methyl | H | Isopropyl | H |
| 397. | Ethyl | H | Methyl | H | H | Isopropyl |
| 398. | Ethyl | H | H | Isopropyl | Methyl | H |
| 399. | Ethyl | H | H | Isopropyl | Isopropyl | H |
| 400. | Ethyl | H | H | Methyl | Isopropyl | H |
| 401. | Ethyl | H | H | Isopropyl | Ethyl | H |
| 402. | Ethyl | H | H | Ethyl | Isopropyl | H |
| 403. | Ethyl | H | Isobutyl | H | H | H |
| 404. | Ethyl | H | H | Isobutyl | H | H |
| 405. | Ethyl | H | H | H | Isobutyl | H |
| 406. | Ethyl | H | H | H | H | Isobutyl |
| 407. | Ethyl | H | Methyl | Isobutyl | H | H |
| 408. | Ethyl | H | Methyl | H | Isobutyl | H |
| 409. | Ethyl | H | Methyl | H | H | Isobutyl |
| 410. | Ethyl | H | H | Isobutyl | Methyl | H |
| 411. | Ethyl | H | H | Isobutyl | Isobutyl | H |
| 412. | Ethyl | H | H | Methyl | Isobutyl | H |
| 413. | Ethyl | H | H | Isobutyl | Ethyl | H |
| 414. | Ethyl | H | H | Ethyl | Isobutyl | H |
| 415. | Ethyl | H | H | Isobutyl | Isopropyl | H |
| 416. | Ethyl | H | H | Isopropyl | Isobutyl | H |
| 417. | Ethyl | Methyl | H | H | H | H |
| 418. | Ethyl | Methyl | Methyl | H | H | H |
| 419. | Ethyl | Methyl | H | Methyl | H | H |
| 420. | Ethyl | Methyl | H | H | Methyl | H |
| 421. | Ethyl | Methyl | H | H | H | Methyl |
| 422. | Ethyl | Methyl | Methyl | Methyl | H | H |
| 423. | Ethyl | Methyl | Methyl | H | Methyl | H |
| 424. | Ethyl | Methyl | Methyl | H | H | Methyl |
| 425. | Ethyl | Methyl | H | Methyl | Methyl | H |

TABLE 1-continued

| Compound # | $R_1$ | $R_2$ | $R_3$ | $R_4$ | $R_5$ | $R_6$ |
|---|---|---|---|---|---|---|
| 426. | Ethyl | Methyl | H | Methyl | H | Methyl |
| 427. | Ethyl | Methyl | H | H | Methyl | Methyl |
| 428. | Ethyl | Methyl | Methyl | Methyl | Methyl | H |
| 429. | Ethyl | Methyl | Methyl | Methyl | H | Methyl |
| 430. | Ethyl | Methyl | Methyl | H | Methyl | Methyl |
| 431. | Ethyl | Methyl | H | Methyl | Methyl | Methyl |
| 432. | Ethyl | Methyl | Methyl | Methyl | Methyl | Methyl |
| 433. | Ethyl | Methyl | Ethyl | H | H | H |
| 434. | Ethyl | Methyl | H | Ethyl | H | H |
| 435. | Ethyl | Methyl | H | H | Ethyl | H |
| 436. | Ethyl | Methyl | H | H | H | Ethyl |
| 437. | Ethyl | Methyl | Methyl | Ethyl | H | H |
| 438. | Ethyl | Methyl | Methyl | H | Ethyl | H |
| 439. | Ethyl | Methyl | Methyl | H | H | Ethyl |
| 440. | Ethyl | Methyl | H | Ethyl | Methyl | H |
| 441. | Ethyl | Methyl | H | Ethyl | Ethyl | H |
| 442. | Ethyl | Methyl | H | Methyl | Ethyl | H |
| 443. | Ethyl | Methyl | Isopropyl | H | H | H |
| 444. | Ethyl | Methyl | H | Isopropyl | H | H |
| 445. | Ethyl | Methyl | H | H | Isopropyl | H |
| 446. | Ethyl | Methyl | H | H | H | Isopropyl |
| 447. | Ethyl | Methyl | Methyl | Isopropyl | H | H |
| 448. | Ethyl | Methyl | Methyl | H | Isopropyl | H |
| 449. | Ethyl | Methyl | Methyl | H | H | Isopropyl |
| 450. | Ethyl | Methyl | H | Isopropyl | Methyl | H |
| 451. | Ethyl | Methyl | H | Isopropyl | Isopropyl | H |
| 452. | Ethyl | Methyl | H | Methyl | Isopropyl | H |
| 453. | Ethyl | Methyl | H | Isopropyl | Ethyl | H |
| 454. | Ethyl | Methyl | H | Ethyl | Isopropyl | H |
| 455. | Ethyl | Methyl | Isobutyl | H | H | H |
| 456. | Ethyl | Methyl | H | Isobutyl | H | H |
| 457. | Ethyl | Methyl | H | H | Isobutyl | H |
| 458. | Ethyl | Methyl | H | H | H | Isobutyl |
| 459. | Ethyl | Methyl | Methyl | Isobutyl | H | H |
| 460. | Ethyl | Methyl | Methyl | H | Isobutyl | H |
| 461. | Ethyl | Methyl | Methyl | H | H | Isobutyl |
| 462. | Ethyl | Methyl | H | Isobutyl | Methyl | H |
| 463. | Ethyl | Methyl | H | Isobutyl | Isobutyl | H |
| 464. | Ethyl | Methyl | H | Methyl | Isobutyl | H |
| 465. | Ethyl | Methyl | H | Isobutyl | Ethyl | H |
| 466. | Ethyl | Methyl | H | Ethyl | Isobutyl | H |
| 467. | Ethyl | Methyl | H | Isobutyl | Isopropyl | H |
| 468. | Ethyl | Methyl | H | Isopropyl | Isobutyl | H |
| 469. | Ethyl | Ethyl | H | H | H | H |
| 470. | Ethyl | Ethyl | Methyl | H | H | H |
| 471. | Ethyl | Ethyl | H | Methyl | H | H |
| 472. | Ethyl | Ethyl | H | H | Methyl | H |
| 473. | Ethyl | Ethyl | H | H | H | Methyl |
| 474. | Ethyl | Ethyl | Methyl | Methyl | H | H |
| 475. | Ethyl | Ethyl | Methyl | H | Methyl | H |
| 476. | Ethyl | Ethyl | Methyl | H | H | Methyl |
| 477. | Ethyl | Ethyl | H | Methyl | Methyl | H |
| 478. | Ethyl | Ethyl | H | Methyl | H | Methyl |
| 479. | Ethyl | Ethyl | H | H | Methyl | Methyl |
| 480. | Ethyl | Ethyl | Methyl | Methyl | Methyl | H |
| 481. | Ethyl | Ethyl | Methyl | Methyl | H | Methyl |
| 482. | Ethyl | Ethyl | Methyl | H | Methyl | Methyl |
| 483. | Ethyl | Ethyl | H | Methyl | Methyl | Methyl |
| 484. | Ethyl | Ethyl | Methyl | Methyl | Methyl | Methyl |
| 485. | Ethyl | Ethyl | Ethyl | H | H | H |
| 486. | Ethyl | Ethyl | H | Ethyl | H | H |
| 487. | Ethyl | Ethyl | H | H | Ethyl | H |
| 488. | Ethyl | Ethyl | H | H | H | Ethyl |
| 489. | Ethyl | Ethyl | Methyl | Ethyl | H | H |
| 490. | Ethyl | Ethyl | Methyl | H | Ethyl | H |
| 491. | Ethyl | Ethyl | Methyl | H | H | Ethyl |
| 492. | Ethyl | Ethyl | H | Ethyl | Methyl | H |
| 493. | Ethyl | Ethyl | H | Ethyl | Ethyl | H |
| 494. | Ethyl | Ethyl | H | Methyl | Ethyl | H |
| 495. | Ethyl | Ethyl | Isopropyl | H | H | H |
| 496. | Ethyl | Ethyl | H | Isopropyl | H | H |
| 497. | Ethyl | Ethyl | H | H | Isopropyl | H |
| 498. | Ethyl | Ethyl | H | H | H | Isopropyl |
| 499. | Ethyl | Ethyl | Methyl | Isopropyl | H | H |
| 500. | Ethyl | Ethyl | Methyl | H | Isopropyl | H |
| 501. | Ethyl | Ethyl | Methyl | H | H | Isopropyl |
| 502. | Ethyl | Ethyl | H | Isopropyl | Methyl | H |
| 503. | Ethyl | Ethyl | H | Isopropyl | Isopropyl | H |

TABLE 1-continued

| Compound # | R₁ | R₂ | R₃ | R₄ | R₅ | R₆ |
|---|---|---|---|---|---|---|
| 504. | Ethyl | Ethyl | H | Methyl | Isopropyl | H |
| 505. | Ethyl | Ethyl | H | Isopropyl | Ethyl | H |
| 506. | Ethyl | Ethyl | H | Ethyl | Isopropyl | H |
| 507. | Ethyl | Ethyl | Isobutyl | H | H | H |
| 508. | Ethyl | Ethyl | H | Isobutyl | H | H |
| 509. | Ethyl | Ethyl | H | H | Isobutyl | H |
| 510. | Ethyl | Ethyl | H | H | H | Isobutyl |
| 511. | Ethyl | Ethyl | Methyl | Isobutyl | H | H |
| 512. | Ethyl | Ethyl | Methyl | H | Isobutyl | H |
| 513. | Ethyl | Ethyl | Methyl | H | H | Isobutyl |
| 514. | Ethyl | Ethyl | H | Isobutyl | Methyl | H |
| 515. | Ethyl | Ethyl | H | Isobutyl | Isobutyl | H |
| 516. | Ethyl | Ethyl | H | Methyl | Isobutyl | H |
| 517. | Ethyl | Ethyl | H | Isobutyl | Ethyl | H |
| 518. | Ethyl | Ethyl | H | Ethyl | Isobutyl | H |
| 519. | Ethyl | Ethyl | H | Isobutyl | Isopropyl | H |
| 520. | Ethyl | Ethyl | H | Isopropyl | Isobutyl | H |
| 521. | Ethyl | Isopropyl | H | H | H | H |
| 522. | Ethyl | Isopropyl | Methyl | H | H | H |
| 523. | Ethyl | Isopropyl | H | Methyl | H | H |
| 524. | Ethyl | Isopropyl | H | H | Methyl | H |
| 525. | Ethyl | Isopropyl | H | H | H | Methyl |
| 526. | Ethyl | Isopropyl | Methyl | Methyl | H | H |
| 527. | Ethyl | Isopropyl | Methyl | H | Methyl | H |
| 528. | Ethyl | Isopropyl | Methyl | H | H | Methyl |
| 529. | Ethyl | Isopropyl | H | Methyl | Methyl | H |
| 530. | Ethyl | Isopropyl | H | Methyl | H | Methyl |
| 531. | Ethyl | Isopropyl | H | H | Methyl | Methyl |
| 532. | Ethyl | Isopropyl | Methyl | Methyl | Methyl | H |
| 533. | Ethyl | Isopropyl | Methyl | Methyl | H | Methyl |
| 534. | Ethyl | Isopropyl | Methyl | H | Methyl | Methyl |
| 535. | Ethyl | Isopropyl | H | Methyl | Methyl | Methyl |
| 536. | Ethyl | Isopropyl | Methyl | Methyl | Methyl | Methyl |
| 537. | Ethyl | Isopropyl | Ethyl | H | H | H |
| 538. | Ethyl | Isopropyl | H | Ethyl | H | H |
| 539. | Ethyl | Isopropyl | H | H | Ethyl | H |
| 540. | Ethyl | Isopropyl | H | H | H | Ethyl |
| 541. | Ethyl | Isopropyl | Methyl | Ethyl | H | H |
| 542. | Ethyl | Isopropyl | Methyl | H | Ethyl | H |
| 543. | Ethyl | Isopropyl | Methyl | H | H | Ethyl |
| 544. | Ethyl | Isopropyl | H | Ethyl | Methyl | H |
| 545. | Ethyl | Isopropyl | H | Ethyl | Ethyl | H |
| 546. | Ethyl | Isopropyl | H | Methyl | Ethyl | H |
| 547. | Ethyl | Isopropyl | Isopropyl | H | H | H |
| 548. | Ethyl | Isopropyl | H | Isopropyl | H | H |
| 549. | Ethyl | Isopropyl | H | H | Isopropyl | H |
| 550. | Ethyl | Isopropyl | H | H | H | Isopropyl |
| 551. | Ethyl | Isopropyl | Methyl | Isopropyl | H | H |
| 552. | Ethyl | Isopropyl | Methyl | H | Isopropyl | H |
| 553. | Ethyl | Isopropyl | Methyl | H | H | Isopropyl |
| 554. | Ethyl | Isopropyl | H | Isopropyl | Methyl | H |
| 555. | Ethyl | Isopropyl | H | Isopropyl | Isopropyl | H |
| 556. | Ethyl | Isopropyl | H | Methyl | Isopropyl | H |
| 557. | Ethyl | Isopropyl | H | Isopropyl | Ethyl | H |
| 558. | Ethyl | Isopropyl | H | Ethyl | Isopropyl | H |
| 559. | Ethyl | Isopropyl | Isobutyl | H | H | H |
| 560. | Ethyl | Isopropyl | H | Isobutyl | H | H |
| 561. | Ethyl | Isopropyl | H | H | Isobutyl | H |
| 562. | Ethyl | Isopropyl | H | H | H | Isobutyl |
| 563. | Ethyl | Isopropyl | Methyl | Isobutyl | H | H |
| 564. | Ethyl | Isopropyl | Methyl | H | Isobutyl | H |
| 565. | Ethyl | Isopropyl | Methyl | H | H | Isobutyl |
| 566. | Ethyl | Isopropyl | H | Isobutyl | Methyl | H |
| 567. | Ethyl | Isopropyl | H | Isobutyl | Isobutyl | H |
| 568. | Ethyl | Isopropyl | H | Methyl | Isobutyl | H |
| 569. | Ethyl | Isopropyl | H | Isobutyl | Ethyl | H |
| 570. | Ethyl | Isopropyl | H | Ethyl | Isobutyl | H |
| 571. | Ethyl | Isopropyl | H | Isobutyl | Isopropyl | H |
| 572. | Ethyl | Isopropyl | H | Isopropyl | Isobutyl | H |
| 573. | Ethyl | Isobutyl | H | H | H | H |
| 574. | Ethyl | Isobutyl | Methyl | H | H | H |
| 575. | Ethyl | Isobutyl | H | Methyl | H | H |
| 576. | Ethyl | Isobutyl | H | H | Methyl | H |
| 577. | Ethyl | Isobutyl | H | H | H | Methyl |
| 578. | Ethyl | Isobutyl | Methyl | Methyl | H | H |
| 579. | Ethyl | Isobutyl | Methyl | H | Methyl | H |
| 580. | Ethyl | Isobutyl | Methyl | H | H | Methyl |
| 581. | Ethyl | Isobutyl | H | Methyl | Methyl | H |

TABLE 1-continued

| Compound # | R₁ | R₂ | R₃ | R₄ | R₅ | R₆ |
|---|---|---|---|---|---|---|
| 582. | Ethyl | Isobutyl | H | Methyl | H | Methyl |
| 583. | Ethyl | Isobutyl | H | H | Methyl | Methyl |
| 584. | Ethyl | Isobutyl | Methyl | Methyl | Methyl | H |
| 585. | Ethyl | Isobutyl | Methyl | Methyl | H | Methyl |
| 586. | Ethyl | Isobutyl | Methyl | H | Methyl | Methyl |
| 587. | Ethyl | Isobutyl | H | Methyl | Methyl | Methyl |
| 588. | Ethyl | Isobutyl | Methyl | Methyl | Methyl | Methyl |
| 589. | Ethyl | Isobutyl | Ethyl | H | H | H |
| 590. | Ethyl | Isobutyl | H | Ethyl | H | H |
| 591. | Ethyl | Isobutyl | H | H | Ethyl | H |
| 592. | Ethyl | Isobutyl | H | H | H | Ethyl |
| 593. | Ethyl | Isobutyl | Methyl | Ethyl | H | H |
| 594. | Ethyl | Isobutyl | Methyl | H | Ethyl | H |
| 595. | Ethyl | Isobutyl | Methyl | H | H | Ethyl |
| 596. | Ethyl | Isobutyl | H | Ethyl | Methyl | H |
| 597. | Ethyl | Isobutyl | H | Ethyl | Ethyl | H |
| 598. | Ethyl | Isobutyl | H | Methyl | Ethyl | H |
| 599. | Ethyl | Isobutyl | Isopropyl | H | H | H |
| 600. | Ethyl | Isobutyl | H | Isopropyl | H | H |
| 601. | Ethyl | Isobutyl | H | H | Isopropyl | H |
| 602. | Ethyl | Isobutyl | H | H | H | Isopropyl |
| 603. | Ethyl | Isobutyl | Methyl | Isopropyl | H | H |
| 604. | Ethyl | Isobutyl | Methyl | H | Isopropyl | H |
| 605. | Ethyl | Isobutyl | Methyl | H | H | Isopropyl |
| 606. | Ethyl | Isobutyl | H | Isopropyl | Methyl | H |
| 607. | Ethyl | Isobutyl | H | Isopropyl | Isopropyl | H |
| 608. | Ethyl | Isobutyl | H | Methyl | Isopropyl | H |
| 609. | Ethyl | Isobutyl | H | Isopropyl | Ethyl | H |
| 610. | Ethyl | Isobutyl | H | Ethyl | Isopropyl | H |
| 611. | Ethyl | Isobutyl | Isobutyl | H | H | H |
| 612. | Ethyl | Isobutyl | H | Isobutyl | H | H |
| 613. | Ethyl | Isobutyl | H | H | Isobutyl | H |
| 614. | Ethyl | Isobutyl | H | H | H | Isobutyl |
| 615. | Ethyl | Isobutyl | Methyl | Isobutyl | H | H |
| 616. | Ethyl | Isobutyl | Methyl | H | Isobutyl | H |
| 617. | Ethyl | Isobutyl | Methyl | H | H | Isobutyl |
| 618. | Ethyl | Isobutyl | H | Isobutyl | Methyl | H |
| 619. | Ethyl | Isobutyl | H | Isobutyl | Isobutyl | H |
| 620. | Ethyl | Isobutyl | H | Methyl | Isobutyl | H |
| 621. | Ethyl | Isobutyl | H | Isobutyl | Ethyl | H |
| 622. | Ethyl | Isobutyl | H | Ethyl | Isobutyl | H |
| 623. | Ethyl | Isobutyl | H | Isobutyl | Isopropyl | H |
| 624. | Ethyl | Isobutyl | H | Isopropyl | Isobutyl | H |
| 625. | Isopropyl | H | H | H | H | H |
| 626. | Isopropyl | H | Methyl | H | H | H |
| 627. | Isopropyl | H | H | Methyl | H | H |
| 628. | Isopropyl | H | H | H | Methyl | H |
| 629. | Isopropyl | H | H | H | H | Methyl |
| 630. | Isopropyl | H | Methyl | Methyl | H | H |
| 631. | Isopropyl | H | Methyl | H | Methyl | H |
| 632. | Isopropyl | H | Methyl | H | H | Methyl |
| 633. | Isopropyl | H | H | Methyl | Methyl | H |
| 634. | Isopropyl | H | H | Methyl | H | Methyl |
| 635. | Isopropyl | H | H | H | Methyl | Methyl |
| 636. | Isopropyl | H | Methyl | Methyl | Methyl | H |
| 637. | Isopropyl | H | Methyl | Methyl | H | Methyl |
| 638. | Isopropyl | H | Methyl | H | Methyl | Methyl |
| 639. | Isopropyl | H | H | Methyl | Methyl | Methyl |
| 640. | Isopropyl | H | Methyl | Methyl | Methyl | Methyl |
| 641. | Isopropyl | H | Ethyl | H | H | H |
| 642. | Isopropyl | H | H | Ethyl | H | H |
| 643. | Isopropyl | H | H | H | Ethyl | H |
| 644. | Isopropyl | H | H | H | H | Ethyl |
| 645. | Isopropyl | H | Methyl | Ethyl | H | H |
| 646. | Isopropyl | H | Methyl | H | Ethyl | H |
| 647. | Isopropyl | H | Methyl | H | H | Ethyl |
| 648. | Isopropyl | H | H | Ethyl | Methyl | H |
| 649. | Isopropyl | H | H | Ethyl | Ethyl | H |
| 650. | Isopropyl | H | H | Methyl | Ethyl | H |
| 651. | Isopropyl | H | Isopropyl | H | H | H |
| 652. | Isopropyl | H | H | Isopropyl | H | H |
| 653. | Isopropyl | H | H | H | Isopropyl | H |
| 654. | Isopropyl | H | H | H | H | Isopropyl |
| 655. | Isopropyl | H | Methyl | Isopropyl | H | H |
| 656. | Isopropyl | H | Methyl | H | Isopropyl | H |
| 657. | Isopropyl | H | Methyl | H | H | Isopropyl |
| 658. | Isopropyl | H | H | Isopropyl | Methyl | H |
| 659. | Isopropyl | H | H | Isopropyl | Isopropyl | H |

TABLE 1-continued

| Compound # | R₁ | R₂ | R₃ | R₄ | R₅ | R₆ |
|---|---|---|---|---|---|---|
| 660. | Isopropyl | H | H | Methyl | Isopropyl | H |
| 661. | Isopropyl | H | H | Isopropyl | Ethyl | H |
| 662. | Isopropyl | H | H | Ethyl | Isopropyl | H |
| 663. | Isopropyl | H | Isobutyl | H | H | H |
| 664. | Isopropyl | H | H | Isobutyl | H | H |
| 665. | Isopropyl | H | H | H | Isobutyl | H |
| 666. | Isopropyl | H | H | H | H | Isobutyl |
| 667. | Isopropyl | H | Methyl | Isobutyl | H | H |
| 668. | Isopropyl | H | Methyl | H | Isobutyl | H |
| 669. | Isopropyl | H | Methyl | H | H | Isobutyl |
| 670. | Isopropyl | H | H | Isobutyl | Methyl | H |
| 671. | Isopropyl | H | H | Isobutyl | Isobutyl | H |
| 672. | Isopropyl | H | H | Methyl | Isobutyl | H |
| 673. | Isopropyl | H | H | Isobutyl | Ethyl | H |
| 674. | Isopropyl | H | H | Ethyl | Isobutyl | H |
| 675. | Isopropyl | H | H | Isobutyl | Isopropyl | H |
| 676. | Isopropyl | H | H | Isopropyl | Isobutyl | H |
| 677. | Isopropyl | Methyl | H | H | H | H |
| 678. | Isopropyl | Methyl | Methyl | H | H | H |
| 679. | Isopropyl | Methyl | H | Methyl | H | H |
| 680. | Isopropyl | Methyl | H | H | Methyl | H |
| 681. | Isopropyl | Methyl | H | H | H | Methyl |
| 682. | Isopropyl | Methyl | Methyl | Methyl | H | H |
| 683. | Isopropyl | Methyl | Methyl | H | Methyl | H |
| 684. | Isopropyl | Methyl | Methyl | H | H | Methyl |
| 685. | Isopropyl | Methyl | H | Methyl | Methyl | H |
| 686. | Isopropyl | Methyl | H | Methyl | H | Methyl |
| 687. | Isopropyl | Methyl | H | H | Methyl | Methyl |
| 688. | Isopropyl | Methyl | Methyl | Methyl | Methyl | H |
| 689. | Isopropyl | Methyl | Methyl | Methyl | H | Methyl |
| 690. | Isopropyl | Methyl | Methyl | H | Methyl | Methyl |
| 691. | Isopropyl | Methyl | H | Methyl | Methyl | Methyl |
| 692. | Isopropyl | Methyl | Methyl | Methyl | Methyl | Methyl |
| 693. | Isopropyl | Methyl | Ethyl | H | H | H |
| 694. | Isopropyl | Methyl | H | Ethyl | H | H |
| 695. | Isopropyl | Methyl | H | H | Ethyl | H |
| 696. | Isopropyl | Methyl | H | H | H | Ethyl |
| 697. | Isopropyl | Methyl | Methyl | Ethyl | H | H |
| 698. | Isopropyl | Methyl | Methyl | H | Ethyl | H |
| 699. | Isopropyl | Methyl | Methyl | H | H | Ethyl |
| 700. | Isopropyl | Methyl | H | Ethyl | Methyl | H |
| 701. | Isopropyl | Methyl | H | Ethyl | Ethyl | H |
| 702. | Isopropyl | Methyl | H | Methyl | Ethyl | H |
| 703. | Isopropyl | Methyl | Isopropyl | H | H | H |
| 704. | Isopropyl | Methyl | H | Isopropyl | H | H |
| 705. | Isopropyl | Methyl | H | H | Isopropyl | H |
| 706. | Isopropyl | Methyl | H | H | H | Isopropyl |
| 707. | Isopropyl | Methyl | Methyl | Isopropyl | H | H |
| 708. | Isopropyl | Methyl | Methyl | H | Isopropyl | H |
| 709. | Isopropyl | Methyl | Methyl | H | H | Isopropyl |
| 710. | Isopropyl | Methyl | H | Isopropyl | Methyl | H |
| 711. | Isopropyl | Methyl | H | Isopropyl | Isopropyl | H |
| 712. | Isopropyl | Methyl | H | Methyl | Isopropyl | H |
| 713. | Isopropyl | Methyl | H | Isopropyl | Ethyl | H |
| 714. | Isopropyl | Methyl | H | Ethyl | Isopropyl | H |
| 715. | Isopropyl | Methyl | Isobutyl | H | H | H |
| 716. | Isopropyl | Methyl | H | Isobutyl | H | H |
| 717. | Isopropyl | Methyl | H | H | Isobutyl | H |
| 718. | Isopropyl | Methyl | H | H | H | Isobutyl |
| 719. | Isopropyl | Methyl | Methyl | Isobutyl | H | H |
| 720. | Isopropyl | Methyl | Methyl | H | Isobutyl | H |
| 721. | Isopropyl | Methyl | Methyl | H | H | Isobutyl |
| 722. | Isopropyl | Methyl | H | Isobutyl | Methyl | H |
| 723. | Isopropyl | Methyl | H | Isobutyl | Isobutyl | H |
| 724. | Isopropyl | Methyl | H | Methyl | Isobutyl | H |
| 725. | Isopropyl | Methyl | H | Isobutyl | Ethyl | H |
| 726. | Isopropyl | Methyl | H | Ethyl | Isobutyl | H |
| 727. | Isopropyl | Methyl | H | Isobutyl | Isopropyl | H |
| 728. | Isopropyl | Methyl | H | Isopropyl | Isobutyl | H |
| 729. | Isopropyl | Ethyl | H | H | H | H |
| 730. | Isopropyl | Ethyl | Methyl | H | H | H |
| 731. | Isopropyl | Ethyl | H | Methyl | H | H |
| 732. | Isopropyl | Ethyl | H | H | Methyl | H |
| 733. | Isopropyl | Ethyl | H | H | H | Methyl |
| 734. | Isopropyl | Ethyl | Methyl | Methyl | H | H |
| 735. | Isopropyl | Ethyl | Methyl | H | Methyl | H |
| 736. | Isopropyl | Ethyl | Methyl | H | H | Methyl |
| 737. | Isopropyl | Ethyl | H | Methyl | Methyl | H |

TABLE 1-continued

| Compound # | $R_1$ | $R_2$ | $R_3$ | $R_4$ | $R_5$ | $R_6$ |
|---|---|---|---|---|---|---|
| 738. | Isopropyl | Ethyl | H | Methyl | H | Methyl |
| 739. | Isopropyl | Ethyl | H | H | Methyl | Methyl |
| 740. | Isopropyl | Ethyl | Methyl | Methyl | Methyl | H |
| 741. | Isopropyl | Ethyl | Methyl | Methyl | H | Methyl |
| 742. | Isopropyl | Ethyl | Methyl | H | Methyl | Methyl |
| 743. | Isopropyl | Ethyl | H | Methyl | Methyl | Methyl |
| 744. | Isopropyl | Ethyl | Methyl | Methyl | Methyl | Methyl |
| 745. | Isopropyl | Ethyl | Ethyl | H | H | H |
| 746. | Isopropyl | Ethyl | H | Ethyl | H | H |
| 747. | Isopropyl | Ethyl | H | H | Ethyl | H |
| 748. | Isopropyl | Ethyl | H | H | H | Ethyl |
| 749. | Isopropyl | Ethyl | Methyl | Ethyl | H | H |
| 750. | Isopropyl | Ethyl | Methyl | H | Ethyl | H |
| 751. | Isopropyl | Ethyl | Methyl | H | H | Ethyl |
| 752. | Isopropyl | Ethyl | H | Ethyl | Methyl | H |
| 753. | Isopropyl | Ethyl | H | Ethyl | Ethyl | H |
| 754. | Isopropyl | Ethyl | H | Methyl | Ethyl | H |
| 755. | Isopropyl | Ethyl | Isopropyl | H | H | H |
| 756. | Isopropyl | Ethyl | H | Isopropyl | H | H |
| 757. | Isopropyl | Ethyl | H | H | Isopropyl | H |
| 758. | Isopropyl | Ethyl | H | H | H | Isopropyl |
| 759. | Isopropyl | Ethyl | Methyl | Isopropyl | H | H |
| 760. | Isopropyl | Ethyl | Methyl | H | Isopropyl | H |
| 761. | Isopropyl | Ethyl | Methyl | H | H | Isopropyl |
| 762. | Isopropyl | Ethyl | H | Isopropyl | Methyl | H |
| 763. | Isopropyl | Ethyl | H | Isopropyl | Isopropyl | H |
| 764. | Isopropyl | Ethyl | H | Methyl | Isopropyl | H |
| 765. | Isopropyl | Ethyl | H | Isopropyl | Ethyl | H |
| 766. | Isopropyl | Ethyl | H | Ethyl | Isopropyl | H |
| 767. | Isopropyl | Ethyl | Isobutyl | H | H | H |
| 768. | Isopropyl | Ethyl | H | Isobutyl | H | H |
| 769. | Isopropyl | Ethyl | H | H | Isobutyl | H |
| 770. | Isopropyl | Ethyl | H | H | H | Isobutyl |
| 771. | Isopropyl | Ethyl | Methyl | Isobutyl | H | H |
| 772. | Isopropyl | Ethyl | Methyl | H | Isobutyl | H |
| 773. | Isopropyl | Ethyl | Methyl | H | H | Isobutyl |
| 774. | Isopropyl | Ethyl | H | Isobutyl | Methyl | H |
| 775. | Isopropyl | Ethyl | H | Isobutyl | Isobutyl | H |
| 776. | Isopropyl | Ethyl | H | Methyl | Isobutyl | H |
| 777. | Isopropyl | Ethyl | H | Isobutyl | Ethyl | H |
| 778. | Isopropyl | Ethyl | H | Ethyl | Isobutyl | H |
| 779. | Isopropyl | Ethyl | H | Isobutyl | Isopropyl | H |
| 780. | Isopropyl | Ethyl | H | Isopropyl | Isobutyl | H |
| 781. | Isopropyl | Isopropyl | H | H | H | H |
| 782. | Isopropyl | Isopropyl | Methyl | H | H | H |
| 783. | Isopropyl | Isopropyl | H | Methyl | H | H |
| 784. | Isopropyl | Isopropyl | H | H | Methyl | H |
| 785. | Isopropyl | Isopropyl | H | H | H | Methyl |
| 786. | Isopropyl | Isopropyl | Methyl | Methyl | H | H |
| 787. | Isopropyl | Isopropyl | Methyl | H | Methyl | H |
| 788. | Isopropyl | Isopropyl | Methyl | H | H | Methyl |
| 789. | Isopropyl | Isopropyl | H | Methyl | Methyl | H |
| 790. | Isopropyl | Isopropyl | H | Methyl | H | Methyl |
| 791. | Isopropyl | Isopropyl | H | H | Methyl | Methyl |
| 792. | Isopropyl | Isopropyl | Methyl | Methyl | Methyl | H |
| 793. | Isopropyl | Isopropyl | Methyl | Methyl | H | Methyl |
| 794. | Isopropyl | Isopropyl | Methyl | H | Methyl | Methyl |
| 795. | Isopropyl | Isopropyl | H | Methyl | Methyl | Methyl |
| 796. | Isopropyl | Isopropyl | Methyl | Methyl | Methyl | Methyl |
| 797. | Isopropyl | Isopropyl | Ethyl | H | H | H |
| 798. | Isopropyl | Isopropyl | H | Ethyl | H | H |
| 799. | Isopropyl | Isopropyl | H | H | Ethyl | H |
| 800. | Isopropyl | Isopropyl | H | H | H | Ethyl |
| 801. | Isopropyl | Isopropyl | Methyl | Ethyl | H | H |
| 802. | Isopropyl | Isopropyl | Methyl | H | Ethyl | H |
| 803. | Isopropyl | Isopropyl | Methyl | H | H | Ethyl |
| 804. | Isopropyl | Isopropyl | H | Ethyl | Methyl | H |
| 805. | Isopropyl | Isopropyl | H | Ethyl | Ethyl | H |
| 806. | Isopropyl | Isopropyl | H | Methyl | Ethyl | H |
| 807. | Isopropyl | Isopropyl | Isopropyl | H | H | H |
| 808. | Isopropyl | Isopropyl | H | Isopropyl | H | H |
| 809. | Isopropyl | Isopropyl | H | H | Isopropyl | H |
| 810. | Isopropyl | Isopropyl | H | H | H | Isopropyl |
| 811. | Isopropyl | Isopropyl | Methyl | Isopropyl | H | H |
| 812. | Isopropyl | Isopropyl | Methyl | H | Isopropyl | H |
| 813. | Isopropyl | Isopropyl | Methyl | H | H | Isopropyl |
| 814. | Isopropyl | Isopropyl | H | Isopropyl | Methyl | H |
| 815. | Isopropyl | Isopropyl | H | Isopropyl | Isopropyl | H |

TABLE 1-continued

| Compound # | R$_1$ | R$_2$ | R$_3$ | R$_4$ | R$_5$ | R$_6$ |
| --- | --- | --- | --- | --- | --- | --- |
| 816. | Isopropyl | Isopropyl | H | Methyl | Isopropyl | H |
| 817. | Isopropyl | Isopropyl | H | Isopropyl | Ethyl | H |
| 818. | Isopropyl | Isopropyl | H | Ethyl | Isopropyl | H |
| 819. | Isopropyl | Isopropyl | Isobutyl | H | H | H |
| 820. | Isopropyl | Isopropyl | H | Isobutyl | H | H |
| 821. | Isopropyl | Isopropyl | H | H | Isobutyl | H |
| 822. | Isopropyl | Isopropyl | H | H | H | Isobutyl |
| 823. | Isopropyl | Isopropyl | Methyl | Isobutyl | H | H |
| 824. | Isopropyl | Isopropyl | Methyl | H | Isobutyl | H |
| 825. | Isopropyl | Isopropyl | Methyl | H | H | Isobutyl |
| 826. | Isopropyl | Isopropyl | H | Isobutyl | Methyl | H |
| 827. | Isopropyl | Isopropyl | H | Isobutyl | Isobutyl | H |
| 828. | Isopropyl | Isopropyl | H | Methyl | Isobutyl | H |
| 829. | Isopropyl | Isopropyl | H | Isobutyl | Ethyl | H |
| 830. | Isopropyl | Isopropyl | H | Ethyl | Isobutyl | H |
| 831. | Isopropyl | Isopropyl | H | Isobutyl | Isopropyl | H |
| 832. | Isopropyl | Isopropyl | H | Isopropyl | Isobutyl | H |
| 833. | Isopropyl | Isobutyl | H | H | H | H |
| 834. | Isopropyl | Isobutyl | Methyl | H | H | H |
| 835. | Isopropyl | Isobutyl | H | Methyl | H | H |
| 836. | Isopropyl | Isobutyl | H | H | Methyl | H |
| 837. | Isopropyl | Isobutyl | H | H | H | Methyl |
| 838. | Isopropyl | Isobutyl | Methyl | Methyl | H | H |
| 839. | Isopropyl | Isobutyl | Methyl | H | Methyl | H |
| 840. | Isopropyl | Isobutyl | Methyl | H | H | Methyl |
| 841. | Isopropyl | Isobutyl | H | Methyl | Methyl | H |
| 842. | Isopropyl | Isobutyl | H | Methyl | H | Methyl |
| 843. | Isopropyl | Isobutyl | H | H | Methyl | Methyl |
| 844. | Isopropyl | Isobutyl | Methyl | Methyl | Methyl | H |
| 845. | Isopropyl | Isobutyl | Methyl | Methyl | H | Methyl |
| 846. | Isopropyl | Isobutyl | Methyl | H | Methyl | Methyl |
| 847. | Isopropyl | Isobutyl | H | Methyl | Methyl | Methyl |
| 848. | Isopropyl | Isobutyl | Methyl | Methyl | Methyl | Methyl |
| 849. | Isopropyl | Isobutyl | Ethyl | H | H | H |
| 850. | Isopropyl | Isobutyl | H | Ethyl | H | H |
| 851. | Isopropyl | Isobutyl | H | H | Ethyl | H |
| 852. | Isopropyl | Isobutyl | H | H | H | Ethyl |
| 853. | Isopropyl | Isobutyl | Methyl | Ethyl | H | H |
| 854. | Isopropyl | Isobutyl | Methyl | H | Ethyl | H |
| 855. | Isopropyl | Isobutyl | Methyl | H | H | Ethyl |
| 856. | Isopropyl | Isobutyl | H | Ethyl | Methyl | H |
| 857. | Isopropyl | Isobutyl | H | Ethyl | Ethyl | H |
| 858. | Isopropyl | Isobutyl | H | Methyl | Ethyl | H |
| 859. | Isopropyl | Isobutyl | Isopropyl | H | H | H |
| 860. | Isopropyl | Isobutyl | H | Isopropyl | H | H |
| 861. | Isopropyl | Isobutyl | H | H | Isopropyl | H |
| 862. | Isopropyl | Isobutyl | H | H | H | Isopropyl |
| 863. | Isopropyl | Isobutyl | Methyl | Isopropyl | H | H |
| 864. | Isopropyl | Isobutyl | Methyl | H | Isopropyl | H |
| 865. | Isopropyl | Isobutyl | Methyl | H | H | Isopropyl |
| 866. | Isopropyl | Isobutyl | H | Isopropyl | Methyl | H |
| 867. | Isopropyl | Isobutyl | H | Isopropyl | Isopropyl | H |
| 868. | Isopropyl | Isobutyl | H | Methyl | Isopropyl | H |
| 869. | Isopropyl | Isobutyl | H | Isopropyl | Ethyl | H |
| 870. | Isopropyl | Isobutyl | H | Ethyl | Isopropyl | H |
| 871. | Isopropyl | Isobutyl | Isobutyl | H | H | H |
| 872. | Isopropyl | Isobutyl | H | Isobutyl | H | H |
| 873. | Isopropyl | Isobutyl | H | H | Isobutyl | H |
| 874. | Isopropyl | Isobutyl | H | H | H | Isobutyl |
| 875. | Isopropyl | Isobutyl | Methyl | Isobutyl | H | H |
| 876. | Isopropyl | Isobutyl | Methyl | H | Isobutyl | H |
| 877. | Isopropyl | Isobutyl | Methyl | H | H | Isobutyl |
| 878. | Isopropyl | Isobutyl | H | Isobutyl | Methyl | H |
| 879. | Isopropyl | Isobutyl | H | Isobutyl | Isobutyl | H |
| 880. | Isopropyl | Isobutyl | H | Methyl | Isobutyl | H |
| 881. | Isopropyl | Isobutyl | H | Isobutyl | Ethyl | H |
| 882. | Isopropyl | Isobutyl | H | Ethyl | Isobutyl | H |
| 883. | Isopropyl | Isobutyl | H | Isobutyl | Isopropyl | H |
| 884. | Isopropyl | Isobutyl | H | Isopropyl | Isobutyl | H |
| 885. | Isobutyl | H | H | H | H | H |
| 886. | Isobutyl | H | Methyl | H | H | H |
| 887. | Isobutyl | H | H | Methyl | H | H |
| 888. | Isobutyl | H | H | H | Methyl | H |
| 889. | Isobutyl | H | H | H | H | Methyl |
| 890. | Isobutyl | H | Methyl | Methyl | H | H |
| 891. | Isobutyl | H | Methyl | H | Methyl | H |
| 892. | Isobutyl | H | Methyl | H | H | Methyl |
| 893. | Isobutyl | H | H | Methyl | Methyl | H |

TABLE 1-continued

| Compound # | R₁ | R₂ | R₃ | R₄ | R₅ | R₆ |
|---|---|---|---|---|---|---|
| 894. | Isobutyl | H | H | Methyl | H | Methyl |
| 895. | Isobutyl | H | H | H | Methyl | Methyl |
| 896. | Isobutyl | H | Methyl | Methyl | Methyl | H |
| 897. | Isobutyl | H | Methyl | Methyl | H | Methyl |
| 898. | Isobutyl | H | Methyl | H | Methyl | Methyl |
| 899. | Isobutyl | H | H | Methyl | Methyl | Methyl |
| 900. | Isobutyl | H | Methyl | Methyl | Methyl | Methyl |
| 901. | Isobutyl | H | Ethyl | H | H | H |
| 902. | Isobutyl | H | H | Ethyl | H | H |
| 903. | Isobutyl | H | H | H | Ethyl | H |
| 904. | Isobutyl | H | H | H | H | Ethyl |
| 905. | Isobutyl | H | Methyl | Ethyl | H | H |
| 906. | Isobutyl | H | Methyl | H | Ethyl | H |
| 907. | Isobutyl | H | Methyl | H | H | Ethyl |
| 908. | Isobutyl | H | H | Ethyl | Methyl | H |
| 909. | Isobutyl | H | H | Ethyl | Ethyl | H |
| 910. | Isobutyl | H | H | Methyl | Ethyl | H |
| 911. | Isobutyl | H | Isopropyl | H | H | H |
| 912. | Isobutyl | H | H | Isopropyl | H | H |
| 913. | Isobutyl | H | H | H | Isopropyl | H |
| 914. | Isobutyl | H | H | H | H | Isopropyl |
| 915. | Isobutyl | H | Methyl | Isopropyl | H | H |
| 916. | Isobutyl | H | Methyl | H | Isopropyl | H |
| 917. | Isobutyl | H | Methyl | H | H | Isopropyl |
| 918. | Isobutyl | H | H | Isopropyl | Methyl | H |
| 919. | Isobutyl | H | H | Isopropyl | Isopropyl | H |
| 920. | Isobutyl | H | H | Methyl | Isopropyl | H |
| 921. | Isobutyl | H | H | Isopropyl | Ethyl | H |
| 922. | Isobutyl | H | H | Ethyl | Isopropyl | H |
| 923. | Isobutyl | H | Isobutyl | H | H | H |
| 924. | Isobutyl | H | H | Isobutyl | H | H |
| 925. | Isobutyl | H | H | H | Isobutyl | H |
| 926. | Isobutyl | H | H | H | H | Isobutyl |
| 927. | Isobutyl | H | Methyl | Isobutyl | H | H |
| 928. | Isobutyl | H | Methyl | H | Isobutyl | H |
| 929. | Isobutyl | H | Methyl | H | H | Isobutyl |
| 930. | Isobutyl | H | H | Isobutyl | Methyl | H |
| 931. | Isobutyl | H | H | Isobutyl | Isobutyl | H |
| 932. | Isobutyl | H | H | Methyl | Isobutyl | H |
| 933. | Isobutyl | H | H | Isobutyl | Ethyl | H |
| 934. | Isobutyl | H | H | Ethyl | Isobutyl | H |
| 935. | Isobutyl | H | H | Isobutyl | Isopropyl | H |
| 936. | Isobutyl | H | H | Isopropyl | Isobutyl | H |
| 937. | Isobutyl | Methyl | H | H | H | H |
| 938. | Isobutyl | Methyl | Methyl | H | H | H |
| 939. | Isobutyl | Methyl | H | Methyl | H | H |
| 940. | Isobutyl | Methyl | H | H | Methyl | H |
| 941. | Isobutyl | Methyl | H | H | H | Methyl |
| 942. | Isobutyl | Methyl | Methyl | Methyl | H | H |
| 943. | Isobutyl | Methyl | Methyl | H | Methyl | H |
| 944. | Isobutyl | Methyl | Methyl | H | H | Methyl |
| 945. | Isobutyl | Methyl | H | Methyl | Methyl | H |
| 946. | Isobutyl | Methyl | H | Methyl | H | Methyl |
| 947. | Isobutyl | Methyl | H | H | Methyl | Methyl |
| 948. | Isobutyl | Methyl | Methyl | Methyl | Methyl | H |
| 949. | Isobutyl | Methyl | Methyl | Methyl | H | Methyl |
| 950. | Isobutyl | Methyl | Methyl | H | Methyl | Methyl |
| 951. | Isobutyl | Methyl | H | Methyl | Methyl | Methyl |
| 952. | Isobutyl | Methyl | Methyl | Methyl | Methyl | Methyl |
| 953. | Isobutyl | Methyl | Ethyl | H | H | H |
| 954. | Isobutyl | Methyl | H | Ethyl | H | H |
| 955. | Isobutyl | Methyl | H | H | Ethyl | H |
| 956. | Isobutyl | Methyl | H | H | H | Ethyl |
| 957. | Isobutyl | Methyl | Methyl | Ethyl | H | H |
| 958. | Isobutyl | Methyl | Methyl | H | Ethyl | H |
| 959. | Isobutyl | Methyl | Methyl | H | H | Ethyl |
| 960. | Isobutyl | Methyl | H | Ethyl | Methyl | H |
| 961. | Isobutyl | Methyl | H | Ethyl | Ethyl | H |
| 962. | Isobutyl | Methyl | H | Methyl | Ethyl | H |
| 963. | Isobutyl | Methyl | Isopropyl | H | H | H |
| 964. | Isobutyl | Methyl | H | Isopropyl | H | H |
| 965. | Isobutyl | Methyl | H | H | Isopropyl | H |
| 966. | Isobutyl | Methyl | H | H | H | Isopropyl |
| 967. | Isobutyl | Methyl | Methyl | Isopropyl | H | H |
| 968. | Isobutyl | Methyl | Methyl | H | Isopropyl | H |
| 969. | Isobutyl | Methyl | Methyl | H | H | Isopropyl |
| 970. | Isobutyl | Methyl | H | Isopropyl | Methyl | H |
| 971. | Isobutyl | Methyl | H | Isopropyl | Isopropyl | H |

TABLE 1-continued

| Compound # | R₁ | R₂ | R₃ | R₄ | R₅ | R₆ |
|---|---|---|---|---|---|---|
| 972. | Isobutyl | Methyl | H | Methyl | Isopropyl | H |
| 973. | Isobutyl | Methyl | H | Isopropyl | Ethyl | H |
| 974. | Isobutyl | Methyl | H | Ethyl | Isopropyl | H |
| 975. | Isobutyl | Methyl | Isobutyl | H | H | H |
| 976. | Isobutyl | Methyl | H | Isobutyl | H | H |
| 977. | Isobutyl | Methyl | H | H | Isobutyl | H |
| 978. | Isobutyl | Methyl | H | H | H | Isobutyl |
| 979. | Isobutyl | Methyl | Methyl | Isobutyl | H | H |
| 980. | Isobutyl | Methyl | Methyl | H | Isobutyl | H |
| 981. | Isobutyl | Methyl | Methyl | H | H | Isobutyl |
| 982. | Isobutyl | Methyl | H | Isobutyl | Methyl | H |
| 983. | Isobutyl | Methyl | H | Isobutyl | Isobutyl | H |
| 984. | Isobutyl | Methyl | H | Methyl | Isobutyl | H |
| 985. | Isobutyl | Methyl | H | Isobutyl | Ethyl | H |
| 986. | Isobutyl | Methyl | H | Ethyl | Isobutyl | H |
| 987. | Isobutyl | Methyl | H | Isobutyl | Isopropyl | H |
| 988. | Isobutyl | Methyl | H | Isopropyl | Isobutyl | H |
| 989. | Isobutyl | Ethyl | H | H | H | H |
| 990. | Isobutyl | Ethyl | Methyl | H | H | H |
| 991. | Isobutyl | Ethyl | H | Methyl | H | H |
| 992. | Isobutyl | Ethyl | H | H | Methyl | H |
| 993. | Isobutyl | Ethyl | H | H | H | Methyl |
| 994. | Isobutyl | Ethyl | Methyl | Methyl | H | H |
| 995. | Isobutyl | Ethyl | Methyl | H | Methyl | H |
| 996. | Isobutyl | Ethyl | Methyl | H | H | Methyl |
| 997. | Isobutyl | Ethyl | H | Methyl | Methyl | H |
| 998. | Isobutyl | Ethyl | H | Methyl | H | Methyl |
| 999. | Isobutyl | Ethyl | H | H | Methyl | Methyl |
| 1000. | Isobutyl | Ethyl | Methyl | Methyl | Methyl | H |
| 1001. | Isobutyl | Ethyl | Methyl | Methyl | H | Methyl |
| 1002. | Isobutyl | Ethyl | Methyl | H | Methyl | Methyl |
| 1003. | Isobutyl | Ethyl | H | Methyl | Methyl | Methyl |
| 1004. | Isobutyl | Ethyl | Methyl | Methyl | Methyl | Methyl |
| 1005. | Isobutyl | Ethyl | Ethyl | H | H | H |
| 1006. | Isobutyl | Ethyl | H | Ethyl | H | H |
| 1007. | Isobutyl | Ethyl | H | H | Ethyl | H |
| 1008. | Isobutyl | Ethyl | H | H | H | Ethyl |
| 1009. | Isobutyl | Ethyl | Methyl | Ethyl | H | H |
| 1010. | Isobutyl | Ethyl | Methyl | H | Ethyl | H |
| 1011. | Isobutyl | Ethyl | Methyl | H | H | Ethyl |
| 1012. | Isobutyl | Ethyl | H | Ethyl | Methyl | H |
| 1013. | Isobutyl | Ethyl | H | Ethyl | Ethyl | H |
| 1014. | Isobutyl | Ethyl | H | Methyl | Ethyl | H |
| 1015. | Isobutyl | Ethyl | Isopropyl | H | H | H |
| 1016. | Isobutyl | Ethyl | H | Isopropyl | H | H |
| 1017. | Isobutyl | Ethyl | H | H | Isopropyl | H |
| 1018. | Isobutyl | Ethyl | H | H | H | Isopropyl |
| 1019. | Isobutyl | Ethyl | Methyl | Isopropyl | H | H |
| 1020. | Isobutyl | Ethyl | Methyl | H | Isopropyl | H |
| 1021. | Isobutyl | Ethyl | Methyl | H | H | Isopropyl |
| 1022. | Isobutyl | Ethyl | H | Isopropyl | Methyl | H |
| 1023. | Isobutyl | Ethyl | H | Isopropyl | Isopropyl | H |
| 1024. | Isobutyl | Ethyl | H | Methyl | Isopropyl | H |
| 1025. | Isobutyl | Ethyl | H | Isopropyl | Ethyl | H |
| 1026. | Isobutyl | Ethyl | H | Ethyl | Isopropyl | H |
| 1027. | Isobutyl | Ethyl | Isobutyl | H | H | H |
| 1028. | Isobutyl | Ethyl | H | Isobutyl | H | H |
| 1029. | Isobutyl | Ethyl | H | H | Isobutyl | H |
| 1030. | Isobutyl | Ethyl | H | H | H | Isobutyl |
| 1031. | Isobutyl | Ethyl | Methyl | Isobutyl | H | H |
| 1032. | Isobutyl | Ethyl | Methyl | H | Isobutyl | H |
| 1033. | Isobutyl | Ethyl | Methyl | H | H | Isobutyl |
| 1034. | Isobutyl | Ethyl | H | Isobutyl | Methyl | H |
| 1035. | Isobutyl | Ethyl | H | Isobutyl | Isobutyl | H |
| 1036. | Isobutyl | Ethyl | H | Methyl | Isobutyl | H |
| 1037. | Isobutyl | Ethyl | H | Isobutyl | Ethyl | H |
| 1038. | Isobutyl | Ethyl | H | Ethyl | Isobutyl | H |
| 1039. | Isobutyl | Ethyl | H | Isobutyl | Isopropyl | H |
| 1040. | Isobutyl | Ethyl | H | Isopropyl | Isobutyl | H |
| 1041. | Isobutyl | Isopropyl | H | H | H | H |
| 1042. | Isobutyl | Isopropyl | Methyl | H | H | H |
| 1043. | Isobutyl | Isopropyl | H | Methyl | H | H |
| 1044. | Isobutyl | Isopropyl | H | H | Methyl | H |
| 1045. | Isobutyl | Isopropyl | H | H | H | Methyl |
| 1046. | Isobutyl | Isopropyl | Methyl | Methyl | H | H |
| 1047. | Isobutyl | Isopropyl | Methyl | H | Methyl | H |
| 1048. | Isobutyl | Isopropyl | Methyl | H | H | Methyl |
| 1049. | Isobutyl | Isopropyl | H | Methyl | Methyl | H |

TABLE 1-continued

| Compound # | R₁ | R₂ | R₃ | R₄ | R₅ | R₆ |
|---|---|---|---|---|---|---|
| 1050. | Isobutyl | Isopropyl | H | Methyl | H | Methyl |
| 1051. | Isobutyl | Isopropyl | H | H | Methyl | Methyl |
| 1052. | Isobutyl | Isopropyl | Methyl | Methyl | Methyl | H |
| 1053. | Isobutyl | Isopropyl | Methyl | Methyl | H | Methyl |
| 1054. | Isobutyl | Isopropyl | Methyl | H | Methyl | Methyl |
| 1055. | Isobutyl | Isopropyl | H | Methyl | Methyl | Methyl |
| 1056. | Isobutyl | Isopropyl | Methyl | Methyl | Methyl | Methyl |
| 1057. | Isobutyl | Isopropyl | Ethyl | H | H | H |
| 1058. | Isobutyl | Isopropyl | H | Ethyl | H | H |
| 1059. | Isobutyl | Isopropyl | H | H | Ethyl | H |
| 1060. | Isobutyl | Isopropyl | H | H | H | Ethyl |
| 1061. | Isobutyl | Isopropyl | Methyl | Ethyl | H | H |
| 1062. | Isobutyl | Isopropyl | Methyl | H | Ethyl | H |
| 1063. | Isobutyl | Isopropyl | Methyl | H | H | Ethyl |
| 1064. | Isobutyl | Isopropyl | H | Ethyl | Methyl | H |
| 1065. | Isobutyl | Isopropyl | H | Ethyl | Ethyl | H |
| 1066. | Isobutyl | Isopropyl | H | Methyl | Ethyl | H |
| 1067. | Isobutyl | Isopropyl | Isopropyl | H | H | H |
| 1068. | Isobutyl | Isopropyl | H | Isopropyl | H | H |
| 1069. | Isobutyl | Isopropyl | H | H | Isopropyl | H |
| 1070. | Isobutyl | Isopropyl | H | H | H | Isopropyl |
| 1071. | Isobutyl | Isopropyl | Methyl | Isopropyl | H | H |
| 1072. | Isobutyl | Isopropyl | Methyl | H | Isopropyl | H |
| 1073. | Isobutyl | Isopropyl | Methyl | H | H | Isopropyl |
| 1074. | Isobutyl | Isopropyl | H | Isopropyl | Methyl | H |
| 1075. | Isobutyl | Isopropyl | H | Isopropyl | Isopropyl | H |
| 1076. | Isobutyl | Isopropyl | H | Methyl | Isopropyl | H |
| 1077. | Isobutyl | Isopropyl | H | Isopropyl | Ethyl | H |
| 1078. | Isobutyl | Isopropyl | H | Ethyl | Isopropyl | H |
| 1079. | Isobutyl | Isopropyl | Isobutyl | H | H | H |
| 1080. | Isobutyl | Isopropyl | H | Isobutyl | H | H |
| 1081. | Isobutyl | Isopropyl | H | H | Isobutyl | H |
| 1082. | Isobutyl | Isopropyl | H | H | H | Isobutyl |
| 1083. | Isobutyl | Isopropyl | Methyl | Isobutyl | H | H |
| 1084. | Isobutyl | Isopropyl | Methyl | H | Isobutyl | H |
| 1085. | Isobutyl | Isopropyl | Methyl | H | H | Isobutyl |
| 1086. | Isobutyl | Isopropyl | H | Isobutyl | Methyl | H |
| 1087. | Isobutyl | Isopropyl | H | Isobutyl | Isobutyl | H |
| 1088. | Isobutyl | Isopropyl | H | Methyl | Isobutyl | H |
| 1089. | Isobutyl | Isopropyl | H | Isobutyl | Ethyl | H |
| 1090. | Isobutyl | Isopropyl | H | Ethyl | Isobutyl | H |
| 1091. | Isobutyl | Isopropyl | H | Isobutyl | Isopropyl | H |
| 1092. | Isobutyl | Isopropyl | H | Isopropyl | Isobutyl | H |
| 1093. | Isobutyl | Isobutyl | H | H | H | H |
| 1094. | Isobutyl | Isobutyl | Methyl | H | H | H |
| 1095. | Isobutyl | Isobutyl | H | Methyl | H | H |
| 1096. | Isobutyl | Isobutyl | H | H | Methyl | H |
| 1097. | Isobutyl | Isobutyl | H | H | H | Methyl |
| 1098. | Isobutyl | Isobutyl | Methyl | Methyl | H | H |
| 1099. | Isobutyl | Isobutyl | Methyl | H | Methyl | H |
| 1100. | Isobutyl | Isobutyl | Methyl | H | H | Methyl |
| 1101. | Isobutyl | Isobutyl | H | Methyl | Methyl | H |
| 1102. | Isobutyl | Isobutyl | H | Methyl | H | Methyl |
| 1103. | Isobutyl | Isobutyl | H | H | Methyl | Methyl |
| 1104. | Isobutyl | Isobutyl | Methyl | Methyl | Methyl | H |
| 1105. | Isobutyl | Isobutyl | Methyl | Methyl | H | Methyl |
| 1106. | Isobutyl | Isobutyl | Methyl | H | Methyl | Methyl |
| 1107. | Isobutyl | Isobutyl | H | Methyl | Methyl | Methyl |
| 1108. | Isobutyl | Isobutyl | Methyl | Methyl | Methyl | Methyl |
| 1109. | Isobutyl | Isobutyl | Ethyl | H | H | H |
| 1110. | Isobutyl | Isobutyl | H | Ethyl | H | H |
| 1111. | Isobutyl | Isobutyl | H | H | Ethyl | H |
| 1112. | Isobutyl | Isobutyl | H | H | H | Ethyl |
| 1113. | Isobutyl | Isobutyl | Methyl | Ethyl | H | H |
| 1114. | Isobutyl | Isobutyl | Methyl | H | Ethyl | H |
| 1115. | Isobutyl | Isobutyl | Methyl | H | H | Ethyl |
| 1116. | Isobutyl | Isobutyl | H | Ethyl | Methyl | H |
| 1117. | Isobutyl | Isobutyl | H | Ethyl | Ethyl | H |
| 1118. | Isobutyl | Isobutyl | H | Methyl | Ethyl | H |
| 1119. | Isobutyl | Isobutyl | Isopropyl | H | H | H |
| 1120. | Isobutyl | Isobutyl | H | Isopropyl | H | H |
| 1121. | Isobutyl | Isobutyl | H | H | Isopropyl | H |
| 1122. | Isobutyl | Isobutyl | H | H | H | Isopropyl |
| 1123. | Isobutyl | Isobutyl | Methyl | Isopropyl | H | H |
| 1124. | Isobutyl | Isobutyl | Methyl | H | Isopropyl | H |
| 1125. | Isobutyl | Isobutyl | Methyl | H | H | Isopropyl |
| 1126. | Isobutyl | Isobutyl | H | Isopropyl | Methyl | H |
| 1127. | Isobutyl | Isobutyl | H | Isopropyl | Isopropyl | H |

TABLE 1-continued

| Compound # | $R_1$ | $R_2$ | $R_3$ | $R_4$ | $R_5$ | $R_6$ |
|---|---|---|---|---|---|---|
| 1128. | Isobutyl | Isobutyl | H | Methyl | Isopropyl | H |
| 1129. | Isobutyl | Isobutyl | H | Isopropyl | Ethyl | H |
| 1130. | Isobutyl | Isobutyl | H | Ethyl | Isopropyl | H |
| 1131. | Isobutyl | Isobutyl | Isobutyl | H | H | H |
| 1132. | Isobutyl | Isobutyl | H | Isobutyl | H | H |
| 1133. | Isobutyl | Isobutyl | H | H | Isobutyl | H |
| 1134. | Isobutyl | Isobutyl | H | H | H | Isobutyl |
| 1135. | Isobutyl | Isobutyl | Methyl | Isobutyl | H | H |
| 1136. | Isobutyl | Isobutyl | Methyl | H | Isobutyl | H |
| 1137. | Isobutyl | Isobutyl | Methyl | H | H | Isobutyl |
| 1138. | Isobutyl | Isobutyl | H | Isobutyl | Methyl | H |
| 1139. | Isobutyl | Isobutyl | H | Isobutyl | Isobutyl | H |
| 1140. | Isobutyl | Isobutyl | H | Methyl | Isobutyl | H |
| 1141. | Isobutyl | Isobutyl | H | Isobutyl | Ethyl | H |
| 1142. | Isobutyl | Isobutyl | H | Ethyl | Isobutyl | H |
| 1143. | Isobutyl | Isobutyl | H | Isobutyl | Isopropyl | H |
| 1144. | Isobutyl | Isobutyl | H | Isopropyl | Isobutyl | H |
| 1145. | $CD_3CH_2$ | H | H | H | H | H |
| 1146. | $(CD_3)_2CH$ | H | H | H | H | H |

In one embodiment, a first device is provided. The first device comprises a first organic light emitting device, further comprising an anode, a cathode, and an organic layer, disposed between the anode and the cathode, comprising a compound having the formula:

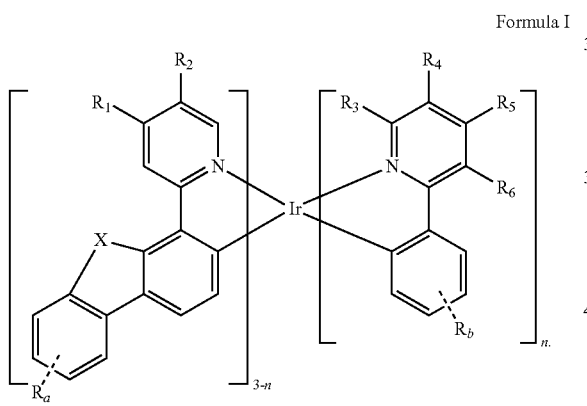

Formula I

Formula I. $R_1$ and $R_2$ are optionally linked and the sum of the number of carbon atoms in R1 and R2 is at least 2. $R_3$, $R_4$, $R_5$, $R_6$ are optionally linked, and $R_a$ and $R_b$ represent mono-, di-, tri- or tetra-substitution. X is selected from the group consisting of BR, NR, PR, O, S, Se, C=O, S=O, $SO_2$, CRR', SiRR', and GeRR', and $R_a$, $R_b$, R, $R_1$, $R_2$, $R_3$, $R_4$, $R_5$, and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is 1 or 2.

In one embodiment, the first device is a consumer product. In another embodiment, the first device is an organic light-emitting device. In another embodiment, the first device comprises a lighting panel. In one embodiment, the organic layer is an emissive layer and the compound is an emissive dopant. In another embodiment, the organic layer is an emissive layer and the compound is a non-emissive dopant.

In one embodiment, the organic layer further comprises a host. In another embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n}+_1$, C≡C$C_nH_{2n+1}$, $Ar_1$, $Ar_1$—$Ar_2$, $C_nH_{2n}$—$Ar_1$, or no substitution, wherein $Ar_1$ and $Ar_2$ are independently selected from the group consisting of benzene, biphenyl, naphthalene, triphenylene, carbazole, and heteroaromatic analogs thereof, and wherein n is from 1 to 10.

In one embodiment, the host has the formula

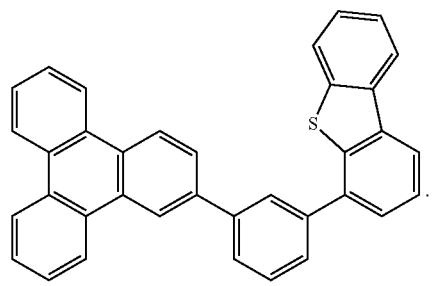 [SMILES: c1cc(-c2ccc3c4ccccc4c4ccccc4c3c2)cc(-c2cccc3c2sc2ccccc23)c1]

In another embodiment, the host is selected from the group consisting of:

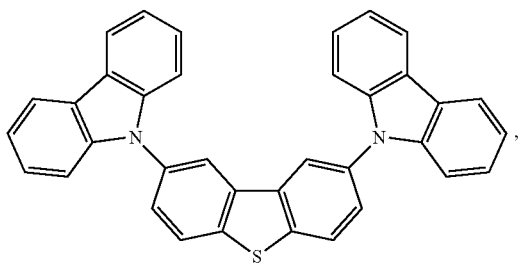

,

-continued

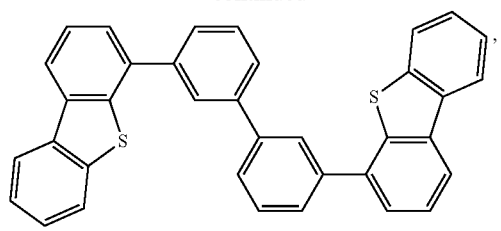

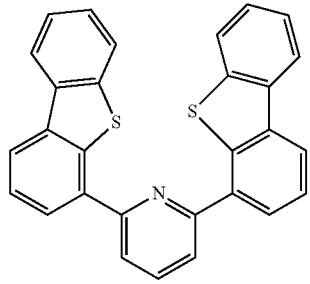

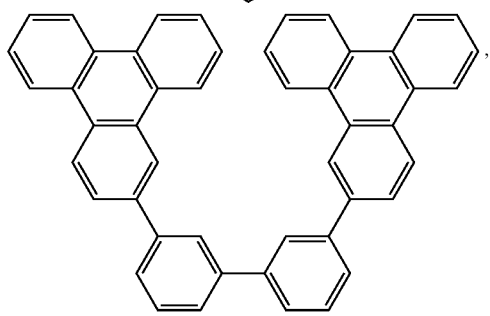

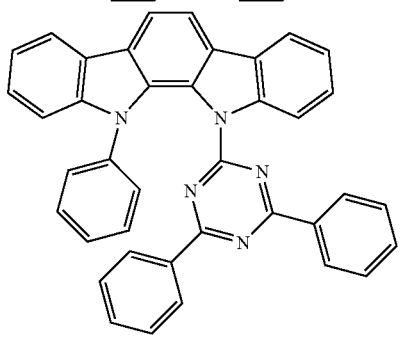

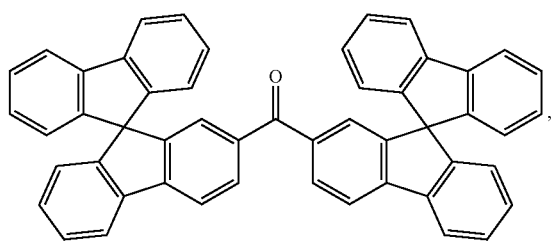

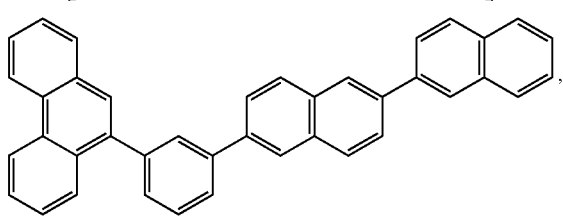

and combinations thereof.

In one embodiment, the host is a metal complex.

Device Examples

All example devices were fabricated by high vacuum (<10$^{-7}$ Torr) thermal evaporation (VTE). The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound C as the hole injection layer (HIL), 300 Å of 4,4'-bis[N-(1-naphthyl)-N-phenylamino]biphenyl (alpha-NPD) as the hole transporting layer (HTL), 300 Å of the invention compound doped in Compound D as host with 5-15 weight percent of a compound of Formula I as the emissive layer (EML), 50 Å of Compound D as blocking layer (BL), and 400 Å of Alq (tris-8-hydroxyquinoline aluminum) as the ETL. Comparative Examples with Compound A and Compound B were fabricated similarly to the Device Examples except that Compound A and Compound B were used as the emitter in the EML.

The device results and data are summarized in Tables 1 from those devices. As used herein, NPD, Alq, Compound A, Compound B, Compound C, and Compound D have the following structures:

Compound A

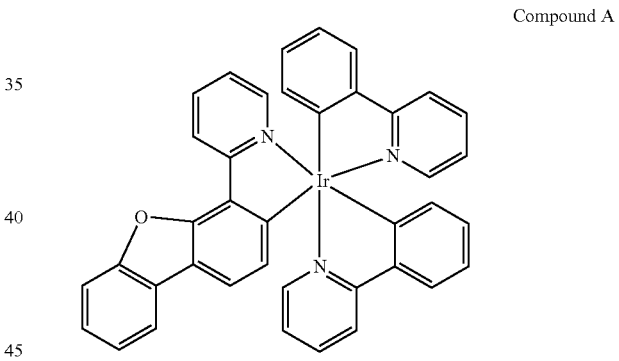

Compound B

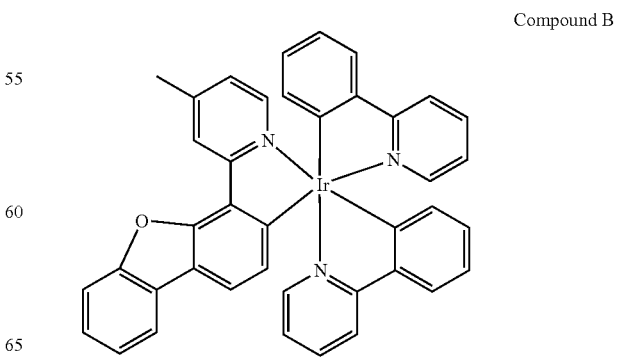

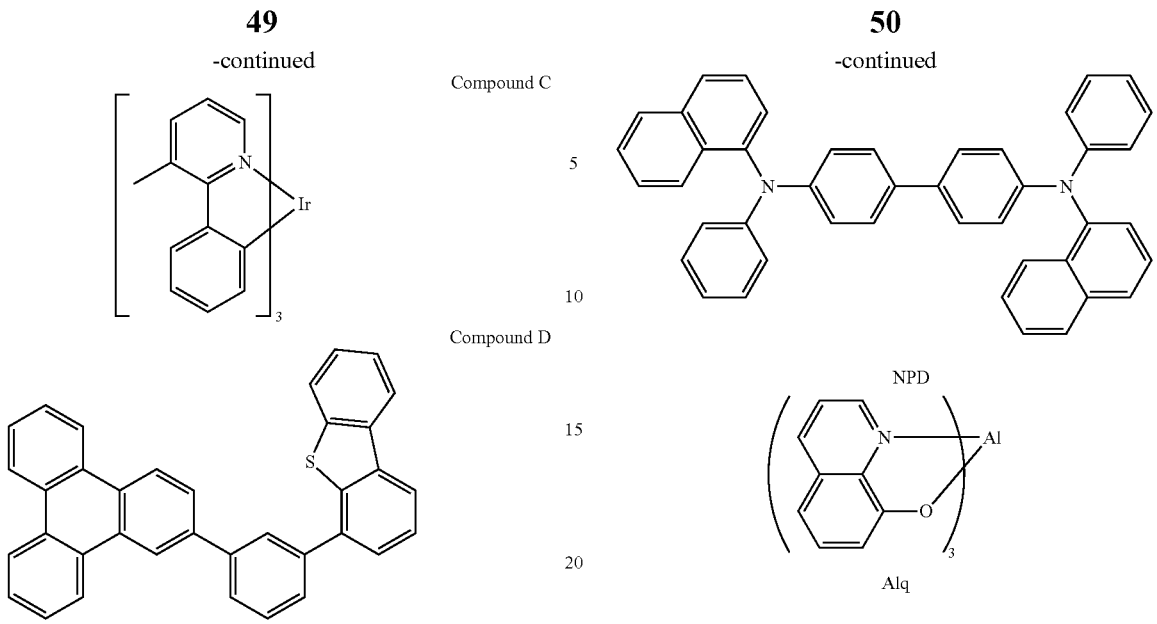

Compound C

Compound D

NPD

Alq

TABLE 2

| | | | VTE Phosphorescent OLEDs | | | |
|---|---|---|---|---|---|---|
| Example | HIL | HTL | EML (300 Å, doping %) | | BL | ETL 1 |
| Comparative Example 1 | Compound C 100 Å | NPD 300 Å | Compound D | Compound A 10% | Compound D 50 Å | Alq 400 Å |
| Comparative Example 2 | Compound C 100 Å | NPD 300 Å | Compound D | Compound B 10% | Compound D 50 Å | Alq 400 Å |
| Example 1 | Compound C 100 Å | NPD 300 Å | Compound D | Compound 53 12% | Compound D 50 Å | Alq 400 Å |
| Example 2 | Compound C 100 Å | NPD 300 Å | Compound D | Compound 157 10% | Compound D 50 Å | Alq 400 Å |
| Example 3 | Compound C 100 Å | NPD 300 Å | Compound D | Compound 158 12% | Compound D 50 Å | Alq 400 Å |
| Example 4 | Compound C 100 Å | NPD 300 Å | Compound D | Compound 159 10% | Compound D 50 Å | Alq 400 Å |
| Example 5 | Compound C 100 Å | NPD 300 Å | Compound D | Compound 165 12% | Compound D 50 Å | Alq 400 Å |
| Example 6 | Compound C 100 Å | NPD 300 Å | Compound D | Compound 174 8% | Compound D 50 Å | Alq 400 Å |
| Example 7 | Compound C 100 Å | NPD 300 Å | Compound D | Compound 175 8% | Compound D 50 Å | Alq 400 Å |
| Example 8 | Compound C 100 Å | NPD 300 Å | Compound D | Compound 184 7% | Compound D 50 Å | Alq 400 Å |
| Example 9 | Compound C 100 Å | NPD 300 Å | Compound D | Compound 185 10% | Compound D 50 Å | Alq 400 Å |
| Example 10 | Compound C 100 Å | NPD 300 Å | Compound D | Compound 314 12% | Compound D 50 Å | Alq 400 Å |
| Example 11 | Compound C 100 Å | NPD 300 Å | Compound D | Compound 321 12% | Compound D 50 Å | Alq 400 Å |
| Example 12 | Compound C 100 Å | NPD 300 Å | Compound D | Compound 625 12% | Compound D 50 Å | Alq 400 Å |
| Example 13 | Compound C 100 Å | NPD 300 Å | Compound D | Compound 626 10% | Compound D 50 Å | Alq 400 Å |
| Example 14 | Compound C 100 Å | NPD 300 Å | Compound D | Compound 627 8% | Compound D 50 Å | Alq 400 Å |
| Example 15 | Compound C 100 Å | NPD 300 Å | Compound D | Compound 628 8% | Compound D 50 Å | Alq 400 Å |
| Example 16 | Compound C 100 Å | NPD 300 Å | Compound D | Compound 633 10% | Compound D 50 Å | Alq 400 Å |
| Example 17 | Compound C 100 Å | NPD 300 Å | Compound D | Compound 643 8% | Compound D 50 Å | Alq 400 Å |
| Example 18 | Compound C 100 Å | NPD 300 Å | Compound D | Compound 652 8% | Compound D 50 Å | Alq 400 Å |
| Example 19 | Compound C 100 Å | NPD 300 Å | Compound D | Compound 653 8% | Compound D 50 Å | Alq 400 Å |
| Example 20 | Compound C 100 Å | NPD 300 Å | Compound D | Compound 1145 10% | Compound D 50 Å | Alq 400 Å |

TABLE 2-continued

VTE Phosphorescent OLEDs

| Example | HIL | HTL | EML (300 Å, doping %) | BL | ETL 1 |
|---|---|---|---|---|---|
| Example 21 | Compound C 100 Å | NPD 300 Å | Compound D Compound 1146 10% | Compound D 50 Å | Alq 400 Å |

TABLE 3

VTE Device Data

| | x | y | $\lambda_{max}$ (nm) | FWHM (nm) | Voltage (V) | LE (Cd/A) | EQE (%) | PE (lm/W) | LT80% (h) |
|---|---|---|---|---|---|---|---|---|---|
| Comparative Example 1 Compound A | 0.367 | 0.607 | 532 | 66 | 6.5 | 43.2 | 11.5 | 21 | 250 |
| Comparative Example 2 Compound B | 0.336 | 0.623 | 524 | 66 | 5.2 | 58.2 | 15.7 | 35 | 170 |
| Example 1 Compound 53 | 0.345 | 0.619 | 526 | 64 | 5.1 | 69.2 | 18.7 | 42.7 | 20 |
| Example 2 Compound 157 | 0.336 | 0.618 | 518 | 70 | 5.8 | 62.2 | 17.3 | 33.6 | 166 |
| Example 3 Compound 158 | 0.318 | 0.632 | 518 | 60 | 4.7 | 73.4 | 20.2 | 49.1 | 55 |
| Example 4 Compound 159 | 0.339 | 0.616 | 520 | 66 | 5.4 | 58.3 | 16.2 | 33.9 | 82 |
| Example 5 Compound 165 | 0.333 | 0.626 | 522 | 62 | 4.6 | 56.1 | 15.2 | 38.3 | 54 |
| Example 6 Compound 174 | 0.327 | 0.627 | 520 | 64 | 4.9 | 61.5 | 16.9 | 39.3 | 62 |
| Example 7 Compound 175 | 0.314 | 0.635 | 518 | 60 | 5.3 | 71.2 | 19.5 | 42.2 | 77 |
| Example 8 Compound 184 | 0.331 | 0.623 | 518 | 64 | 5.7 | 52.8 | 14.6 | 28.8 | 66 |
| Example 9 Compound 185 | 0.331 | 0.623 | 518 | 64 | 5.4 | 56.7 | 15.7 | 32.9 | 53 |
| Example 10 Compound 314 | 0.308 | 0.636 | 516 | 60 | 5.0 | 61.4 | 16.9 | 38.9 | 44 |
| Example 11 Compound 321 | 0.326 | 0.630 | 520 | 60 | 5.1 | 61.4 | 16.6 | 37.7 | 73 |
| Example 12 Compound 625 | 0.338 | 0.622 | 524 | 66 | 5.1 | 60.1 | 16.3 | 37.2 | 124 |
| Example 13 Compound 626 | 0.336 | 0.624 | 522 | 64 | 5.5 | 67.4 | 18.2 | 38.2 | 71 |
| Example 14 Compound 627 | 0.345 | 0.619 | 526 | 64 | 5.2 | 65.2 | 17.7 | 39.2 | 121 |
| Example 15 Compound 628 | 0.351 | 0.615 | 526 | 64 | 5.6 | 68.6 | 18.6 | 38.7 | 124 |
| Example 16 Compound 633 | 0.366 | 0.608 | 528 | 66 | 5.0 | 66.3 | 17.8 | 41.8 | 56 |
| Example 17 Compound 643 | 0.339 | 0.625 | 526 | 60 | 5.2 | 71.5 | 19.1 | 43.3 | 108 |
| Example 18 Compound 652 | 0.349 | 0.616 | 526 | 66 | 5.7 | 53.4 | 14.5 | 29.3 | 104 |
| Example 19 Compound 653 | 0.337 | 0.626 | 524 | 62 | 5.1 | 65.6 | 17.6 | 40.8 | 84 |
| Example 20 Compound 1145 | 0.343 | 0.618 | 524 | 68 | 5.6 | 61.3 | 16.7 | 34.4 | 59 |
| Example 21 Compound 1146 | 0.343 | 0.618 | 524 | 68 | 5.6 | 63 | 17.2 | 35.5 | 157 |

Table 3 is a summary of the device data. The luminous efficiency (LE), external quantum efficiency (EQE) and power efficiency (PE) were measured at 1000 nits, while the lifetime ($LT_{80\%}$) was defined as the time required for the device to decay to 80% of its initial luminance under a constant current density of 40 mA/cm².

The advantage of alkyl substitution on the 4- and 5-positions of the DBX-pyridine ring is clear from Table 3. Compared to Comparative Example 1, with no substitution at the 4- or 5-positions of the DBX-pyridine ring, the compounds of Formula I are more saturated (lower CIE x coordinate and shorter $\lambda_{max}$) and the broadness as measured by the FWHM is comparable. In all the inventive compounds, the voltage is lower and the LE, PE and EQE values are all higher. In the case of Compounds 53, 158, 175, 633 and 643, the PE is at least twice as high as Comparative Example 1.

Compared to Comparative Example 2 (Compound B), with only one-carbon substitution (methyl) at the 4-position of the DBX-pyridine ring, Compounds 53, 158, 174, 175, 184, 185, and 314 have more saturated color based CIE x coordinate and Compounds 157, 158, 159, 165, 174, 175, 184, 185, 314, 321 and 626 all have shorter $\lambda_{max}$ values. Most of the compounds of Formula I have narrower emission profiles (as measured by FWHM) than Comparative Example 2. Compounds 53, 158, 165, 314, 321, 625, 633 and 653 all have lower driving voltages than Comparative Example 2. Most of the compounds of Formula I have greater LE, PE and EQE values than Comparative Example 2.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

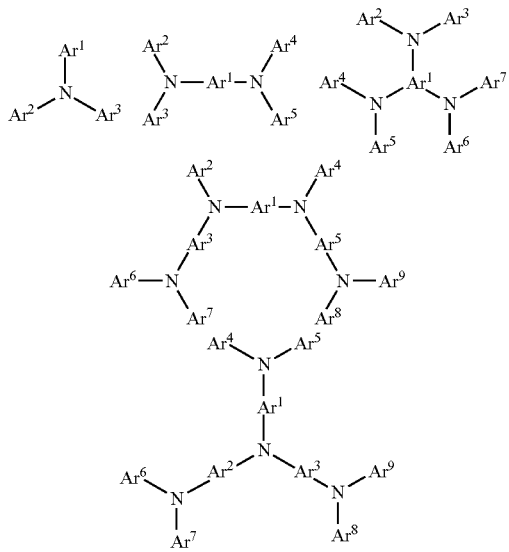

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

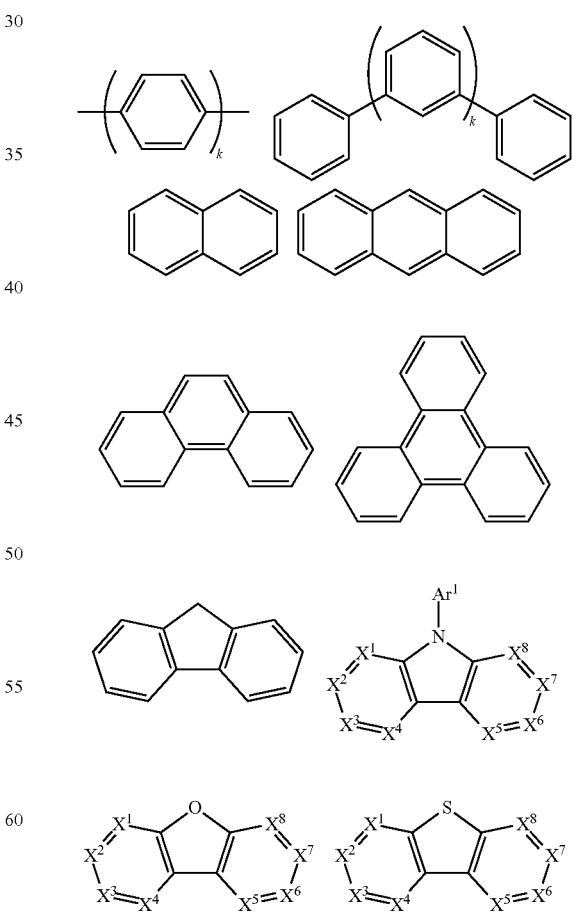

k is an integer from 1 to 20; $X^1$ to $X^8$ is C (including CH) or N; $Ar^1$ has the same group defined above.

Examples of metal complexes used in HIL or HTL include, but not limit to the following general formula:

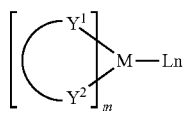

M is a metal, having an atomic weight greater than 40; ($Y^1$—$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$—$Y^2$) is a 2-phenylpyridine derivative.
In another aspect, ($Y^1$—$Y^2$) is a carbene ligand.
In another aspect, M is selected from Ir, Pt, Os, and Zn.
In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

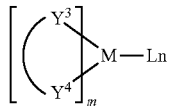

M is a metal; ($Y^3$—$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

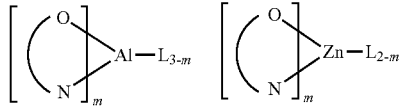

(O—N) is a bidentate ligand, having metal coordinated to atoms O and N.

In another aspect, M is selected from Ir and Pt.
In a further aspect, ($Y^3$—$Y^4$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

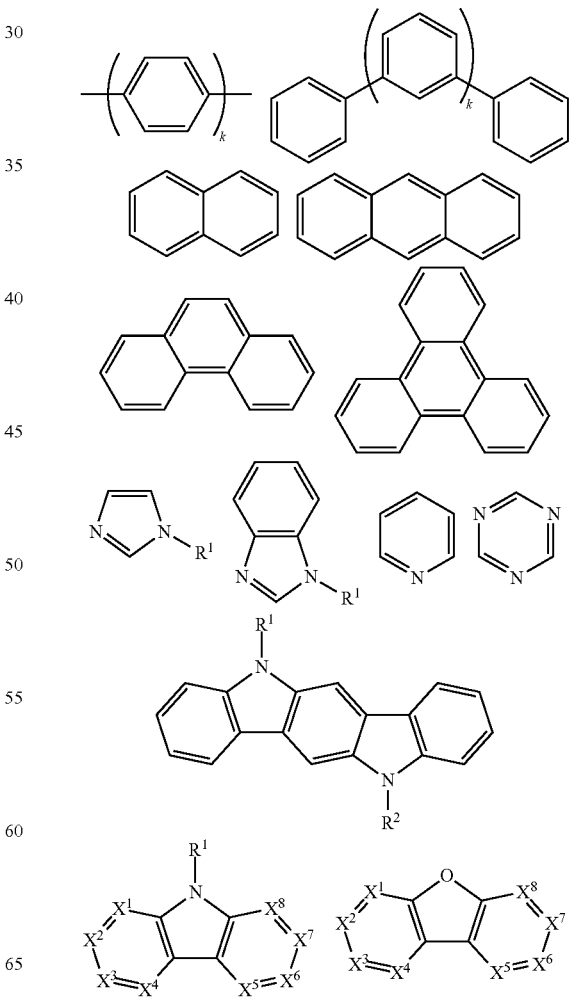

-continued

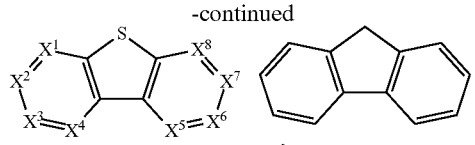

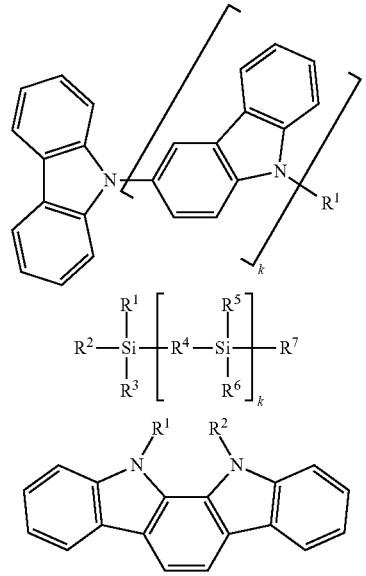

R$^1$ to R$^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

X$^1$ to X$^8$ is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

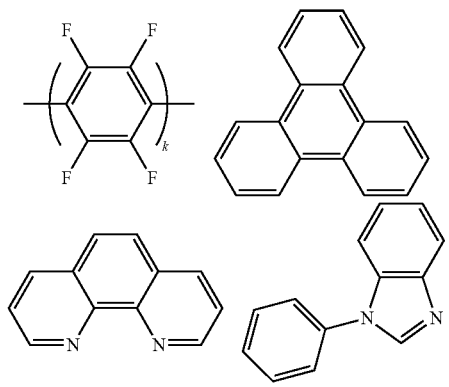

-continued

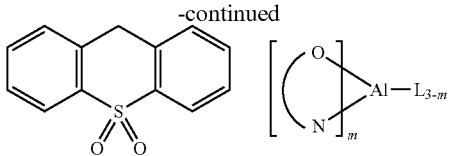

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

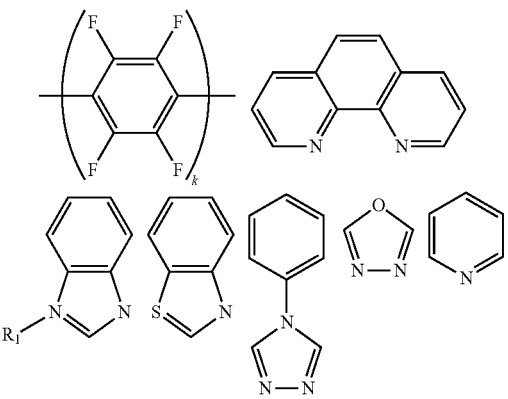

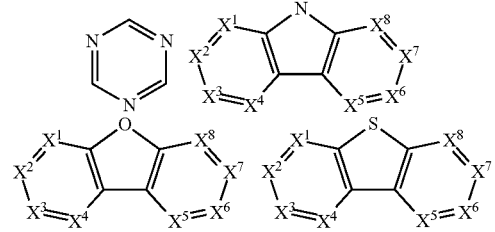

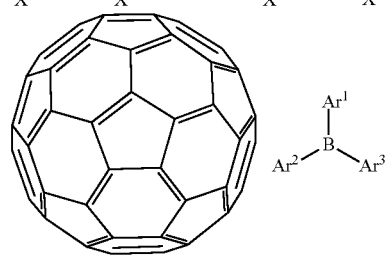

R$^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, it has the similar definition as Ar's mentioned above.

Ar$^1$ to Ar$^a$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

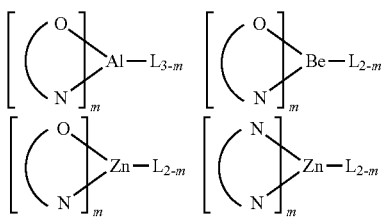

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $\mathrm{-\!\!\!+\!CH_xF_y\!\!+\!\!\!-}_n$ | Appl. Phys. Lett. 78, 673 (2001) |

TABLE 3-continued
| MATERIAL | EXAMPLES OF MATERIAL | PUBLICATIONS |
|---|---|---|
| Conducting polymers (e.g., PEDOT:PSS, polyaniline, polypthiophene) | 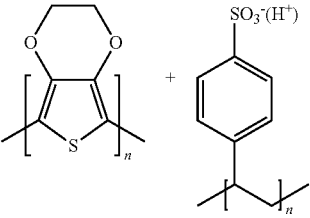 | Synth. Met. 87, 171 (1997) WO2007002683 |
| Phosphonic acid and silane SAMs | 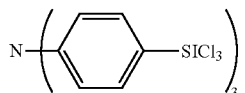 | US20030162053 |
| Triarylamine or polythiophene polymers with conductivity dopants | 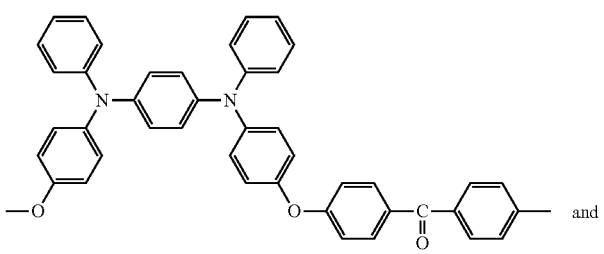 and 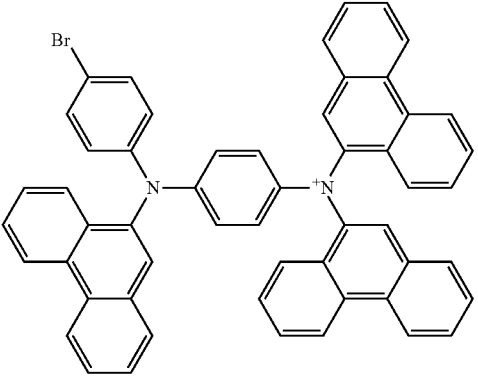 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 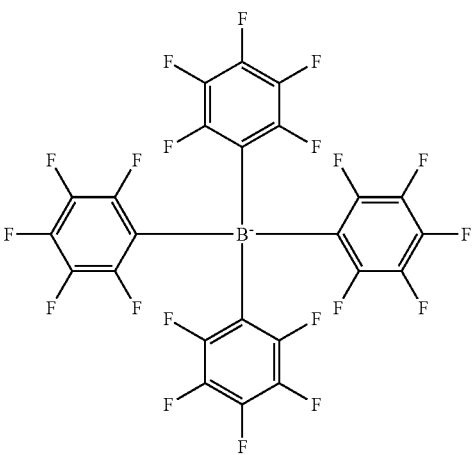 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |

| MATERIAL | EXAMPLES OF MATERIAL | PUBLICATIONS |
|---|---|---|
| Arylamines complexed with metal oxides such as molybdenum and tungsten oxides | 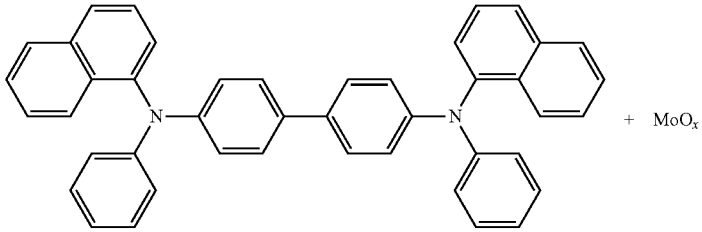 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) WO2009018009 |
| p-type semiconducting organic complexes | | US20020158242 |
| Metal organometallic complexes | | US20060240279 |
| Cross-linkable compounds | 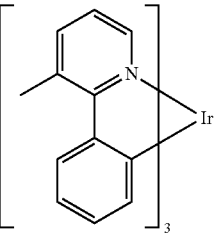 | US20080220265 |
| Hole transporting materials | | |
| Triarylamines (e.g., TPD, α-NPD) | 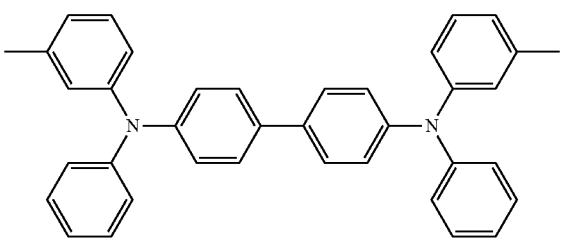 | Appl. Phys. Lett. 51, 913 (1987) |

TABLE 3-continued
| MATERIAL | EXAMPLES OF MATERIAL | PUBLICATIONS |
|---|---|---|
| | 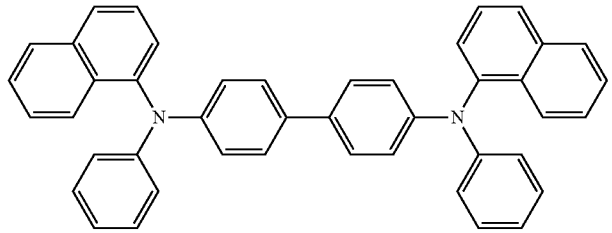 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 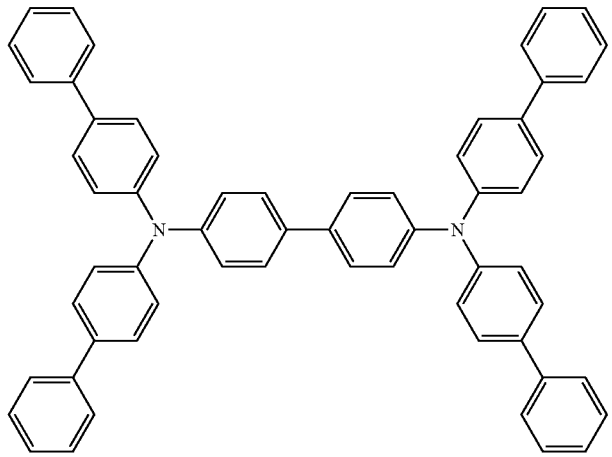 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 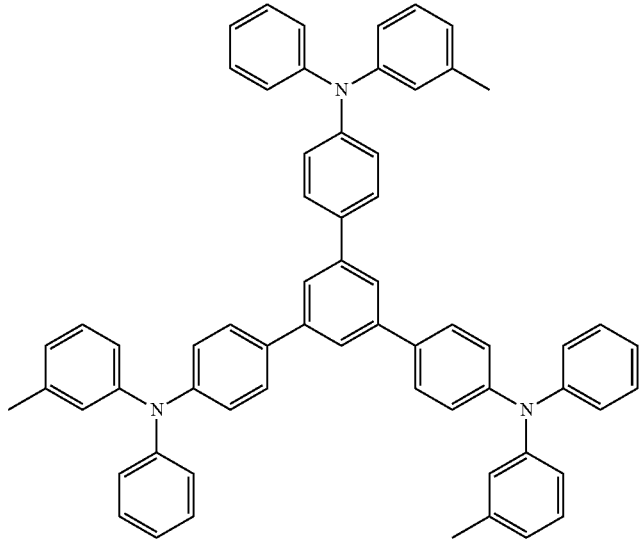 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 3-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 3-continued
| MATERIAL | EXAMPLES OF MATERIAL | PUBLICATIONS |
|---|---|---|
| Triarylamine with (di)benzothiophene/ (di)benzofuran | 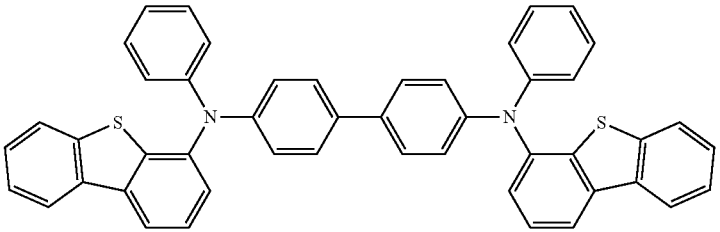 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |
| Indolocarbazoles | 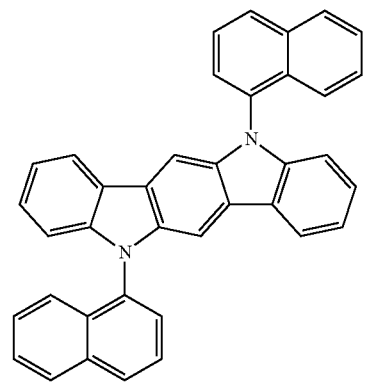 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 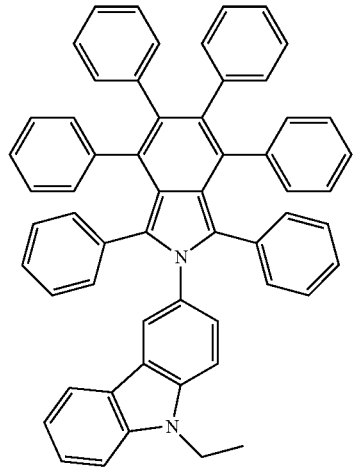 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 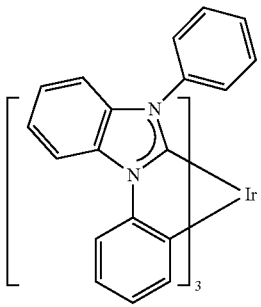 | US20080018221 |
Phosphorescent OLED host materials
Red hosts TABLE 3-continued

| MATERIAL | EXAMPLES OF MATERIAL | PUBLICATIONS |
|---|---|---|
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 3-continued

| MATERIAL | EXAMPLES OF MATERIAL | PUBLICATIONS |
|---|---|---|
| Aromatic fused rings | | WO2009066779, WO2009066778, WO2009063833, US20090045731, US20090045730, WO2009008311, US20090008605, US20090009065 |
| Zinc complexes | | WO2009062578 |

Green hosts

| | | |
|---|---|---|
| Arylcarbazoles | | Appl. Phys. Lett. 78, 1622 (2001) |
| | | US20030175553 |
| | | WO2001039234 |
| Aryltriphenylene compounds | | US20060280965 |

TABLE 3-continued

| MATERIAL | EXAMPLES OF MATERIAL | PUBLICATIONS |
|---|---|---|
| | | US20060280965 |
| | | WO2009021126 |
| Donor acceptor type molecules | | WO2008056746 |
| Aza-carbazole/DBT/ DBF | | JP2008074939 |
| Polymers (e.g., PVK) | | Appl. Phys. Lett. 77, 2280 (2000) |

TABLE 3-continued

| MATERIAL | EXAMPLES OF MATERIAL | PUBLICATIONS |
|---|---|---|
| Spirofluorene compounds | | WO2004093207 |
| Metal phenoxybenzooxazole compounds | | WO2005089025 |
| | | WO2006132173 |
| | | JP2005011610 |
| Spirofluorene-carbazole compounds | | JP2007254297 |

TABLE 3-continued
| MATERIAL | EXAMPLES OF MATERIAL | PUBLICATIONS |
|---|---|---|
| | 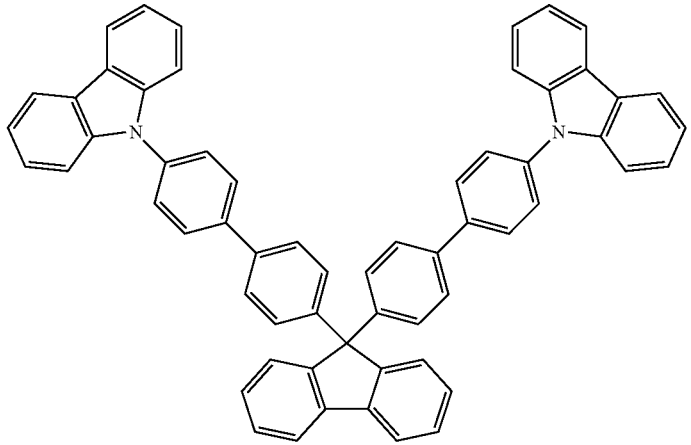 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 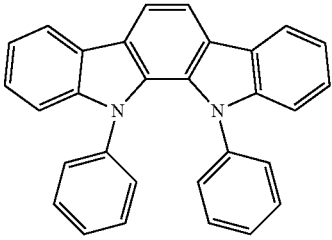 [SMILES: c1ccc(-n2c3ccccc3c3ccc4c5ccccc5n(-c5ccccc5)c4c32)cc1] | WO2007063796 |
| | 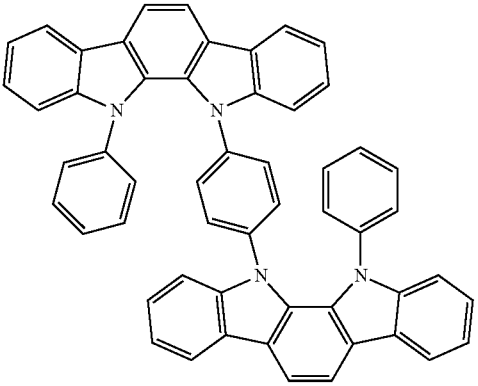 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 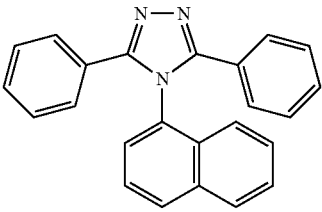 [SMILES: c1ccc(-c2nnc(-c3ccccc3)n2-c2cccc3ccccc23)cc1] | J. Appl. Phys. 90, 5048 (2001) |
| | 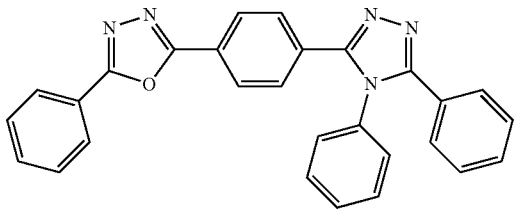 [SMILES: c1ccc(-c2nnc(-c3ccc(-c4nnc(-c5ccccc5)n4-c4ccccc4)cc3)o2)cc1] | WO2004107822 |

TABLE 3-continued
| MATERIAL | EXAMPLES OF MATERIAL | PUBLICATIONS |
| --- | --- | --- |
| Tetraphenylene complexes | 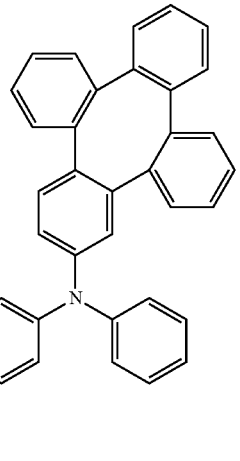 | US20050112407 |
| Metal phenoxypyridine compounds | 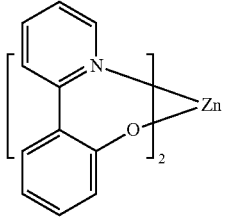 | WO2005030900 |
| Metal coordination complexes (e.g., Zn, Al with N^N ligands) | 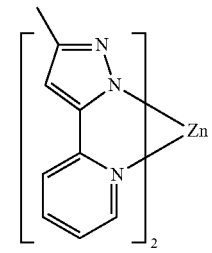 | US20040137268, US20040137267 |
| Blue hosts | | |
| Arylcarbazoles | 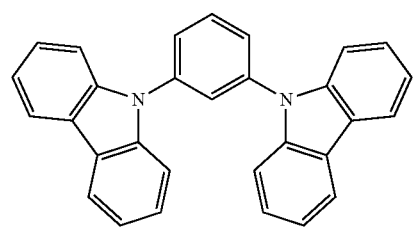 [SMILES: c1cc(-n2c3ccccc3c3ccccc32)cc(-n2c3ccccc3c3ccccc32)c1] | Appl. Phys. Lett, 82, 2422 (2003) |
| | 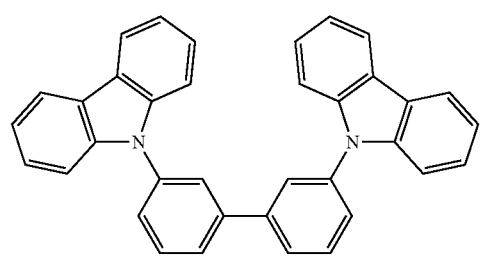 [SMILES: c1cc(-c2cccc(-n3c4ccccc4c4ccccc43)c2)cc(-n2c3ccccc3c3ccccc32)c1] | US20070190359 |

TABLE 3-continued
| MATERIAL | EXAMPLES OF MATERIAL | PUBLICATIONS |
|---|---|---|
| Dibenzothiophene/ Dibenzofuran- carbazole compounds | 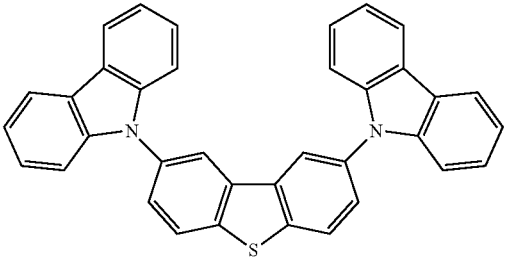 [SMILES: c1ccc2c(c1)c1ccccc1n2-c1ccc2sc3ccc(-n4c5ccccc5c5ccccc54)cc3c2c1] | WO2006114966, US20090167162 |
| | 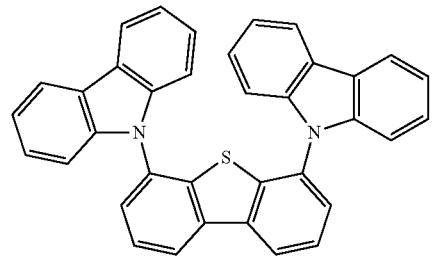 [SMILES: c1cc(-n2c3ccccc3c3ccccc32)c2sc3c(-n4c5ccccc5c5ccccc54)cccc3c2c1] | US20090167162 |
| | 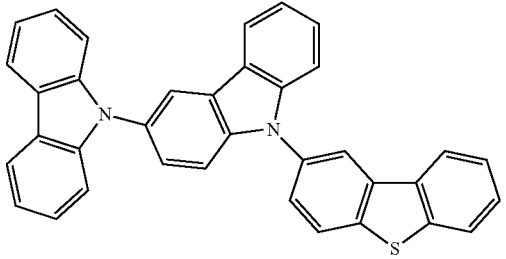 [SMILES: c1ccc2c(c1)sc1ccc(-n3c4ccccc4c4cc(-n5c6ccccc6c6ccccc65)ccc43)cc12] | WO2009086028 |
| | 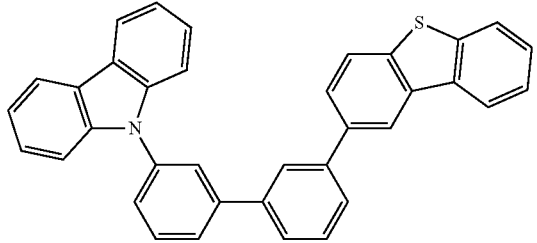 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 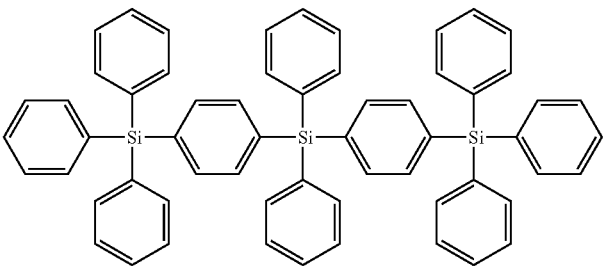 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 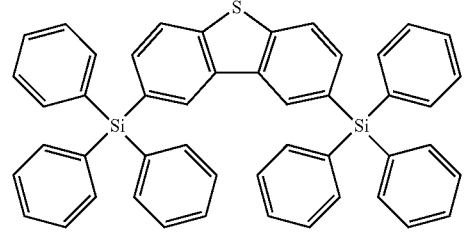 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | U.S. Pat. No. 7,154,114 |

Phosphorescent dopants
Red dopants

| Heavy metal porphyrins (e.g., PtOEP) | | Nature 395, 151 (1998) |
| --- | --- | --- |
| Iridium(III) organometallic complexes | | Appl. Phys. Lett. 78, 1622 (2001) |

TABLE 3-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 3-continued

| MATERIAL | EXAMPLES OF MATERIAL | PUBLICATIONS |
| --- | --- | --- |
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 3-continued

| MATERIAL | EXAMPLES OF MATERIAL | PUBLICATIONS |
|---|---|---|
| Osminum(III) complexes | | Chem. Mater. 17, 3532 (2005) |
| Ruthenium(II) complexes | | Adv. Mater. 17, 1059 (2005) |
| Rhenium (I), (II) and (III) complexes | | US20050244673 |

Green dopants

| MATERIAL | EXAMPLES OF MATERIAL | PUBLICATIONS |
|---|---|---|
| Iridium(III) organometallic complexes | and its derivatives | Inorg. Chem. 40, 1704 (2001) |
| | | US20020034656 |

TABLE 3-continued

| MATERIAL | EXAMPLES OF MATERIAL | PUBLICATIONS |
|---|---|---|
| | | U.S. Pat. No. 7,332,232 |
| | | US20090108737 |
| | | US20090039776 |
| | | U.S. Pat. No. 6,921,915 |

TABLE 3-continued

| MATERIAL | EXAMPLES OF MATERIAL | PUBLICATIONS |
| --- | --- | --- |
| | | U.S. Pat. No. 6,687,266 |
| | | Chem. Mater. 16, 2480 (2004) |
| | | US20070190359 |
| | | US 20060008670 JP2007123392 |
| | | Adv. Mater. 16, 2003 (2004) |

TABLE 3-continued
| MATERIAL | EXAMPLES OF MATERIAL | PUBLICATIONS |
|---|---|---|
| | 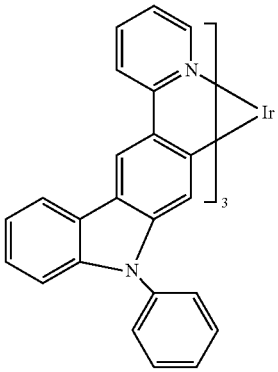 | Angew. Chem. Int. Ed. 2006, 45, 7800 |
| | 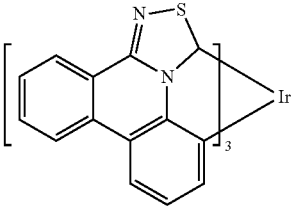 | WO2009050290 |
| | 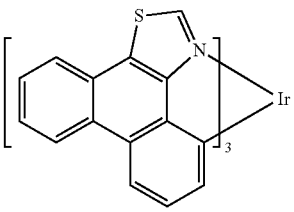 | US20090165846 |
| | 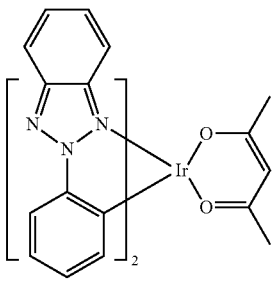 | US20080015355 |
| Monomer for polymeric metal organometallic compounds | 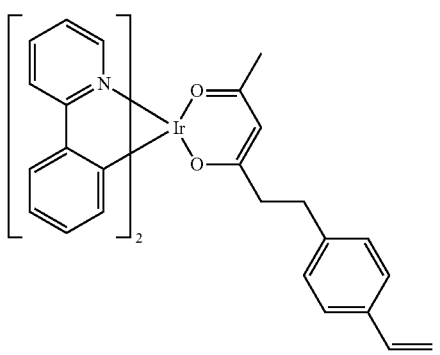 | U.S. Pat. No. 7,250,226, U.S. Pat. No. 7,396,598 |

TABLE 3-continued
| MATERIAL | EXAMPLES OF MATERIAL | PUBLICATIONS |
|---|---|---|
| Pt(II) organometallic complexes, including polydentated ligands | 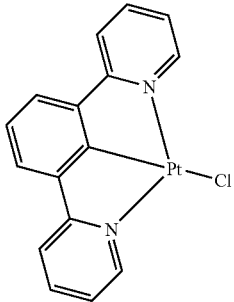 | Appl. Phys. Lett. 86, 153505 (2005) |
| | 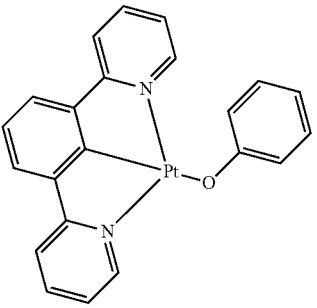 | Appl. Phys. Lett. 86, 153505 (2005) |
| | 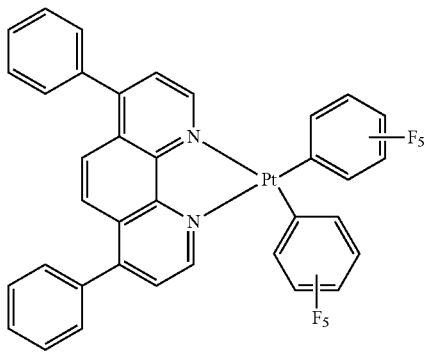 | Chem. Lett. 34, 592 (2005) |
| | 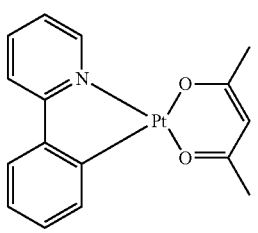 | WO2002015645 |
| | 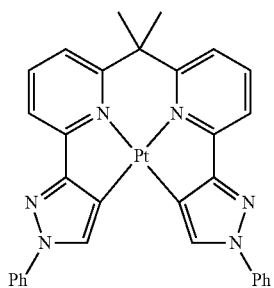 | US20060263635 |

TABLE 3-continued
| MATERIAL | EXAMPLES OF MATERIAL | PUBLICATIONS |
|---|---|---|
| Cu complexes | 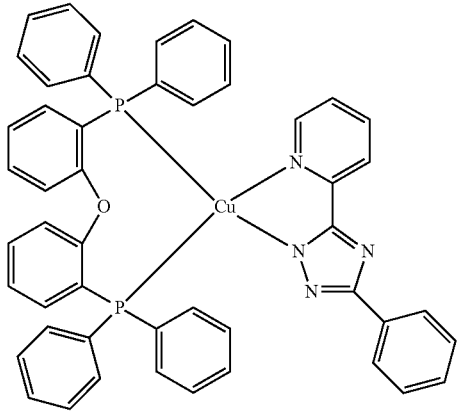 | WO2009000673 |
| Gold complexes | 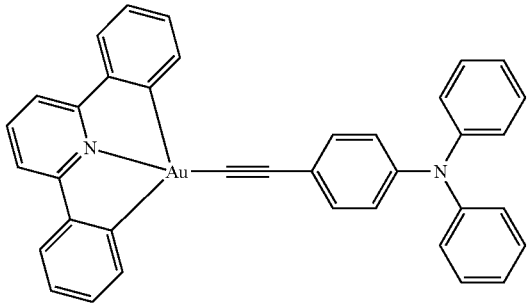 | Chem. Commun. 2906 (2005) |
| Rhenium(III) complexes | 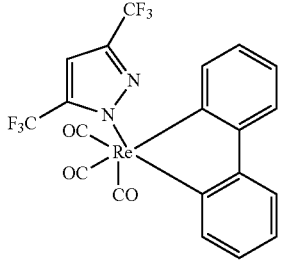 | Inorg. Chem. 42, 1248 (2003) |
| Deuterated organometallic complexes | 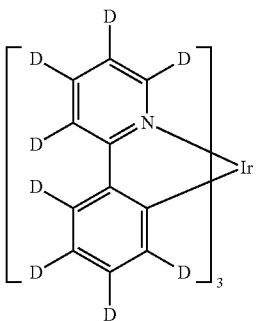 | US20030138657 |

| MATERIAL | EXAMPLES OF MATERIAL | PUBLICATIONS |
|---|---|---|
| Organometallic complexes with two or more metal centers | 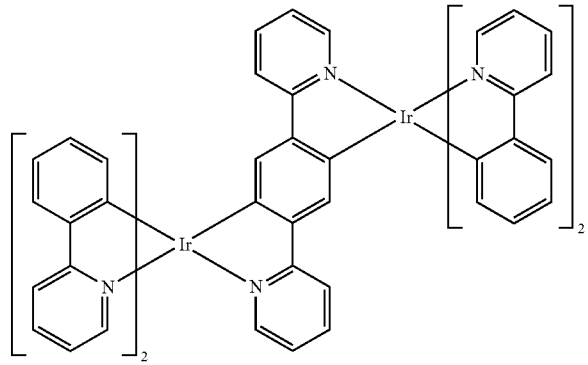 | US20030152802 |
| | 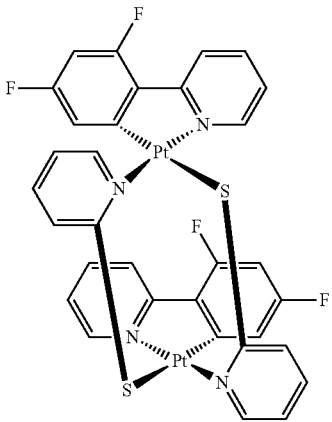 | U.S. Pat. No. 7,090,928 |
| Blue dopants | | |
| Iridium(III) organometallic complexes | 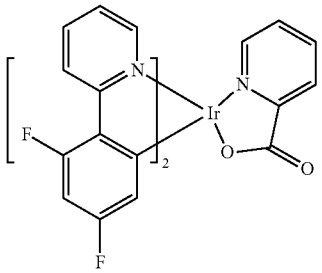 | WO2002002714 |
| | 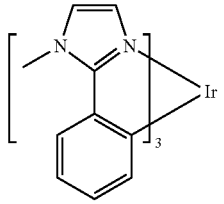 | WO2006009024 |
| | 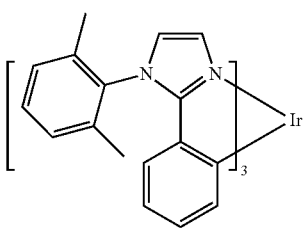 | US20060251923 |

TABLE 3-continued

| MATERIAL | EXAMPLES OF MATERIAL | PUBLICATIONS |
|---|---|---|
| | (structure) | U.S. Pat. No. 7,393,599, WO2006056418, US20050260441, WO2005019373 |
| | (structure) | U.S. Pat. No. 7,534,505 |
| | (structure) | U.S. Pat. No. 7,445,855 |
| | (structure) | US20070190359, US20080297033 |
| | (structure) | U.S. Pat. No. 7,338,722 |
| | (structure) | US20020134984 |

TABLE 3-continued
| MATERIAL | EXAMPLES OF MATERIAL | PUBLICATIONS |
|---|---|---|
| | 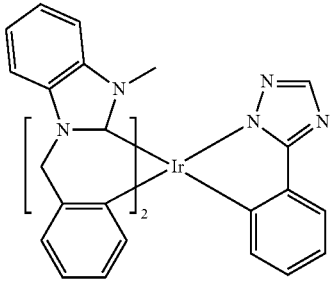 | Angew. Chem. Int. Ed. 47, 1 (2008) |
| | 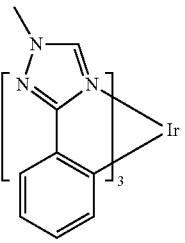 | Chem. Mater. 18, 5119 (2006) |
| | 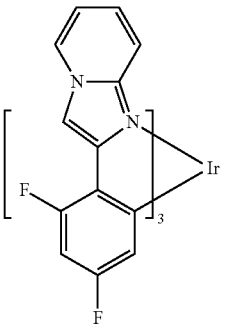 | Inorg. Chem. 46, 4308 (2007) |
| | 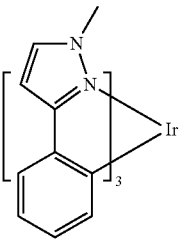 | WO2005123873 |
| | 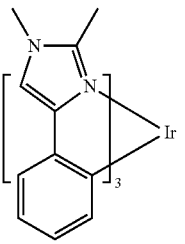 | WO2005123873 |
| | 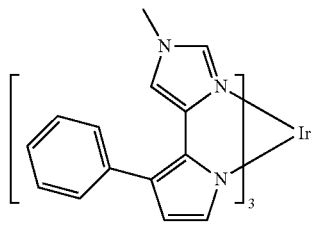 | WO2007004380 |

TABLE 3-continued

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

Exciton/hole blocking layer materials

TABLE 3-continued
| MATERIAL | EXAMPLES OF MATERIAL | PUBLICATIONS |
|---|---|---|
| Bathocuprine compounds (e.g., BCP, BPhen) | 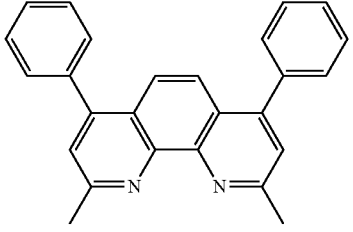 [SMILES: Cc1cc(-c2ccccc2)c2ccc3c(-c4ccccc4)cc(C)nc3c2n1] 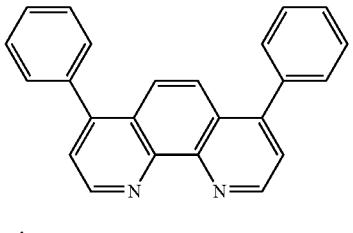 | Appl. Phys. Lett. 75, 4 (1999)<br><br>Appl. Phys. Lett. 79, 449 (2001) |
| Metal 8-hydroxyquinolates (e.g., BAlq) | 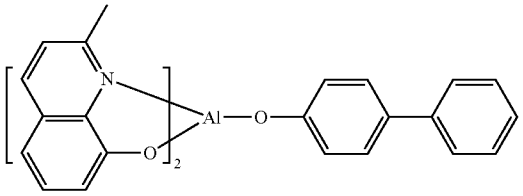 | Appl. Phys. Lett. 81, 162 (2002) |
| 5-member ring electron deficient heterocycles such as triazole, oxadiazole, imidazole, benzoimidazole | 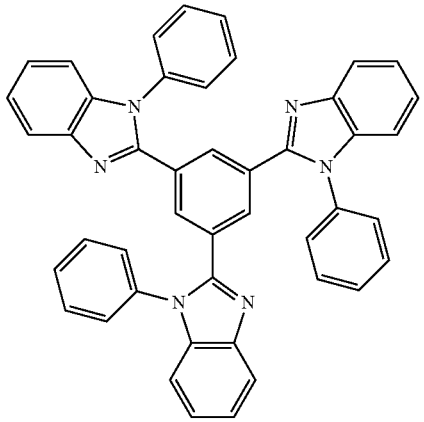 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 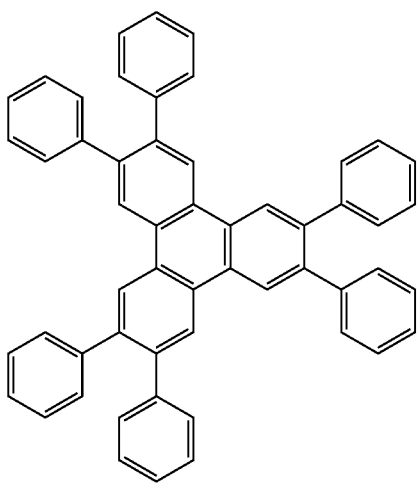 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 3-continued
| MATERIAL | EXAMPLES OF MATERIAL | PUBLICATIONS |
|---|---|---|
| Fluorinated aromatic compounds | 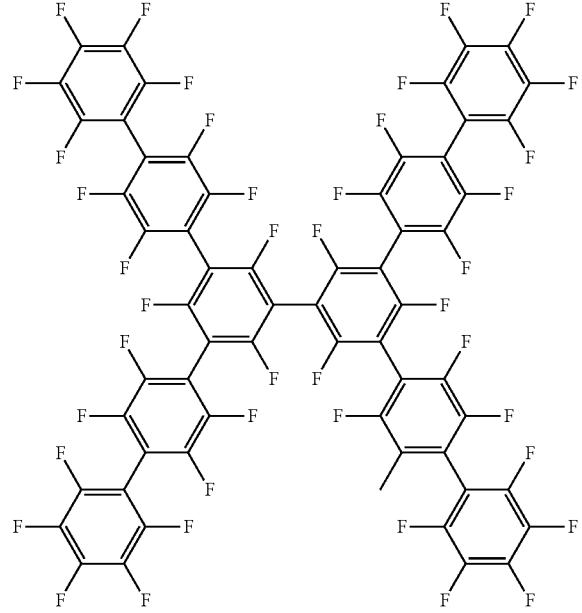 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 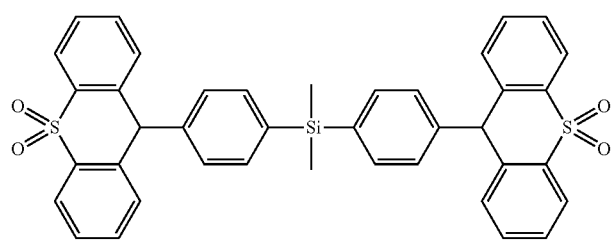 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
Electron transporting materials
| | | |
|---|---|---|
| Anthracene-benzoimidazole compounds | 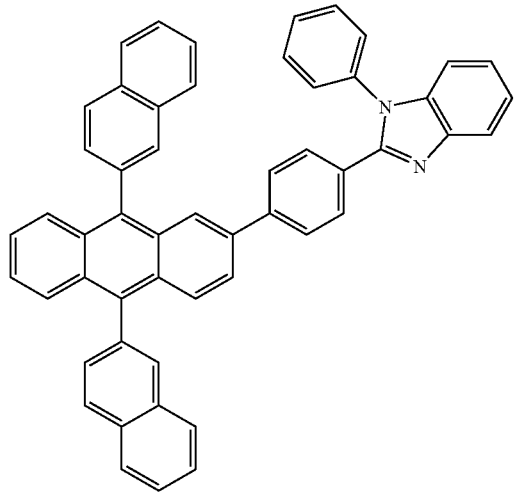 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 3-continued
| MATERIAL | EXAMPLES OF MATERIAL | PUBLICATIONS |
|---|---|---|
| | 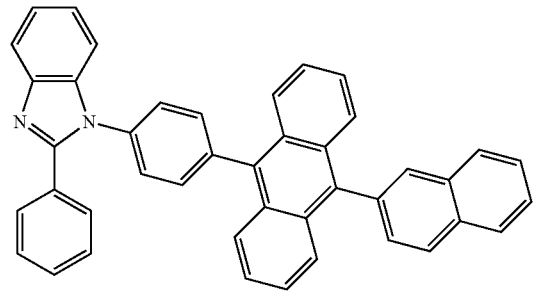 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 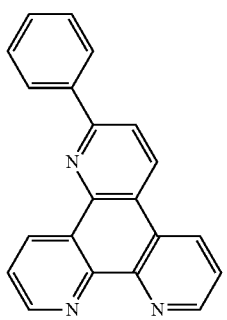 [SMILES: c1ccc(-c2ccc3c4cccnc4c4ncccc4c3n2)cc1] | US20090115316 |
| Anthracene-benzothiazole compounds | 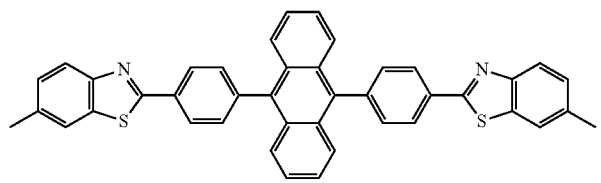 | Appl. Phys. Lett. 89, 063504 (2006) |
| Metal 8-hydroxyquinolates (e.g., $Alq_3$, $Zrq_4$) | 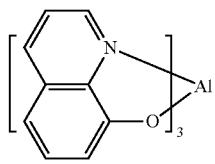 | Appl. Phys. Lett. 51, 913 (1987)<br>U.S. Pat. No. 7,230,107 |
| Metal hydroxybenoquinolates | 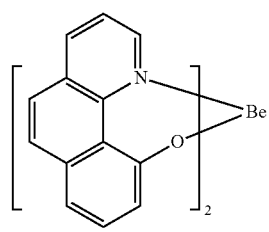 | Chem. Lett. 5, 905 (1993) |
| Bathocuprine compounds such as BCP, BPhen, etc | 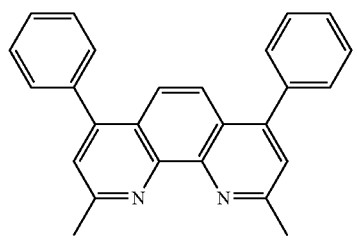 [SMILES: Cc1cc(-c2ccccc2)c2ccc3c(-c4ccccc4)cc(C)nc3c2n1] | Appl. Phys. Lett. 91, 263503 (2007) |

TABLE 3-continued

| MATERIAL | EXAMPLES OF MATERIAL | PUBLICATIONS |
| --- | --- | --- |
| | (structure) | Appl. Phys. Lett. 79, 449 (2001) |
| 5-member ring electron deficient heterocycles (e.g., triazole, oxadiazole, imidazole, benzoimidazole) | (structure) | Appl. Phys. Lett. 74, 865 (1999) |
| | (structure) | Appl. Phys. Lett. 55, 1489 (1989) |
| | (structure) | Jpn. J. Apply. Phys. 32, L917 (1993) |
| Silole compounds | (structure) | Org. Electron. 4, 113 (2003) |
| Arylborane compounds | (structure) | J. Am. Chem. Soc. 120, 9714 (1998) |

TABLE 3-continued

| MATERIAL | EXAMPLES OF MATERIAL | PUBLICATIONS |
| --- | --- | --- |
| Fluorinated aromatic compounds | | J. Am. Chem. Soc. 122, 1832 (2000) |
| Fullerene (e.g., C60) | | US20090101870 |
| Triazine complexes | | US20040036077 |
| Zn (N^N) complexes | | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, THF is tetrahydrofuran, DCM is dichloromethane, S-Phos is dicyclohexyl(2',6'-dimethoxy-[1,1'-biphenyl]-2-yl)phosphine.

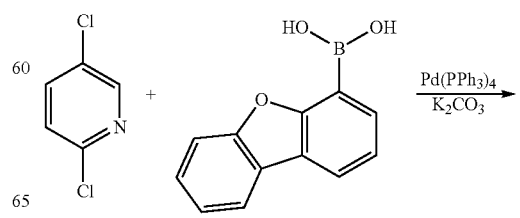

Synthesis of 5-chloro-2-(dibenzo[b,d]furan-4-yl)pyridine

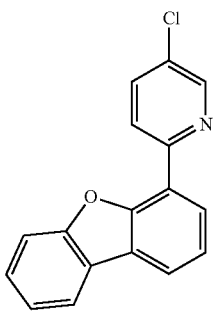

Dibenzo[b,d]furan-4-ylboronic acid (9.5 g, 44.8 mmol), 2,5-dichloropyridine (7.0 g, 47.0 mmol), Pd(PPh₃)₄ (2.6 g, 2.2 mmol) and potassium carbonate (18.6 g, 134 mmol) were added to dimethoxyethane (75 mL) and water (75 mL). The reaction mixture was degassed with nitrogen before being heated to reflux overnight. EtOAc and water were added, the organic layer separated and the aqueous layer was extracted with 3×50 mL dichloromethane and dried over sodium sulfate. After removing the solvent under reduced pressure, the crude product was chromatographed on silica gel with dichloromethane to yield 11.7 g of crude product. The product was crystallized from hexane to give 9.5 g (76%) of 5-chloro-2-(dibenzo[b,d]furan-4-yl)pyridine as white needles. The product was confirmed by GC/MS.

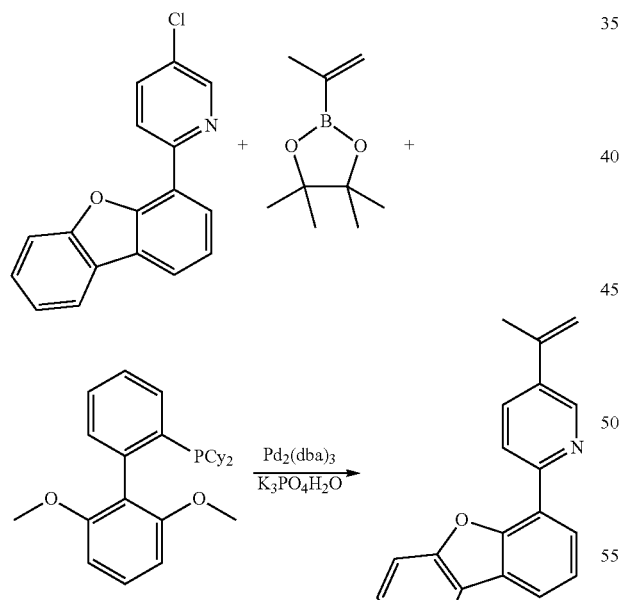

Synthesis of 2-(dibenzo[b,d]furan-4-yl)-5-(prop-1-en-2-yl)pyridine

5-Chloro-2-(dibenzo[b,d]furan-4-yl)pyridine (9.5 g, 34.0 mmol), dicyclohexyl(2',6'-dimethoxy-[1,1'-biphenyl]-2-yl)phosphine (1.1 g, 2.7 mmol), and potassium phosphate tribasic monohydrate (23.5 g, 102 mmol) were added to toluene (200 mL) and water (20 mL) and the reaction mixture was degassed with nitrogen. Pd₂(dba)₃ (0.622 g, 0.679 mmol) and 4,4,5,5-tetramethyl-2-(prop-1-en-2-yl)-1,3,2-dioxaborolane (7.7 mL, 40.8 mmol) were added and the reaction mixture was heated to reflux overnight. EtOAc and water were added, the organic layer separated and the aqueous layer was extracted with 3×50 mL dichloromethane and dried over sodium sulfate. After removing the solvent under reduced pressure, 12.7 g of amber oil was obtained. The crude material was chromatographed on silica with 9/1 (v/v) hexane/EtOAc to give 7.5 g (77%) of 2-(dibenzo[b,d]furan-4-yl)-5-(prop-1-en-2-yl)pyridine as a white solid. The product was confirmed by GC/MS and used without further purification.

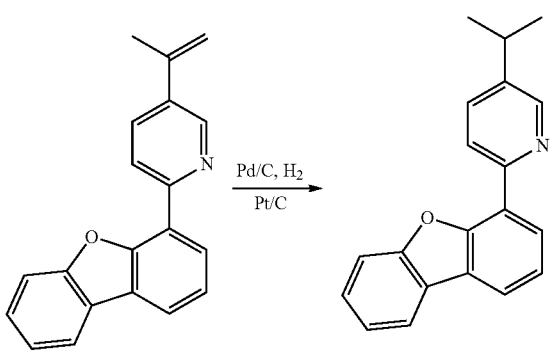 [SMILES: C=C(C)c1ccc(-c2cccc3c2oc2ccccc23)nc1 ; CC(C)c1ccc(-c2cccc3c2oc2ccccc23)nc1]

Synthesis of 2-(dibenzo[b,d]furan-4-yl)-5-isopropylpyridine 2-(Dibenzo[b,d]furan-4-yl)-5-(prop-1-en-2-yl)pyridine (7.5 g, 26.3 mmol) was added to a hydrogenator bottle containing EtOH (150 mL). The reaction mixture was degassed by bubbling nitrogen for 10 min Pd/C (0.28 g, 2.63 mmol) and Pt/C (0.26 g, 1.3 mmol) were added to the reaction mixture. The reaction mixture was placed on the Parr hydrogenator for 1 h. The reaction mixture was filtered on a tightly packed Celite® bed and washed with dichloromethane to yield 7.5 g (99%) of the desired product. The product was confirmed by GC/MS and NMR.

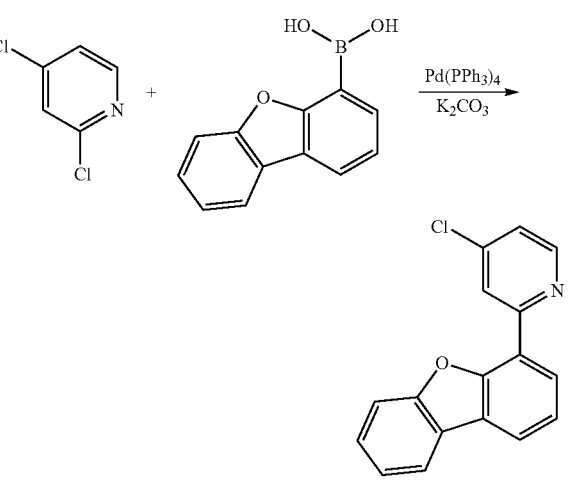

Synthesis of 5-chloro-2-(dibenzo[b,d]furan-4-yl)pyridine

Dibenzo[b,d]furan-4-ylboronic acid (25 g, 118 mmol), 2,4-dichloropyridine (19.2 g, 130 mmol), Pd(PPh₃)₄ (4.1 g, 3.5 mmol) and potassium carbonate (48.9 g, 354 mmol) were added to dimethoxyethane (200 mL) and water (200 mL). The reaction mixture was degassed with nitrogen before being heated to reflux overnight. EtOAc and water were added, the organic layer separated and the aqueous layer was extracted with 3×50 mL dichloromethane and dried over sodium sulfate. After removing the solvent under reduced pressure, the crude product was chromatographed on silica gel with dichloromethane to yield 33.4 g of crude product. The product was crystallized from hexane to give 27.0 g (82%) of 4-chloro-2-(dibenzo[b,d]furan-4-yl)pyridine as white needles. The product was confirmed by GC/MS and NMR.

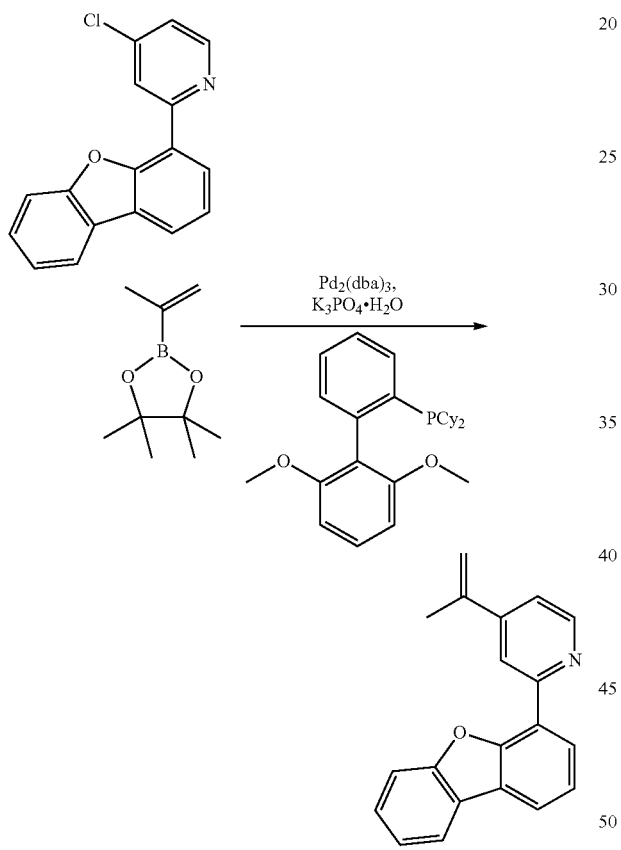

Synthesis of 2-(dibenzo[b,d]furan-4-yl)-4-(prop-1-en-2-yl)pyridine

4-Chloro-2-(dibenzo[b,d]furan-4-yl)pyridine (24.0 g, 86.0 mmol), dicyclohexyl(2',6'-dimethoxy-[1,1'-biphenyl]-2-yl)phosphine (2.8 g, 6.9 mmol), and potassium phosphate tribasic monohydrate (59.3 g, 257 mmol) were added to toluene (400 mL) and water (40 mL) and the reaction mixture was degassed. Pd₂(dba)₃ (1.6 g, 1.7 mmol) and 4,4,5,5-tetramethyl-2-(prop-1-en-2-yl)-1,3,2-dioxaborolane (19.4 mL, 103 mmol) were added and the reaction mixture was heated to reflux overnight. EtOAc and water were added, the organic layer separated and the aqueous layer was extracted with 3×50 mL dichloromethane and dried over sodium sulfate. After removing the solvent under reduced pressure, 33.0 g of amber oil was obtained. The crude material was chromatographed on silica with 9/1 (v/v) DCM/EtOAc to give 23.5 g (96%) of 2-(dibenzo[b,d]furan-4-yl)-4-(prop-1-en-2-yl)pyridine as a white solid. The product was confirmed by GC/MS and used without further purification.

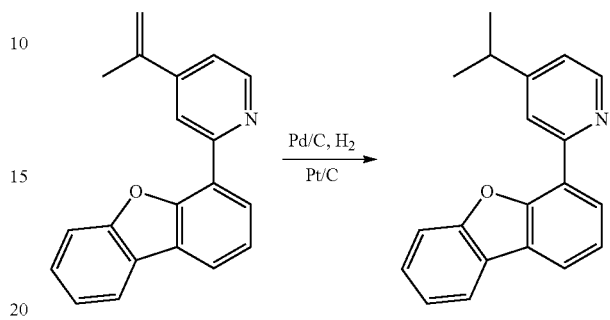

Synthesis of 2-(dibenzo[b,d]furan-4-yl)-4-isopropylpyridine 2-(Dibenzo[b,d]furan-4-yl)-5-(prop-1-en-2-yl)pyridine (8.0 g, 28 mmol) was added to a hydrogenator bottle containing EtOH (150 mL). The reaction mixture was degassed by bubbling N₂ for 10 min. Pd/C (0.60 g, 5.6 mmol) and Pt/C (0.55 g, 2.8 mmol) were added to the reaction mixture. The reaction mixture was placed on the Parr hydrogenator for 1 h. The reaction mixture was filtered on a tightly packed Celite® bed and washed with dichloromethane. The crude product was chromatographed on silica gel with 9/1 (v/v) hexane/EtOAc to yield 7.2 g (96%) of 2-(dibenzo[b,d]furan-4-yl)-4-isopropylpyridine. The product was confirmed by GC/MS and NMR.

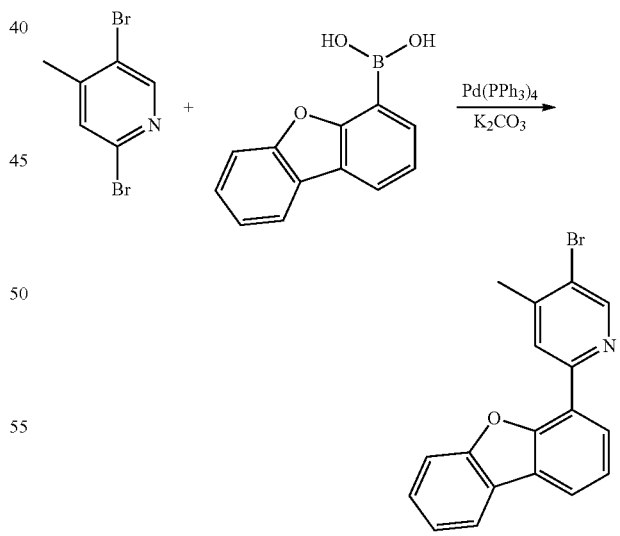

Synthesis of 5-bromo-2-(dibenzo[b,d]furan-4-yl)-4-methylpyridine 2,5-Dibromo-4-methylpyridine (30 g, 118 mmol), dibenzo[b,d]furan-4-ylboronic acid (25 g, 118 mmol), Pd(PPh₃)₄ (1.4 g, 1.18 mmol), and K₂CO₃ (49 g, 354 mmol) were added to a

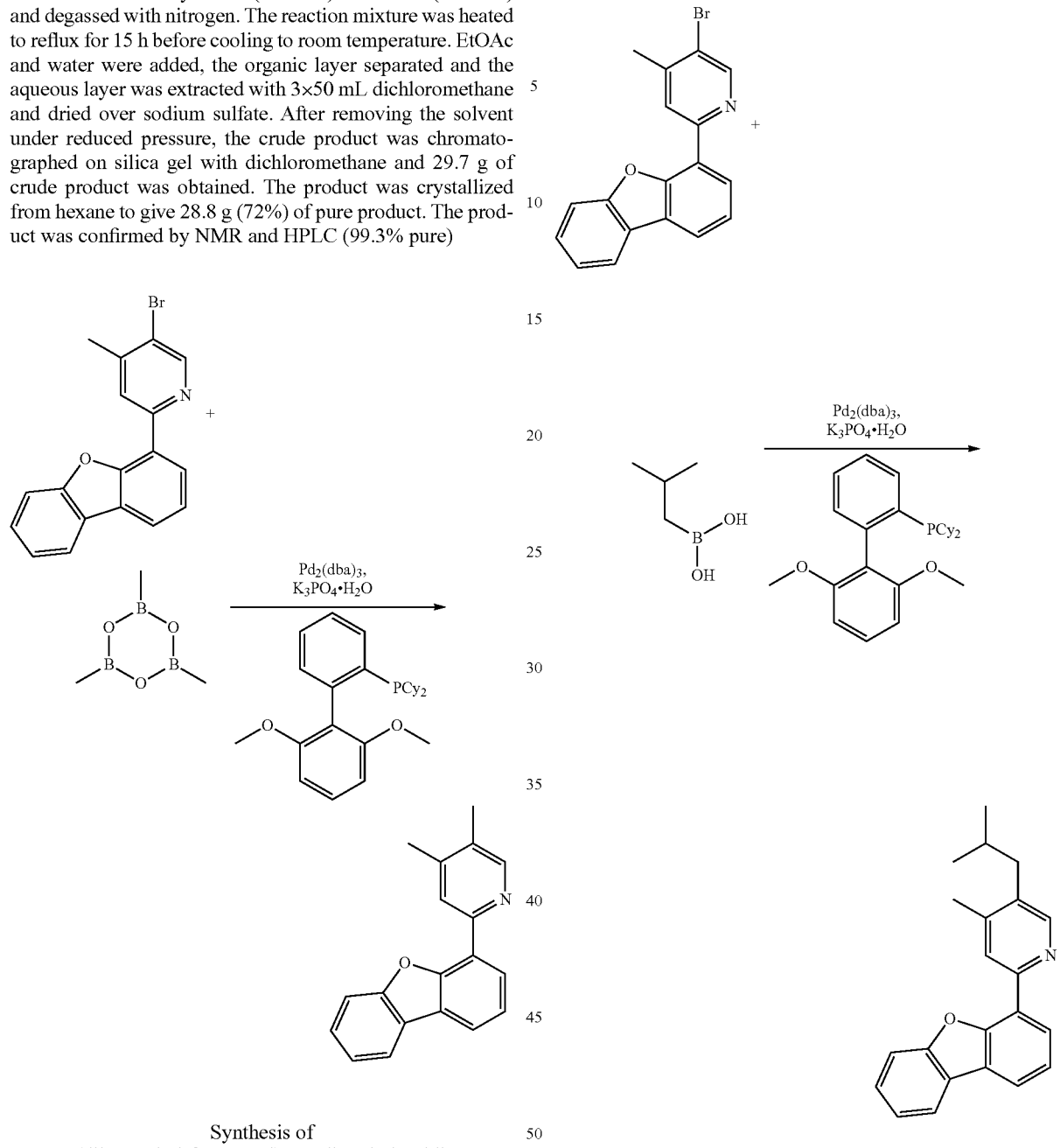

Synthesis of 2-(dibenzo[b,d]furan-4-yl)-4,5-dimethylpyridine

5-Bromo-2-(dibenzo[b,d]furan-4-yl)-4-methylpyridine (28.7 g, 85 mmol), dicyclohexyl(2',6'-dimethoxy-[1,1'-biphenyl]-2-yl)phosphine (1.394 g, 3.39 mmol) and potassium phosphate monohydrate (58.6 g, 255 mmol) were added to toluene (500 mL) and water (50 mL) and degassed for 20 min. Trimethylboroxine (14.83 mL, 106 mmol) and $Pd_2(dba)_3$ (0.777 g, 0.849 mmol) were added and the reaction mixture heated to reflux overnight. After cooling, the organic layer was separated and the aqueous layer extracted 3×50 mL with EtOAc, dried over sodium sulfate and evaporated. The crude product was chromatographed on silica gel with 8/2 (v/v) dichloromethane/EtOAc in hexane to give 19.2 g of an off-white solid, which was recrystallized from heaxane to give 16.8 g (83%) of the product as white needles. The product was confirmed by NMR and HPLC (99.97% pure).

flask with dimethoxyethane (450 mL) and water (100 mL) and degassed with nitrogen. The reaction mixture was heated to reflux for 15 h before cooling to room temperature. EtOAc and water were added, the organic layer separated and the aqueous layer was extracted with 3×50 mL dichloromethane and dried over sodium sulfate. After removing the solvent under reduced pressure, the crude product was chromatographed on silica gel with dichloromethane and 29.7 g of crude product was obtained. The product was crystallized from hexane to give 28.8 g (72%) of pure product. The product was confirmed by NMR and HPLC (99.3% pure)

Synthesis of 2-(dibenzo[b,d]furan-4-yl)-5-isobutyl-4-methylpyridine

5-Bromo-2-(dibenzo[b,d]furan-4-yl)-4-methylpyridine (13.0 g, 38.3 mmol), isobutylboronic acid (11.7 g, 115 mmol), dicyclohexyl(2',6'-dimethoxy-[1,1'-biphenyl]-2-yl) phosphine (0.63 g, 1.53 mmol) and potassium phosphate monohydrate (22.1 g, 96 mmol) were mixed in water (10 mL) and toluene (210 mL). The system was degassed for 20 min. with nitrogen and $Pd_2(dba)_3$ (0.35 g, 0.38 mmol) was then added and the system was refluxed overnight. After cooling to room temperature, the reaction mixture was filtered through a small plug of silica gel and eluted with dicloromethane. The filtrated was concentrated and then crystallized from hexane to give 2-(dibenzo[b,d]furan-4-yl)-5-isobutyl-4-methylpyridine (9.0 g, 74%).

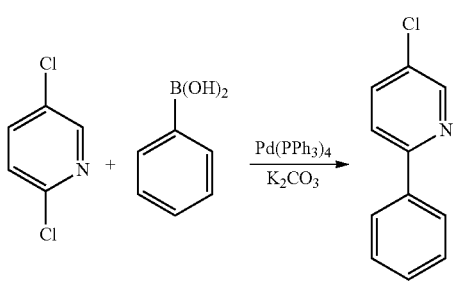

Synthesis of 5-chloro-2-phenylpyridine 2,5-Dichloropyridine (30 g, 203 mmol), phenylboronic acid (24.72 g, 203 mmol) and potassium carbonate (84 g, 608 mmol) were added to dimethoxyethane (500 mL) and water (100 mL). The reaction mixture was degassed with nitrogen for 20 min, and Pd(PPh$_3$)$_4$ (2.3 g, 2.0 mmol) was added and reaction mixture was allowed to reflux for 18 h. The reaction was cooled to room temperature, the aqueous layer removed and dimethoxyethane was concentrated to dryness by rotary evaporation under vacuum. The residue was dissolved in DCM and passed through a silica gel plug, eluting with DCM. The solvent was removed and the crude product was chromatographed on silica with 40/60 (v/v) DCM/hexane to 50/50 (v/v) DCM/hexane to yield 28 g (73%) of the product as a white solid (HPLC purity: 99.7%).

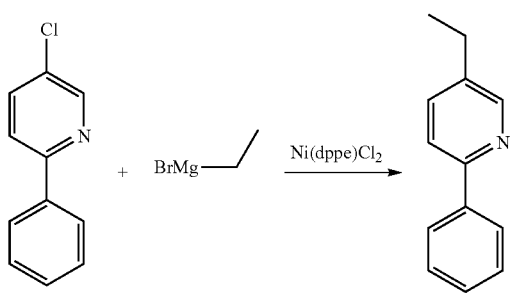

Synthesis of 5-ethyl-2-phenylpyridine

5-Chloro-2-phenylpyridine (16 g, 84 mmol) and Ni(dppe)Cl$_2$ (0.891 g, 1.687 mmol) were added to 300 mL of THF and the reaction mixture was degassed with nitrogen for 20 min. before being cooled to 0° C. Ethylmagnesium bromide (169 mL, 169 mmol) was added dropwise over a period of 60 min. and the reaction mixture stirred for and additional 3 h at before warming to room temperature overnight. The reaction mixture was recooled to 0° C. and quenched with 250 mL of water, extracted with EtOAc and the organic layer dried over sodium sulfate and filtered. The crude material was chromatographed on silica with 95/5 hexane/EtOAc to give 2.9 g (19%) of 5-ethyl-2-phenylpyridine as a white solid.

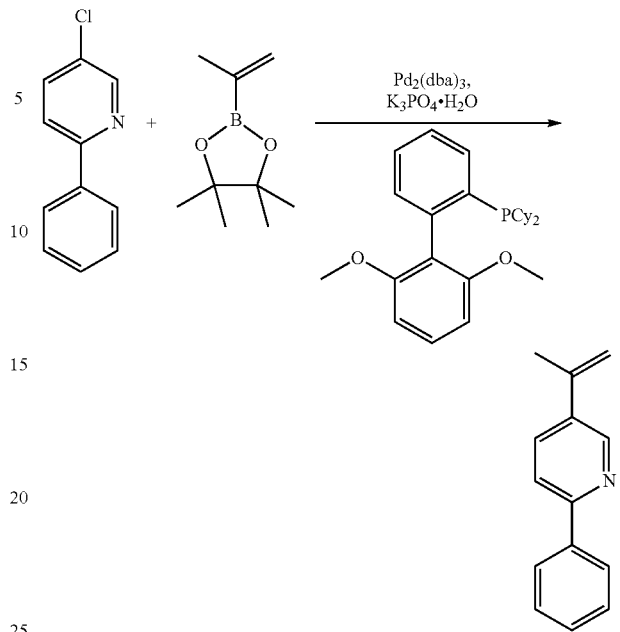

Synthesis of 2-phenyl-5-(prop-1-en-2-yl)pyridine

To a 1 L round bottom flask was added 5-chloro-2-phenylpyridine (10.15 g, 53.5 mmol), dicyclohexyl(2',6'-dimethoxy-[1,1'-biphenyl]-2-yl)phosphine (1.8 g, 4.3 mmol), potassium phosphate tribasic monohydrate (37.0 g, 161 mmol) with toluene (200 mL) and water (20 mL). The reaction mixture was degassed with nitrogen for 20 mins. 4,4,5,5-tetramethyl-2-(prop-1-en-2-yl)-1,3,2-dioxaborolane (12.07 mL, 64.2 mmol) and Pd$_2$(dba)$_3$ (0.980 g, 1.070 mmol) were added and the reaction mixture was refluxed for 18 h. The aqueous layer was removed and the organic layer was concentrated to dryness. The crude product was chromatographed on silica gel with 0-20% EtOAc in hexane to yield 11 g of the desired product (HPLC purity: 95%). The product was confirmed by GC/MS.

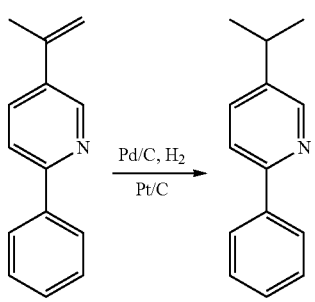

Synthesis of 2-phenyl-5-isopropylpyridine

2-Phenyl-5-(prop-1-en-2-yl)pyridine (11 g, 56.3 mmol) was added to a hydrogenator bottle containing EtOH (150 mL). The reaction mixture was degassed by bubbling N$_2$ for 10 min. Pd/C (0.60 g, 5.63 mmol) and Pt/C (0.55 g, 2.82 mmol) were added to the reaction mixture. The reaction mixture was placed on the Parr hydrogenator for 1.5 h. The reaction mixture was filtered on a tightly packed Celite® bed and washed with dichloromethane. The solvent was removed on rotoevaporator and GC/MS confirmed complete conversion. The crude product was adsorbed on Celite® for column chromatography. The crude product was chromatographed on silica gel with 10% EtOAc in hexane to yield 6 g (54%) of 2-phenyl-5-isopropylpyridine (HPLC purity: 100%). The product was confirmed by GC/MS.

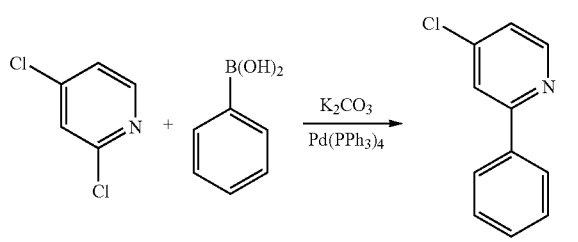

Synthesis of 4-chloro-2-phenylpyridine

A 1 L round bottom flask was charged with 2,4-dichloropyridine (30 g, 203 mmol), phenylboronic acid (24.7 g, 203 mmol), potassium carbonate (84 g, 608 mmol), Pd(PPh$_3$)$_4$ (2.3 g, 2.0 mmol), dimethoxyethane (500 mL) and water (150 mL). The mixture was degassed and heated to reflux for 20 h. After cooling, the aqueous layer was extracted with EtOAc; the organic portion was combined and subjected to column chromatography (SiO$_2$, 5% EtOAc in hexane to 10% EtOAc in hexane) to give 34 g (88%) of 4-chloro-2-phenylpyridine. The product was confirmed by GC/MS and NMR.

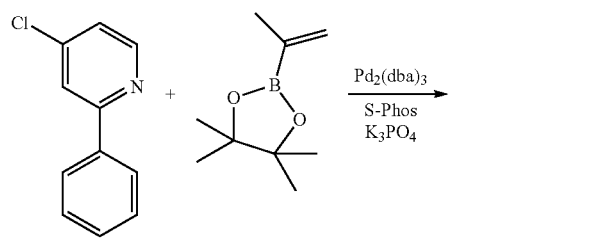

Synthesis of 2-phenyl-4-(prop-1-en-2yl)pyridine

4-Chloro-2-phenylpyridine (14 g, 73.8 mmol) and potassium phosphate (51.0 g, 221 mmol) were dissolved in 300 mL of toluene and 30 mL of water. The reaction was purged with nitrogen for 20 minutes and then 4,4,5,5-tetramethyl-2-(prop-1-en-2-yl)-1,3,2-dioxaborolane (16.65 mL, 89 mmol), Pd$_2$(dba)$_3$ (1.35 g, 1.48 mmol) and S-Phos (2.42 g, 5.91 mmol) were added. The reaction was brought to reflux for 18 h. After cooling, 100 mL of water was added, separated and the aqueous layer extracted twice with 100 mL of ethyl acetate. The organic layers were passed through a plug of silica gel, eluting with DCM. After evaporation of the solvent, the crude product was subjected to column chromatography (SiO$_2$, 5% EtOAc in hexane to 10% EtOAc in hexane) to get 13.5 g (90%) of 2-phenyl-4-(prop-1-en-2yl)pyridine.

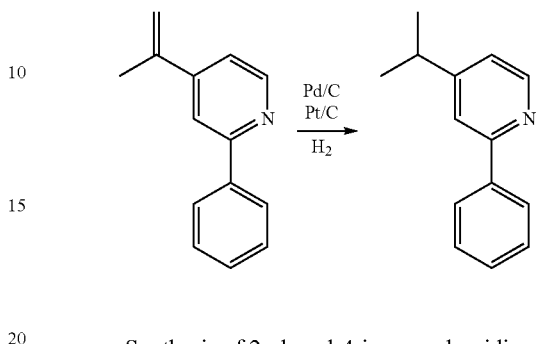

Synthesis of 2-phenyl-4-isopropylpyridine

2-Phenyl-4-(prop-1-en-2-yl) pyridine (13.5 g, 69.1 mmol) was added to a hydrogenator bottle containing EtOH (150 mL). The reaction mixture was degassed by bubbling with nitrogen for 10 min. Pd/C (0.736 g, 6.9 mmol) and Pt/C (0.674 g, 3.5 mmol) was added to the reaction mixture. The reaction mixture was placed on the Parr hydrogenator for 2 h. The reaction mixture was filtered on a tightly packed Celite® bed and washed with dichloromethane. The solvent was removed on a rotary evaporator and GC/MS confirmed complete conversion. The crude product was adsorbed on Celite® for column chromatography. The crude product was chromatographed on silica gel with 10% EtOAc in hexane to yield 10 g (75%) of 2-phenyl-4-isopropylpyridine (HPLC purity: 99.8%). The product was confirmed by GC/MS.

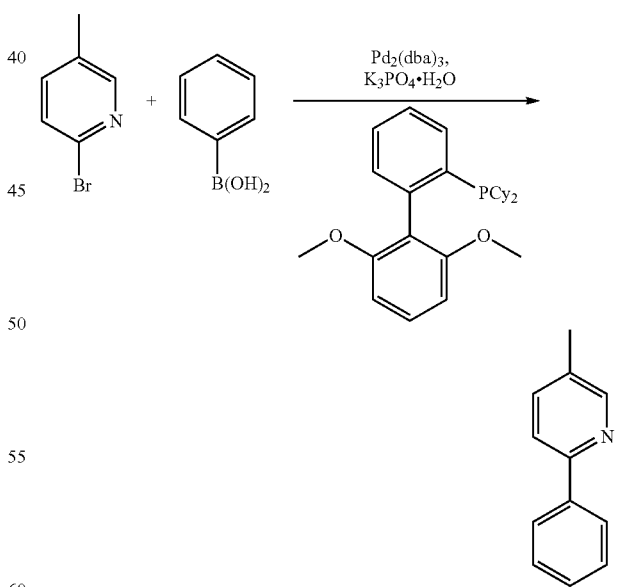

Synthesis of 5-methyl-2-phenylpyridine

2-Bromo-5-methylpyridine (30 g, 174 mmol), phenylboronic acid (25.5 g, 209 mmol), dicyclohexyl(2',6'-dimethoxy-[1,1'-biphenyl]-2-yl)phosphine (2.86 g, 6.98 mmol) and potassium phosphate tribasic monohydrate (120 g, 523 mmol) were added to toluene (600 mL) and water (60 mL). The reaction mixture was degassed with nitrogen for 20 min. Pd$_2$(dba)$_3$ (3.19 g, 3.49 mmol) was added and the reaction mixture was refluxed for 18 h. After cooling, the organic layer was separated and the aqueous layer extracted with 3×50 mL dichloromethane, dried over sodium sulfate and evaporated. The crude product was chromatographed on silica gel with 75/25 (v/v) hexane/EtOAc and then distilled on a Kugelrohr apparatus (150° C., 100 mbar) to give 26 g (88%) of 5-methyl-2-phenylpyridine as a white solid. The product was confirmed by NMR and GC/MS. HPLC purity: 99.2%.

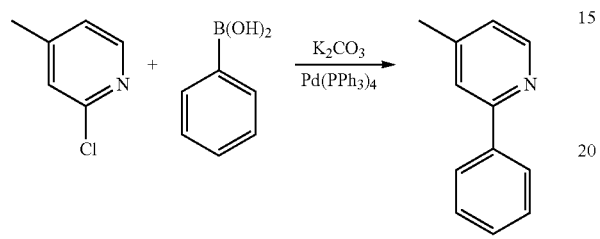

Synthesis of 4-methyl-2-phenylpyridine

A 1 L round bottom flask was charged with 2-chloro-4-methylpyridine (25 g, 196 mmol), phenylboronic acid (23.9 g, 196 mmol), potassium carbonate (81 g, 588 mmol), Pd(PPh$_3$)$_4$ (2.3 g, 1.9 mmol), dimethoxyethane (500 mL) and water (150 mL). The reaction mixture was degassed with nitrogen and heated to reflux for 22 h. After cooling, the aqueous layer was extracted with EtOAc; the organic portion was combined and subjected to column chromatography (SiO$_2$, 5% EtOAc in hexane to 10% EtOAc in hexane) to give 28 g (78%) of 4-methyl-2-phenylpyridine. The product was confirmed by NMR and GC/MS.

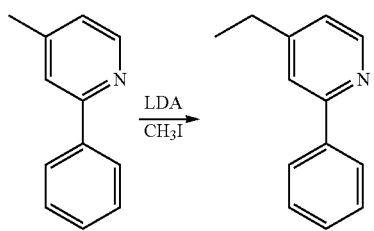

Synthesis of 4-ethyl-2-phenylpyridine

To 4-methyl-2-phenylpyridine (8 g, 47.3 mmol) in dry THF (150 mL) at −78° C. was added dropwise lithium diisopropylamide (LDA) (30.7 mL, 61.5 mmol). The dark solution was stirred for 3 h at −78° C. and then CH$_3$I was added (4.1 mL, 66.2 mmol) dropwise. The reaction mixture was allowed to slowly warm to room temperature overnight. Ammonium chloride solution and EtOAc were added and the reaction transferred to a reparatory funnel. The layers were separated, washing the aqueous twice with EtOAc and combined organics once with water. After removal of the solvent, the crude product was chromatographed on silica gel with 9/1 (v/v) hexane/EtOAc to give 5.5 g (63.5%) of 4-ethyl-2-phenylpyridine. HPLC purity: 99.0%.

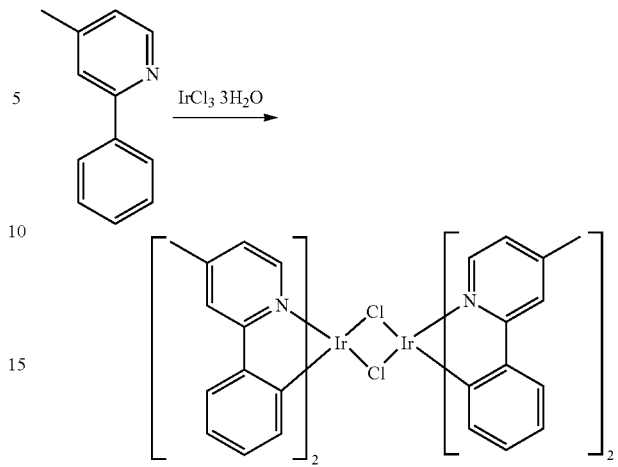

Synthesis of 4-methyl-2-phenylpyridine chloro-bridged dimer

To a 500 mL round-bottom flask was added 4-methyl-2-phenylpyridine (7 g, 41 mmol) and iridium(III) chloride hydrate (4.86 g, 13.79 mmol) with 2-ethoxyethanol (90 mL) and water (30 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 7.5 g (90%) of the desired product. The product was used without further purification.

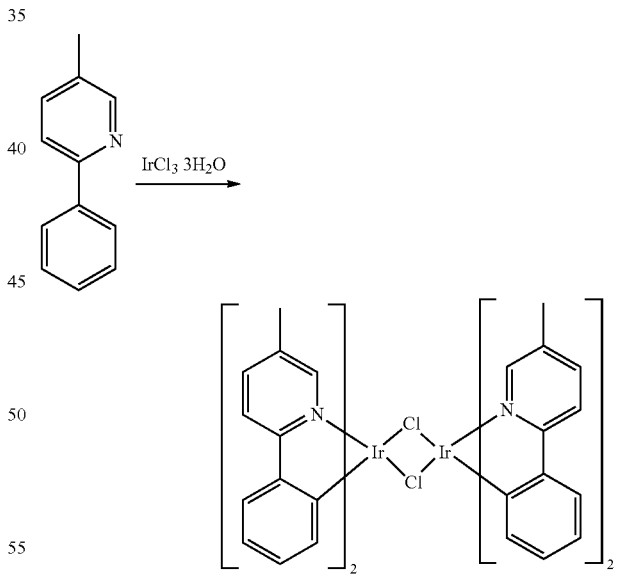

Synthesis of 5-methyl-2-phenylpyridine chloro-bridged dimer

To a 500 mL round bottom flask was added 5-methyl-2-phenylpyridine (12 g, 70.9 mmol) and iridium(III) chloride hydrate (7.1 g, 20.3 mmol) with 2-ethoxyethanol (100 mL) and water (33.3 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 11.0 g (96%) of the desired product. The product was used without further purification.

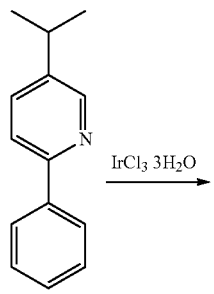

Synthesis of 2-phenyl-5-isopropylpyridine chloro-bridged dimer

To a 500 mL round-bottom flask was added 5-isopropyl-2-phenylpyridine (6.0 g, 30.4 mmol) and iridium(III) chloride hydrate (3.6 g, 10.1 mmol) with 2-ethoxyethanol (100 mL) and water (33.3 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 7 g (100%) of the desired product. The product was used without further purification.

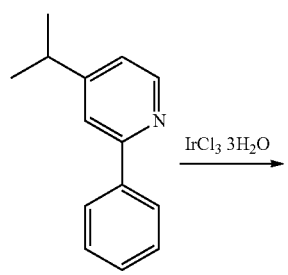

Synthesis of 2-phenyl-4-isopropylpyridine chloro-bridged dimmer

To a 500 mL round-bottom flask was added 4-isopropyl-2-phenylpyridine (8.0 g, 40.6 mmol) and iridium(III) chloride hydrate (7.4 g, 20.3 mmol) with 2-ethoxyethanol (90 mL) and water (30 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 6.1 g (95%) of the desired product. The product was used without further purification.

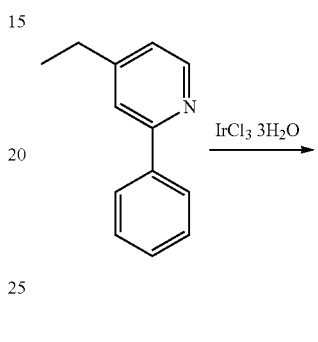

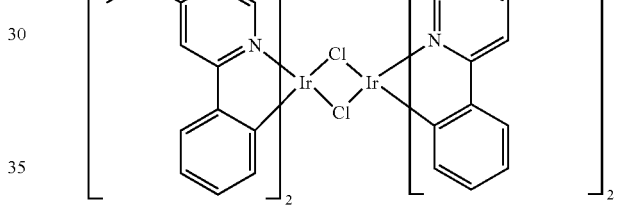

Synthesis of 4-ethyl-2-phenylpyridine chloro-bridged dimmer

To a 500 mL round-bottom flask was added 4-isopropyl-2-phenylpyridine (5.5 g, 30.0 mmol) and iridium(III) chloride hydrate (5.8 g, 16.5 mmol) with 2-ethoxyethanol (90 mL) and water (30 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 6.5 g (72%) of the desired product. The product was used without further purification.

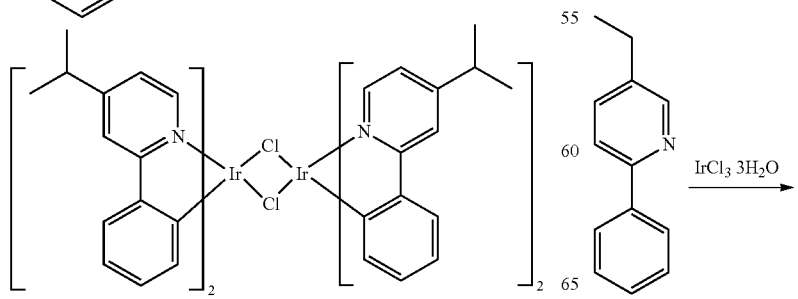

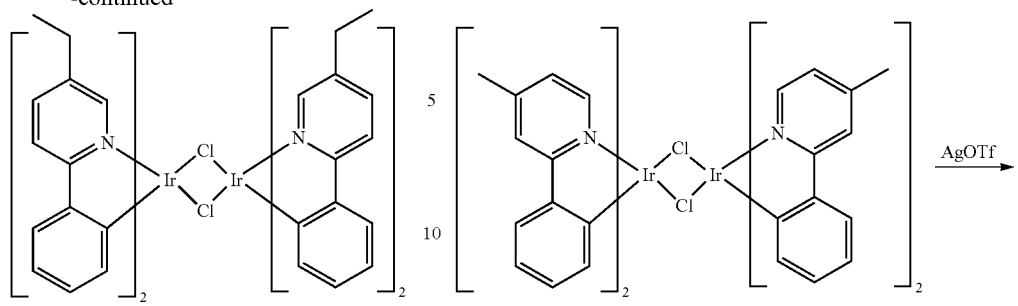
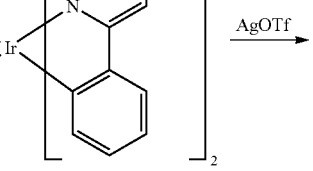

Synthesis of 5-ethyl-2-phenylpyridine chloro-bridged dimer

To a 500 mL round bottom flask was added 5-ethyl-2-phenylpyridine (2.9 g, 15.7 mmol) and iridium(III) chloride hydrate (1.8 g, 5.2 mmol) with 2-ethoxyethanol (60 mL) and water (20 mL) under a nitrogen atmosphere. The reaction mixture was refluxed at 130° C. for 18 h. The resulting precipitate was filtered and washed with methanol (3-4 times) and hexane (3-4 times). The product obtained was dried to give 2.45 g (89.3%) of the desired product. The product was used without further purification.

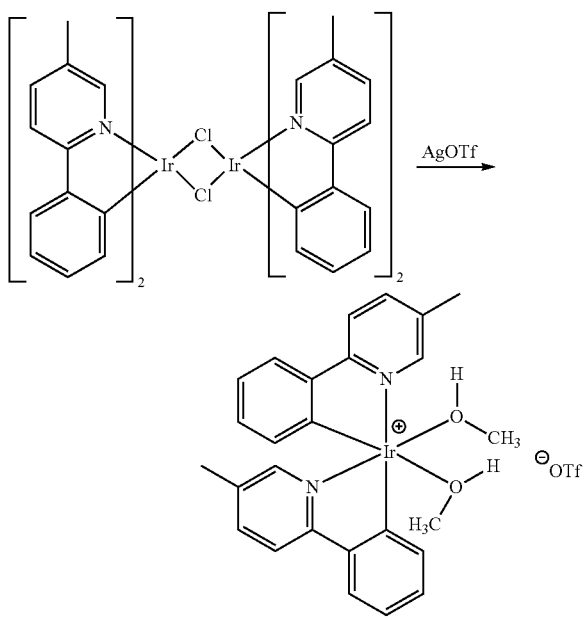

Synthesis of 4-methyl-2-phenylpyridine iridium trifluoromethanesulfonate salt The iridium dimer (7.5 g, 6.6 mmol) was dissolved in 600 mL of dichloromethane. In a separate flask, silver(I) trifluoromethanesulfonate (3.5 g, 13.8 mmol) was dissolved in MeOH (300 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 10 g (100%) of product as a brownish green solid. The product was used without further purification.

Synthesis of 5-methyl-2-phenylpyridine iridium trifluoromethanesulfonate salt The iridium dimer (11 g, 9.8 mmol) was suspended in 600 mL of dichloromethane. In a separate flask, silver(I) trifluoromethanesulfonate (5.3 g, 20.5 mmol) was dissolved in MeOH (300 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 15 g (100%) of product as a brownish green solid. The product was used without further purification.

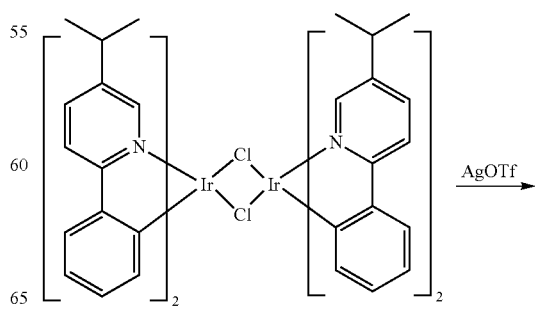

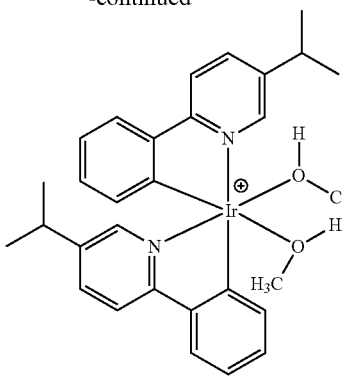

Synthesis of 2-phenyl-5-isopropylpyridine iridium trifluoromethanesulfonate salt The iridium dimer (5.3 g, 4.3 mmol) was dissolved in 500 mL of dichloromethane. In a separate flask, silver(I) trifluoromethanesulfonate (2.3 g, 8.9 mmol) was dissolved in MeOH (250 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 6.9 g (100%) of product as a brownish solid. The product was used without further purification.

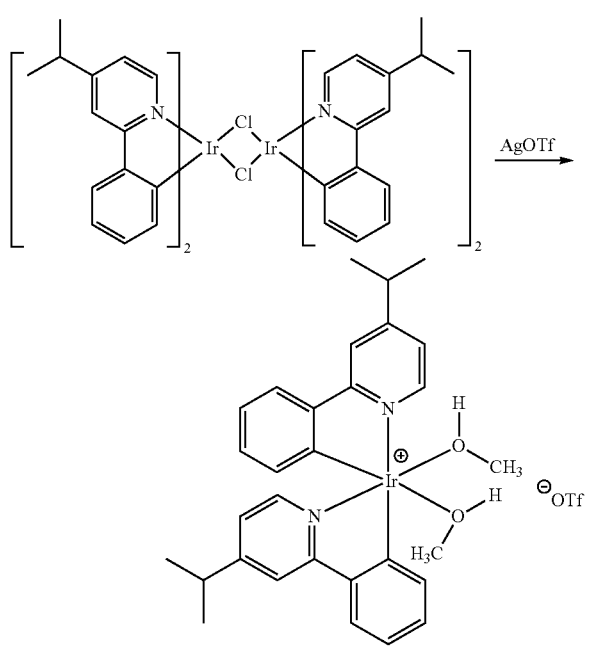

Synthesis of 2-phenyl-4-isopropylpyridine iridium trifluoromethanesulfonate salt The iridium dimer (6.2 g, 4.94 mmol) was dissolved in 500 mL of dichloromethane. In a separate flask, silver(I) trifluoromethanesulfonate (2.7 g, 10.4 mmol) was dissolved in MeOH (250 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 7.8 g (100%) of product as a brownish green solid. The product was used without further purification.

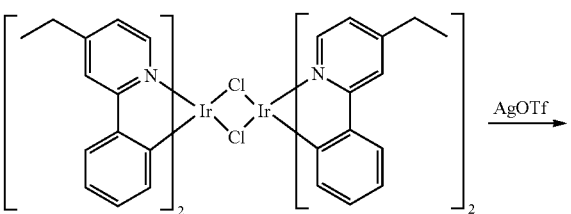

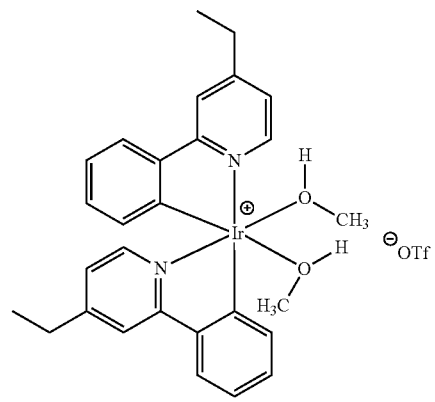

Synthesis of 4-ethyl-2-phenylpyridine iridium trifluoromethanesulfonate salt The iridium dimer (6.8 g, 5.7 mmol) was dissolved in 500 mL of dichloromethane. In a separate flask, silver(I) trifluoromethanesulfonate (3.2 g, 12.5 mmol) was dissolved in MeOH (250 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 5.5 g (63%) of product as a brownish green solid. The product was used without further purification.

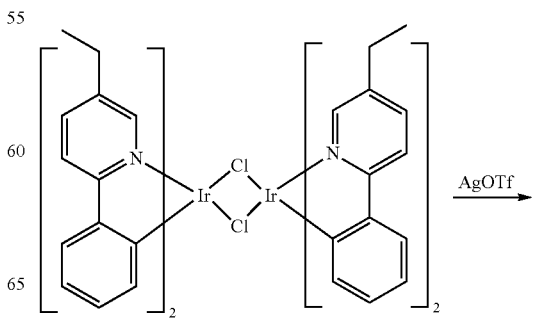

-continued

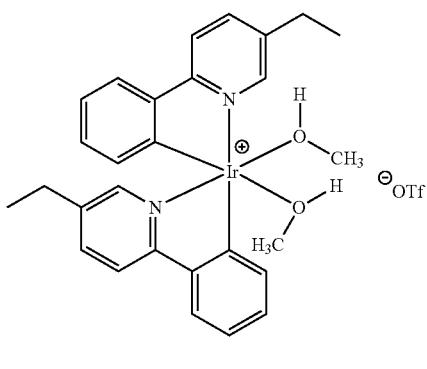

Synthesis of 5-ethyl-2-phenylpyridine iridium trifluoromethanesulfonate salt The iridium dimer (2.8 g, 2.4 mmol) was suspended in 500 mL of dichloromethane. In a separate flask, silver(I) trifluoromethanesulfonate (1.3 g, 4.91 mmol) was dissolved in MeOH (250 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 3.6 g (100%) of product as a brownish green solid. The product was used without further purification.

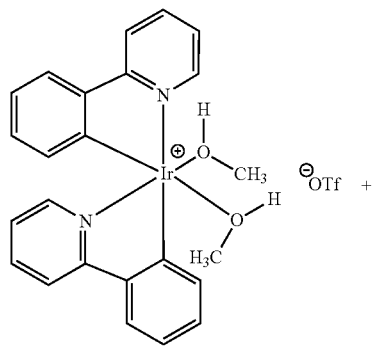

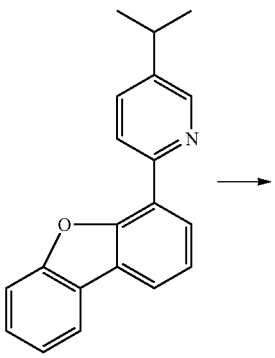

-continued

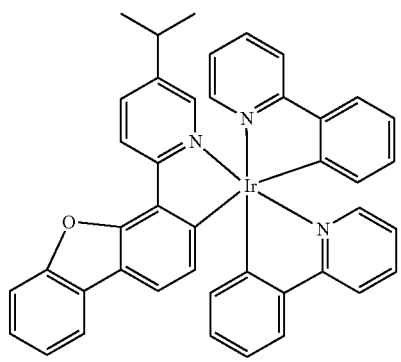

Synthesis of Compound 53

A mixture of the appropriate iridium trifluoromethanesulfonate complex (3.5 g, 4.9 mmol) and 2-(dibenzo[b,d]furan-4-yl)-5-isopropylpyridine (3.5 g, 12.18 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with 1/1 (v/v) dichloromethane/hexane to yield 1.3 g (33%) of Compound 53 as a yellow solid. The product was confirmed by HPLC (99.5% pure) and LC/MS.

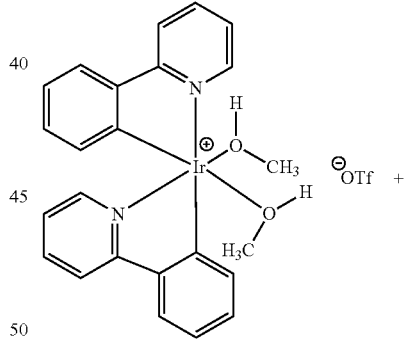

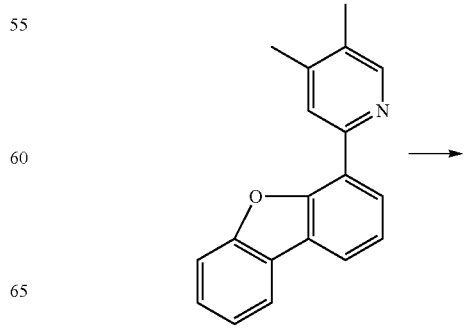

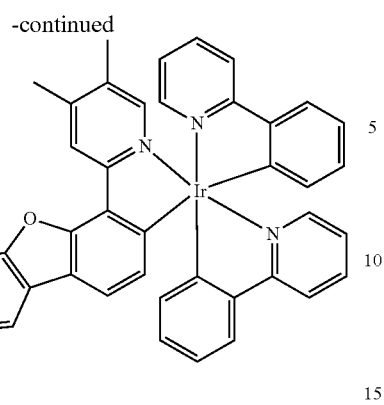

Synthesis of Compound 157

A mixture of the appropriate iridium trifluoromethanesulfonate complex (2.5 g, 3.50 mmol) and 2-(dibenzo[b,d]furan-4-yl)-4,5-dimethylpyridine (2.5 g, 9.15 mmol)) in EtOH (25 mL) and MeOH (25 mL) was refluxed for 20 h under inert atmosphere. The reaction mixture was refluxed for 24 h. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane to yield a mixture of fac- and mer-isomers by LC/MS. The mixture was isomerized to the fac-isomer in a Rayonet at 350 nm in DMSO. The crude product was chromatographed on silica gel with 1/1 dichloromethane/hexane to yield 1.4 g (52%) of Compound 157 as a yellow solid. The product was confirmed by HPLC (98.7% pure) and LC/MS.

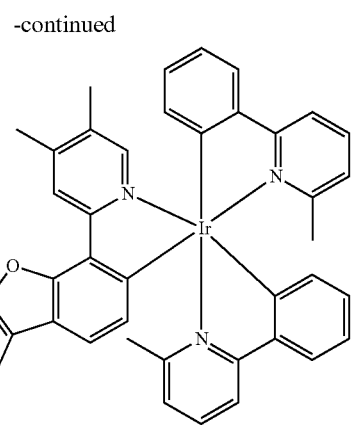

Synthesis of Compound 158

A mixture of the appropriate iridium trifluoromethanesulfonate complex (2.5 g, 3.37 mmol) and 2-(dibenzo[b,d]furan-4-yl)-4,5-dimethylpyridine (2.5 g, 9.15 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane and dried to yield 2.7 g (100%) of Compound 158 as a yellow solid. The product was confirmed by HPLC (99.4% pure) and LC/MS.

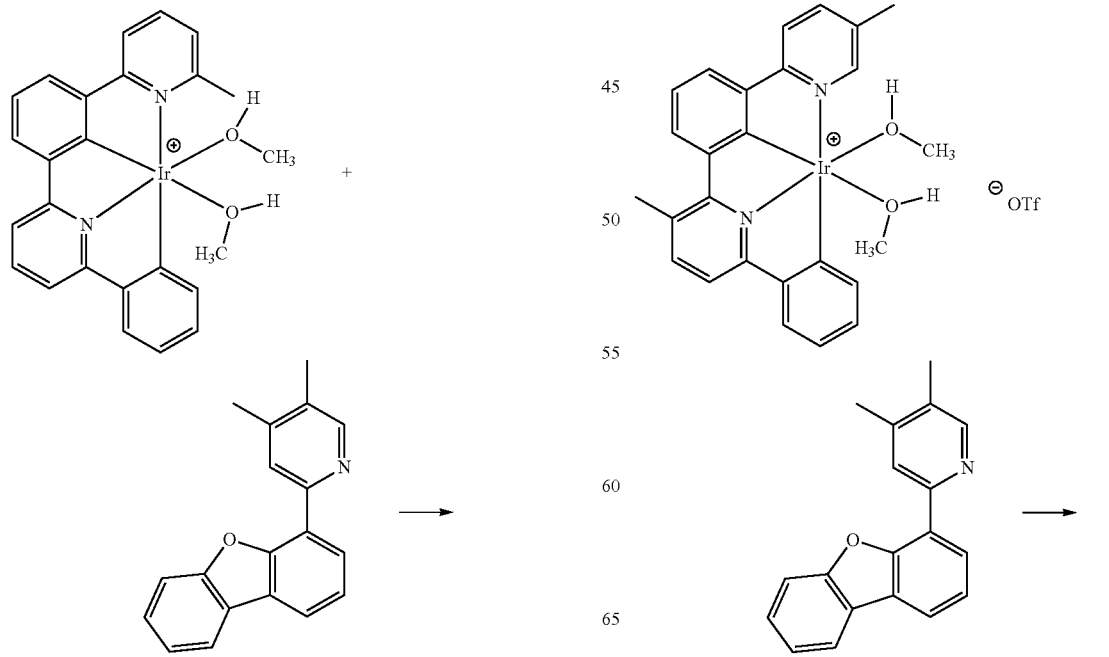

-continued

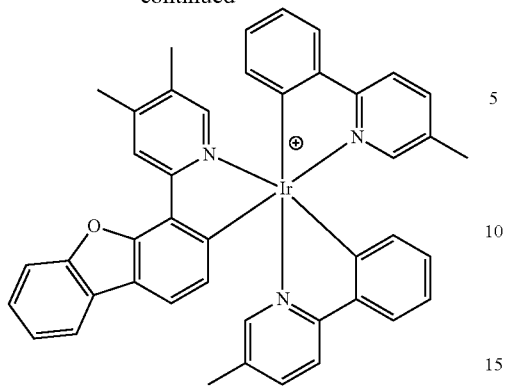

Synthesis of Compound 159

A mixture of the appropriate iridium trifluoromethanesulfonate complex (3.0 g, 4.04 mmol) and 2-(dibenzo[b,d]furan-4-yl)-4,5-dimethylpyridine (3.0 g, 10.98 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solubility of the desired product was very poor. Large amount of solvent was used to elute the product. The crude product was chromatographed on silica gel with 1/1 (v/v) dichloromethane/hexane and later 4/1 dichloromethane/hexane to yield 0.3 g of the product as a yellow solid. The product was confirmed by HPLC (99.9% pure) and LC/MS.

-continued

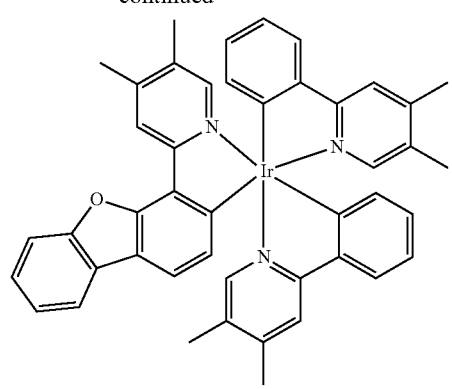

Synthesis of Compound 165

A mixture of the appropriate iridium trifluoromethanesulfonate complex (2.5 g, 3.25 mmol) and 2-(dibenzo[b,d]furan-4-yl)-4,5-dimethylpyridine (2.5 g, 9.15 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane and dried. The crude product was chromatographed on silica gel with 1/1 (v/v) dichloromethane/hexane to yield 1.2 g (43%) of Compound 165 as a yellow solid. The product was confirmed by HPLC (99.4% pure) and LC/MS.

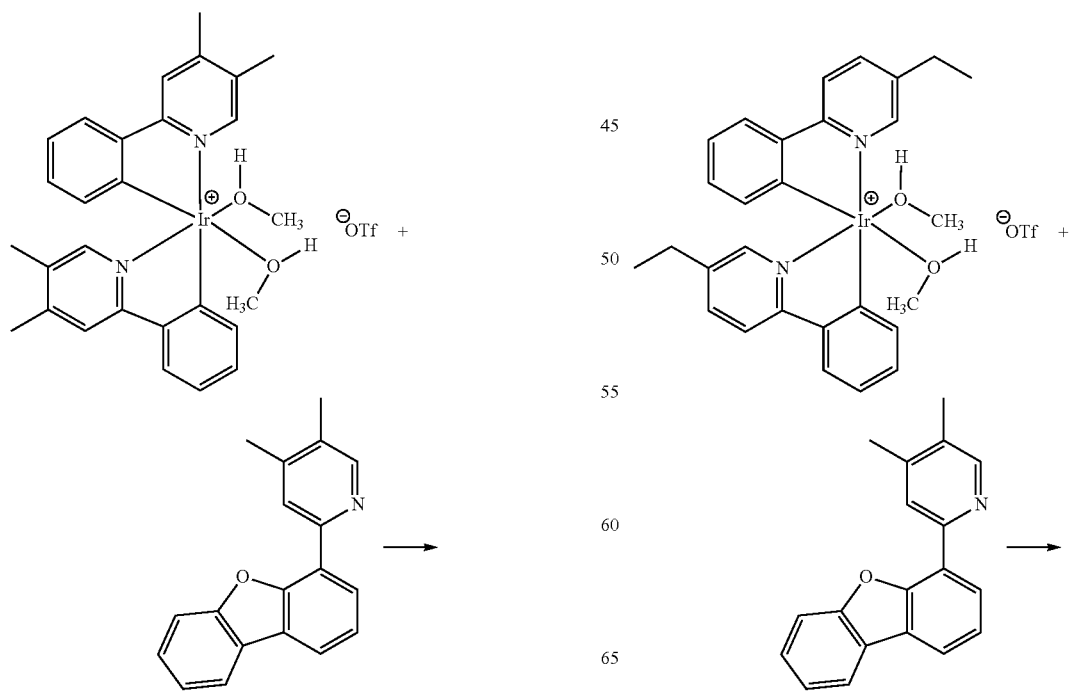

145
-continued

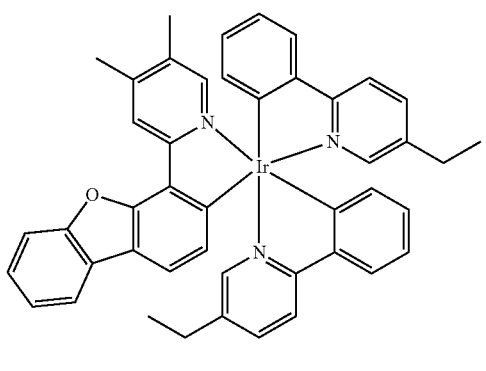

Synthesis of Compound 174

A mixture of the appropriate iridium trifluoromethanesulfonate complex (3.6 g, 4.68 mmol) and 2-(dibenzo[b,d]furan-4-yl)-4,5-dimethylpyridine (3.6 g, 13.17 mmol) in EtOH (50 mL) and MeOH (50 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with 1/1 (v/v) dichloromethane/hexane to yield 0.8 g of product as a yellow solid was confirmed by HPLC (98.6% pure) and LC/MS.

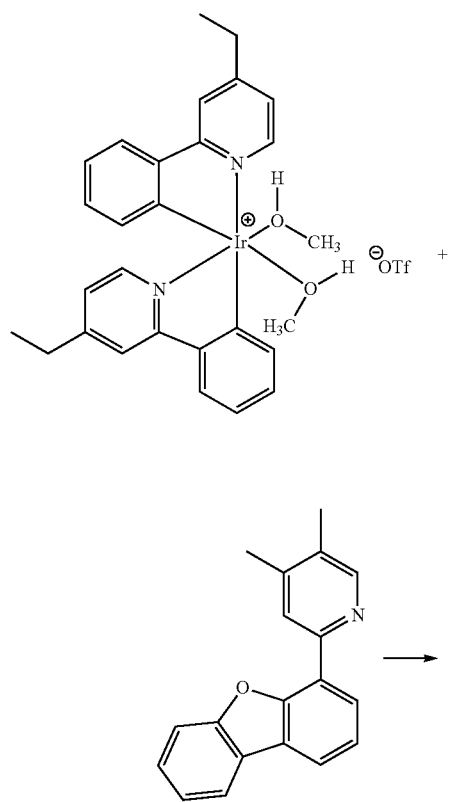

146
-continued

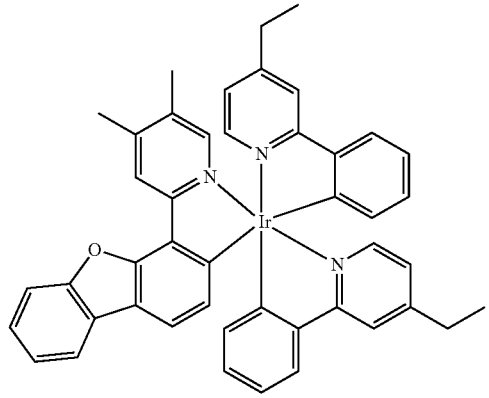

Synthesis of Compound 175

A mixture of the appropriate iridium trifluoromethanesulfonate complex (2.5 g, 3.25 mmol) and 2-(dibenzo[b,d]furan-4-yl)-4,5-dimethylpyridine (2.66 g, 9.74 mmol) in EtOH (30 mL) and MeOH (30 mL) was refluxed for 20 h under nitrogen atmosphere. The reaction mixture was cooled to room temperature, diluted with ethanol, Celite® was added and the mixture stirred for 10 min. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with 2/3 (v/v) THF/hexane to yield 0.8 g of product by HPLC. The product was recrystallized by slow evaporation of DCM from a 1/3 DCM/hexane solution to yield 0.6 g (22%) as a yellow crystalline solid. The product was confirmed by HPLC (99.4% pure) and LC/MS.

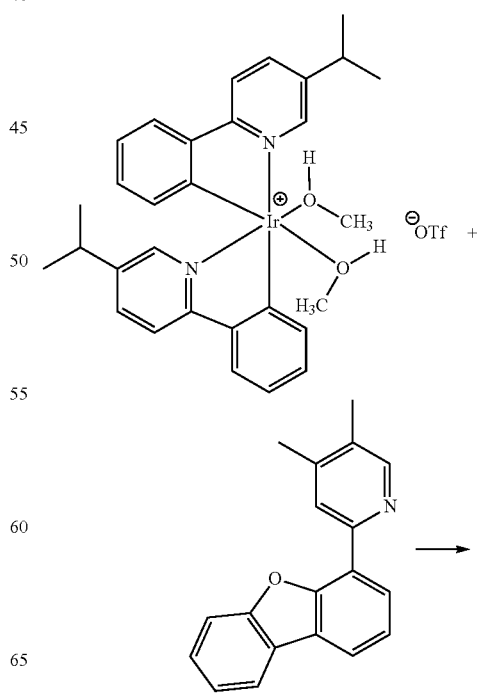

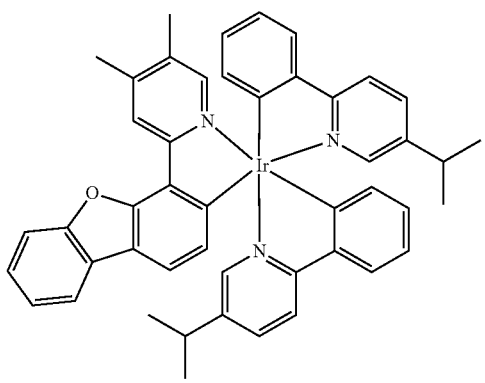

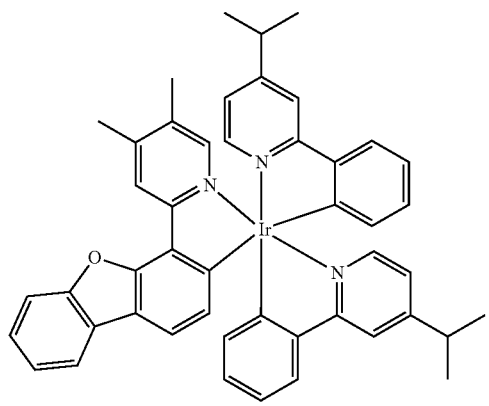

Synthesis of Compound 184

A mixture of the appropriate iridium trifluoromethanesulfonate complex (3.0 g, 3.76 mmol) and 2-(dibenzo[b,d]furan-4-yl)-4,5-dimethylpyridine (3.0 g, 10.98 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with 1/1 (v/v) dichloromethane/hexane to yield 2.1 g (65%) of product as a yellow solid. The product was confirmed by HPLC (99.8% pure) and LC/MS.

Synthesis of Compound 185

A mixture of the appropriate iridium trifluoromethanesulfonate complex (2.8 g, 3.51 mmol) and 2-(dibenzo[b,d]furan-4-yl)-4,5-dimethyl pyridine (2.88.0 g, 10.53 mmol) in EtOH (30 mL) and MeOH (30 mL) was refluxed for 20 h under $N_2$ atmosphere. The reaction mixture was cooled to room temperature, diluted with ethanol, Celite® was added and the mixture stirred for 10 min. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with 2/3 (v/v) dichloromethane/hexane to yield 2.1 g (69%) of product as a yellow solid. The product was confirmed by HPLC (99.9% pure) and LC/MS.

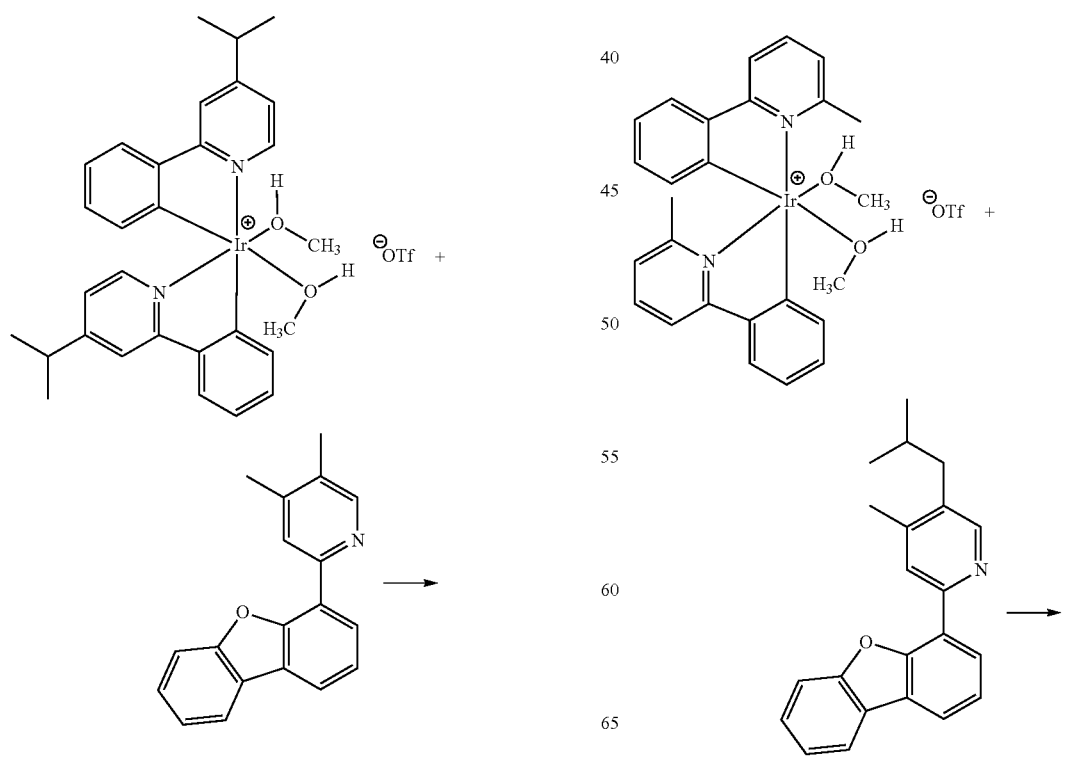

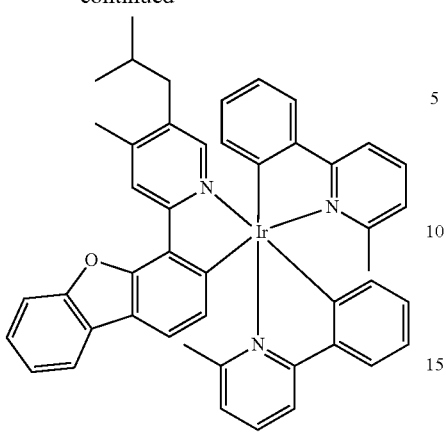

Synthesis of Compound 314

A mixture of the appropriate iridium trifluoromethanesulfonate complex (2.5 g, 3.37 mmol) and 2-(dibenzo[b,d]furan-4-yl)-5-isobutyl-4-methylpyridine (2.5 g, 7.93 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane and dried to yield 3.0 g (100%) of Compound 314 as a yellow solid. The product was confirmed by HPLC (99.6% pure) and LC/MS.

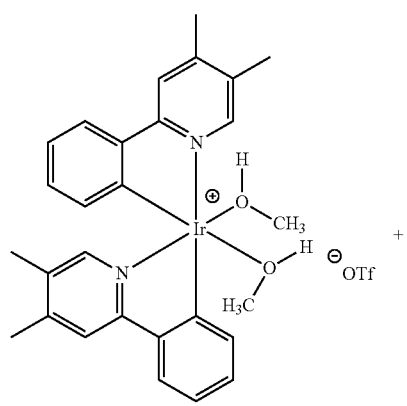

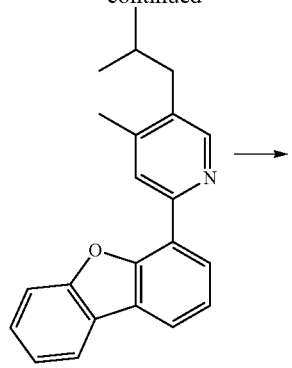

Synthesis of Compound 321

A mixture of the appropriate iridium trifluoromethanesulfonate complex (2.2 g, 2.86 mmol) and 2-(dibenzo[b,d]furan-4-yl)-5-isobutyl-4-methylpyridine (2.2 g, 6.98 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane. The crude product was chromatographed on silica gel with 1/1 (v/v) dichloromethane/hexane to yield 1.6 g (50%) of Compound 321 as a yellow solid. The product was confirmed by HPLC (99.0% pure) and LC/MS.

151

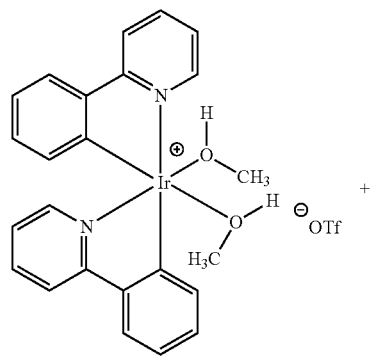

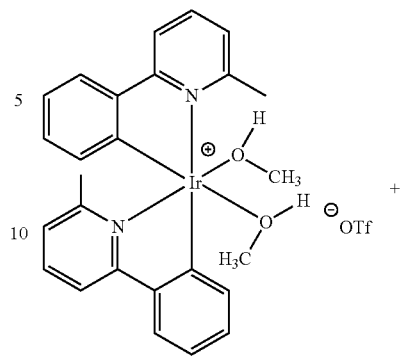

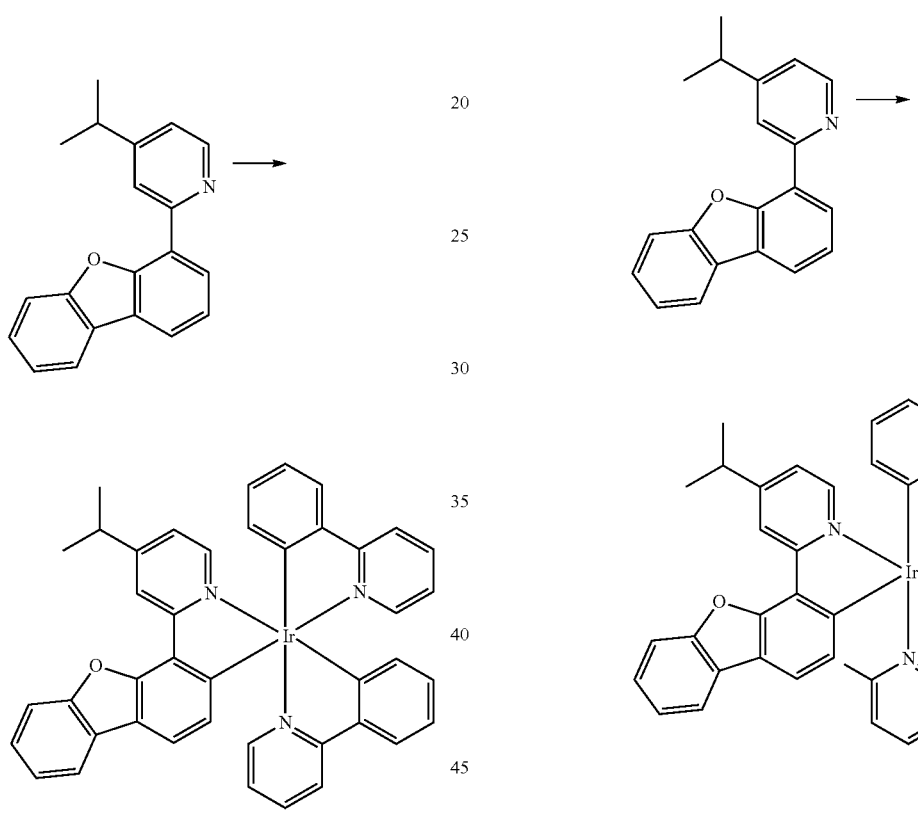

Synthesis of Compound 625

A mixture of the appropriate iridium trifluoromethanesulfonate complex (2.2 g, 3.08 mmol) and 2-(dibenzo[b,d]furan-4-yl)-4-isopropylpyridine (2.2 g, 7.66 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane and dried to yield 1.7 g (67%) of Compound 625 as a yellow solid. The product was confirmed by HPLC (99.8% pure) and LC/MS.

152

Synthesis of Compound 626

A mixture of the appropriate iridium trifluoromethanesulfonate complex (2.5 g, 3.37 mmol) and 2-(dibenzo[b,d]furan-4-yl)-4-isopropylpyridine (2.5 g, 8.70 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane and dried. The crude product was chromatographed on silica gel with 1/1 (v/v) dichloromethane/hexane to yield 2.5 g (89%) of Compound 626 as a yellow solid. The product was confirmed by HPLC (99.4% pure) and LC/MS.

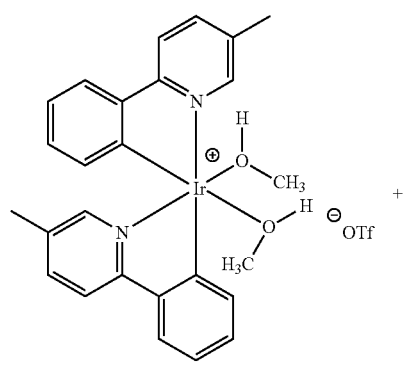

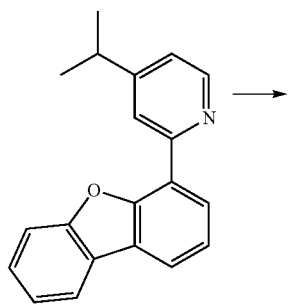 →

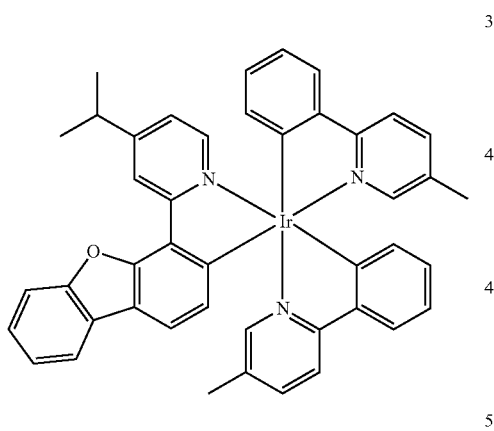

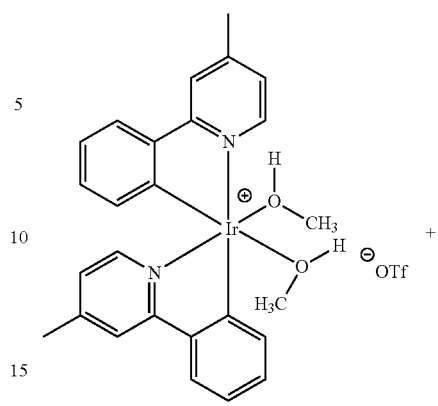

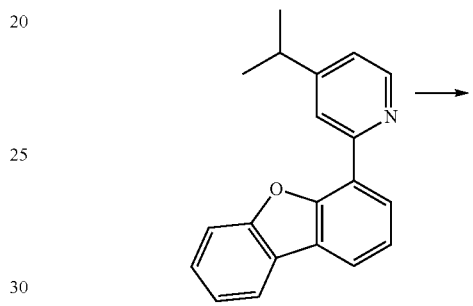 →

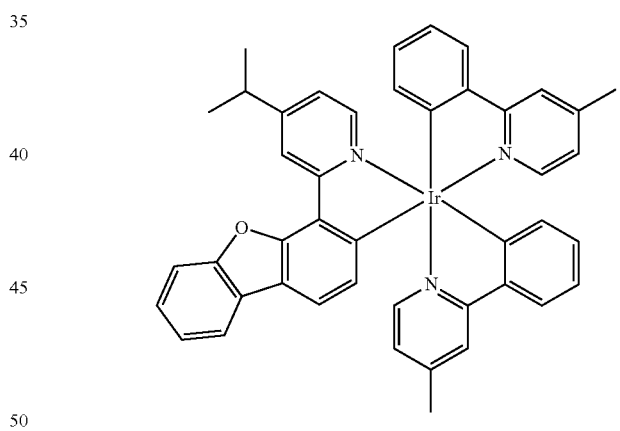

Synthesis of Compound 627

A mixture of the appropriate iridium trifluoromethane-sulfonate complex (3.0 g, 4.0 mmol) and 2-(dibenzo[b,d]furan-4-yl)-4-isopropylpyridine (3.0 g, 10.4 mmol in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with 1/1 (v/v) dichloromethane/hexane to yield 2.0 g (60%) of Compound 627 as a yellow solid. The product was confirmed by HPLC (99.9% pure) and LC/MS.

Synthesis of Compound 628

A mixture of the appropriate iridium trifluormethane-sulfonate complex (3.0 g, 4.0 mmol) and 2-(dibenzo[b,d]furan-4-yl)4-isopropylpyridine (3.0 g, 10.5 mmol) in EtOH (25 mL) and MeOH (25 mL) was refluxed for 24 h under nitrogen atmosphere. The reaction mixture was cooled to room temperature, diluted with ethanol, Celite® was added and the mixture stirred for 10 min. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with ⅔ (v/v) dichloromethane/hexane to yield 2.1 g (64%) of product as a yellow solid. The product was confirmed by HPLC (99.95% pure) and LC/MS.

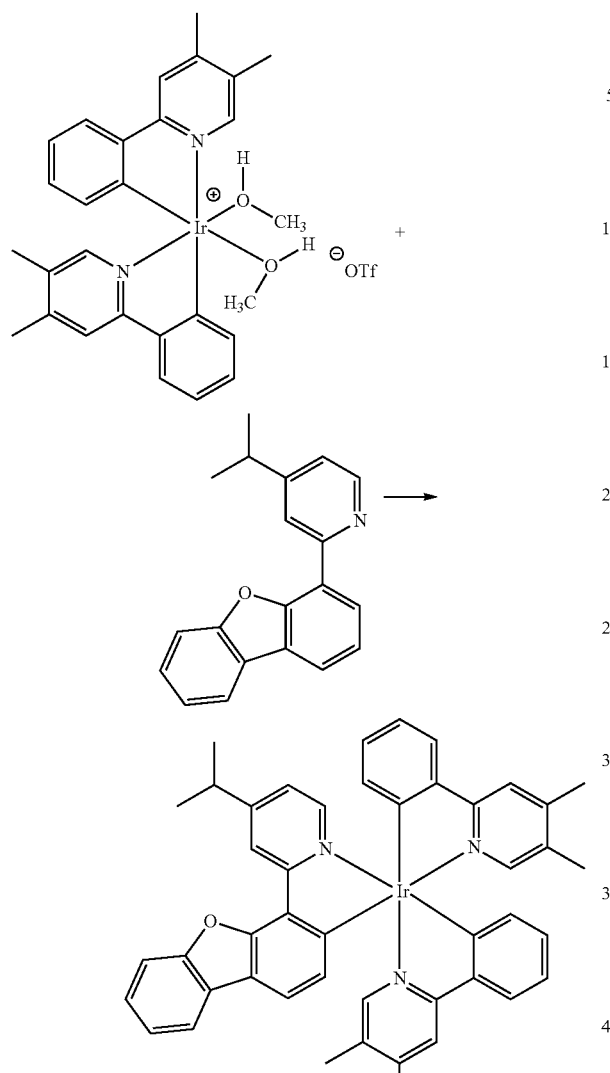

Synthesis of Compound 633

A mixture of the appropriate iridium trifluoromethanesulfonate complex (2.5 g, 3.25 mmol) and 2-(dibenzo[b,d]furan-4-yl)-4-isopropylpyridine (2.5 g, 8.70 mmol) in EtOH (25 mL) and MeOH (25 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The solvent was removed to half the volume and the product precipitated by addition of isopropanol and removing dichloromethane under reduced pressure. The filtered material was washed with isopropanol and hexane and dried. The crude product was chromatographed on silica gel with 1/1 (v/v) dichloromethane/hexane to yield 1.6 g (59%) of Compound 633 as a yellow solid. The product was confirmed by HPLC (99.7% pure) and LC/MS.

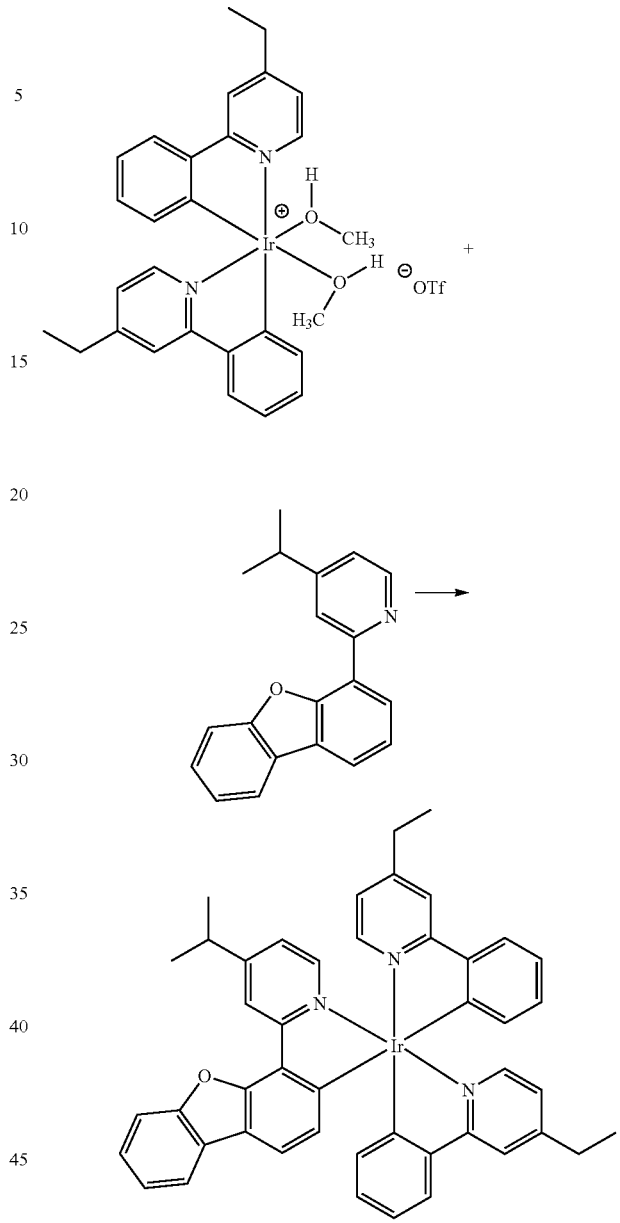

Synthesis of Compound 643

A mixture of the appropriate iridium trifluoromethanesulfonate complex (2.4 g, 3.12 mmol) and 2-(dibenzo[b,d]furan-4-yl)4-ethylpyridine (2.69 g, 9.35 mmol) in EtOH (30 mL) and MeOH (30 mL) was refluxed for 20 h under nitrogen atmosphere. The reaction mixture was cooled to room temperature, diluted with ethanol, Celite® was added and the mixture stirred for 10 min. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with ⅔ (v/v) dichloromethane/hexane to yield 1.3 g (50%) of product as a yellow solid. The product was confirmed by HPLC (100% pure) and LC/MS.

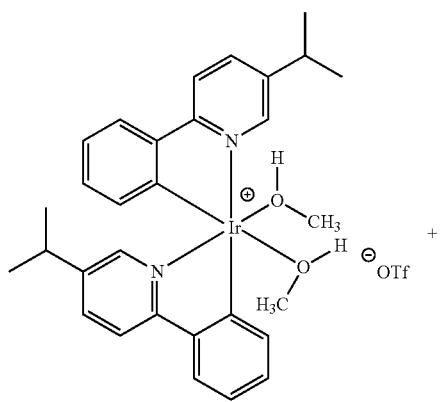

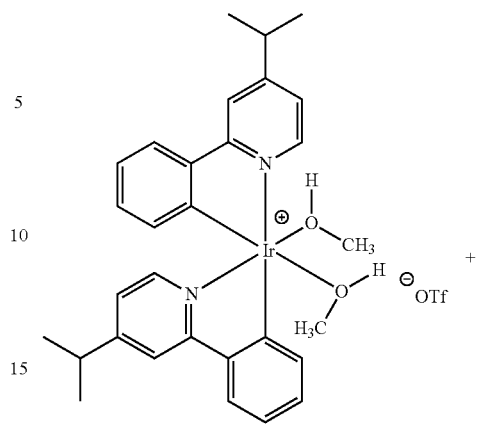

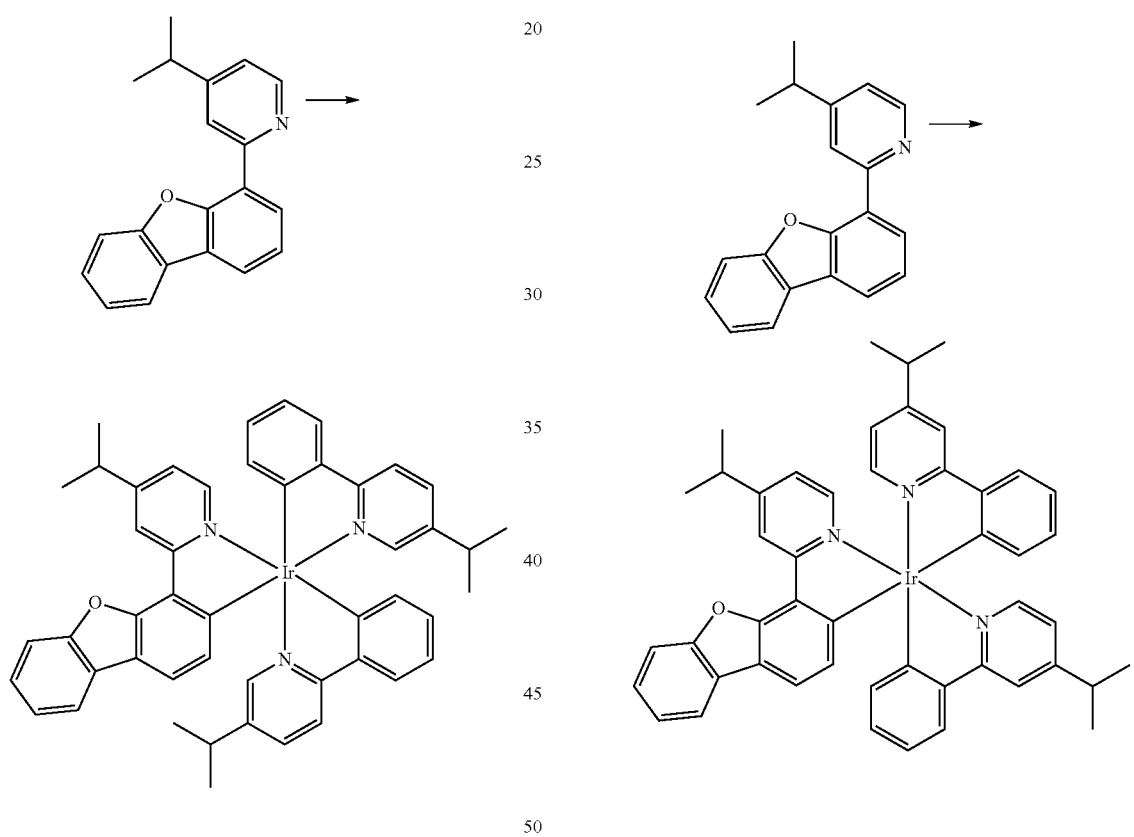

Synthesis of Compound 652

Synthesis of Compound 653

A mixture of the appropriate iridium trifluoromethanesulfonate complex (3.1 g, 3.9 mmol) and and 2-(dibenzo[b,d]furan-4-yl)-4-isopropylpyridine (3.1 g, 10.9 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with 1/1 (v/v) dichloromethane/hexane to yield 2.1 g (62%) of Compound 652 as a yellow solid. The product was confirmed by HPLC (99.9% pure) and LC/MS A mixture of iridium trifluoromethanesulfonate complex (2.4 g, 3.01 mmol) and 2-(dibenzo[b,d]furan-4-yl)4isopropylpyridine (3.0 g, 9.02 mmol) in EtOH (30 mL) and MeOH (30 mL) was refluxed for 20 h under nitrogen atmosphere. The reaction mixture was cooled to room temperature, diluted with ethanol, Celite® was added and the mixture stirred for 10 min. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with ⅔ (v/v) dichloromethane/hexane to yield 0.96 g (45%) of product as a yellow solid. The product was confirmed by HPLC (99.8% pure) and LC/MS.

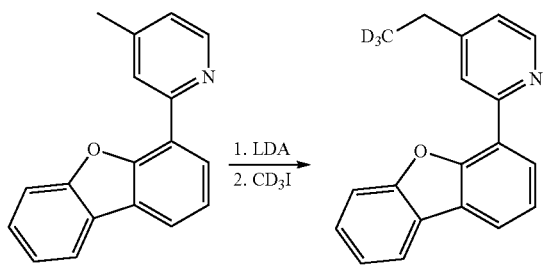 [SMILES: Cc1ccnc(-c2cccc3c2oc2ccccc23)c1 ; [2H]C([2H])([2H])Cc1ccnc(-c2cccc3c2oc2ccccc23)c1]

Synthesis of 2-(dibenzo[b,d]furan-4-yl)-4-ethyl-$d_3$-pyridine

To 2-(dibenzo[b,d]furan-4-yl)-4-methylpyridine (15.3 g, 59.0 mmol) in dry THF (250 mL) at −78° C. was added dropwise lithium diisopropylamide (35.4 mL, 70.8 mmol). The dark solution was stirred for 2 h at −78° C. and then $CD_3I$ was added (4.41 mL, 70.8 mmol) dropwise. The reaction mixture was allowed to slowly warm to RT overnight. Ammonium chloride solution and EtOAc were added and the reaction transferred separatory funnel. The layers were separated, washing the aqueous twice with EtOAc and combined organics once with water. After removal of the solvent, the crude product was chromatographed on silica gel with 8/2 (v/v) hexane/EtOAc and then 7/3 hexane/EtOAc to give 14.5 g of product as a pale yellow solid. Recrystallization from hexane gave 12.9 g (79%) of 2-(dibenzo[b,d]furan-4-yl)-4-ethyl-$d_3$-pyridine. HPLC purity: 99.4%.

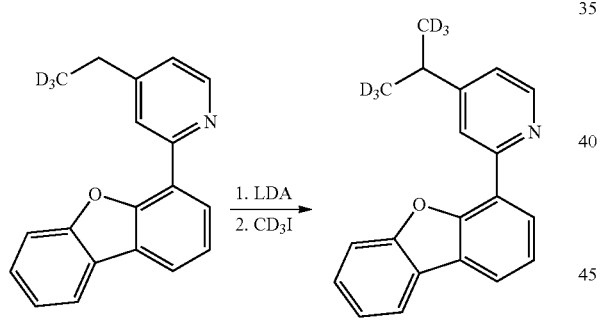

Synthesis of 2-(dibenzo[b,d]furan-4-yl)-4-isopropyl-$d_6$-pyridine 2-(Dibenzo[b,d]furan-4-yl)-4-ethyl-$d_3$-pyridine was dissolved in dry THF (100 mL) and cooled to −78° C. Lithium diisopropylamide (19.0 mL, 38.0 mmol) was added dropwise and the reaction mixture stirred for 2 h at −78° C. $CD_3I$ was added dropwise and the reaction mixture was allowed to slowly warm to room temperature overnight. The reaction was quenched with MeOH, $NH_4Cl$ (aq.) and EtOAc were added and the bipasic mixture transferred to a separatory funnel. The layers were separated, washing the aqueous layer twice with EtOAc and the combined organics with water. After removal of the solvent, the crude product was chromatographed on silica gel with 8/2 (v/v) hexane/EtOAc to give 6.4 g (86%) of 2-(dibenzo[b,d]furan-4-yl)-4-isopropyl-$d_6$-pyridine. HPLC purity: 99.2%.

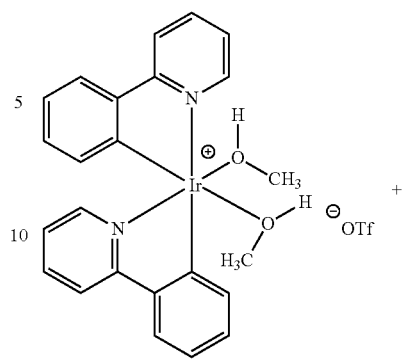

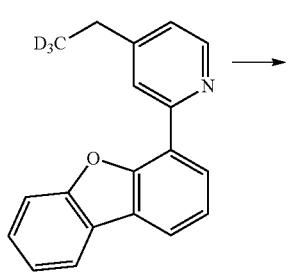

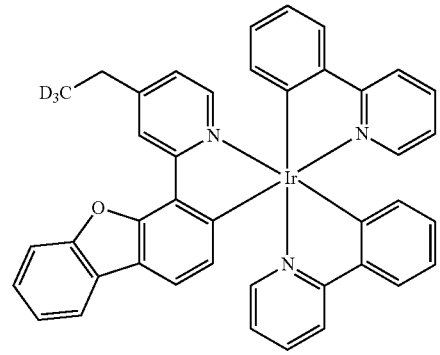

Synthesis of Compound 1145

A mixture of the appropriate iridium trifluoromethanesulfonate complex (3.5 g, 4.9 mmol) and 2-(dibenzo[b,d]furan-4-yl)-4-$d^3$-ethylylpyridine (3.5 g, 12.7 mmol) in EtOH (30 mL) and MeOH (30 mL) was refluxed for 20 h under inert atmosphere. The reaction mixture was cooled to room temperature, diluted with ethanol, celite was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with dichloromethane to yield 1.8 g (47%) of Compound 1145 as a yellow solid. The product was confirmed by HPLC (98.7% pure) and LC/MS.

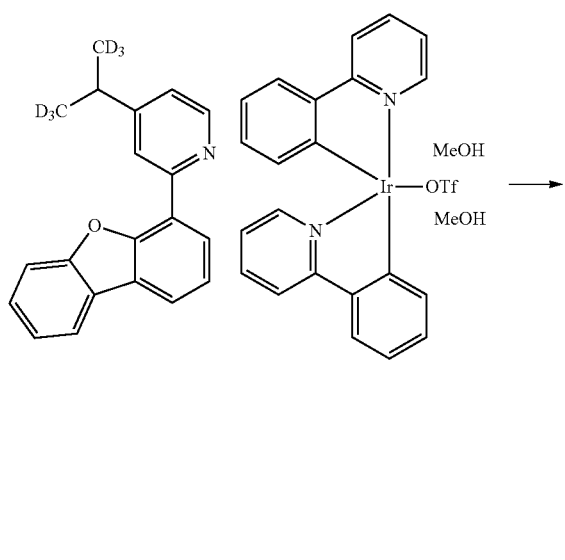

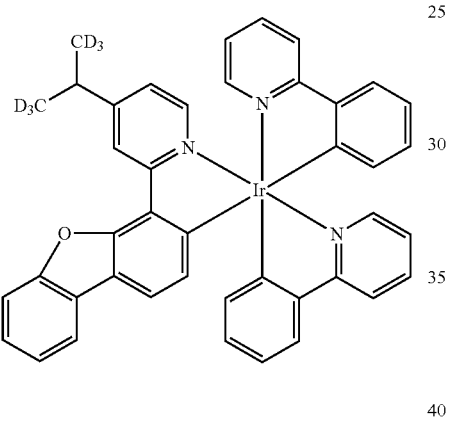

Synthesis of Compound 1146

2-(Dibenzo[b,d]furan-4-yl)-4-isopropyl-d$_6$-pyridine and the appropriate iridium trifluoromethanesulsonate complex were combined in ethanol (25 mL) and methanol (25 mL) and heated to reflux for 16 h. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The celite/silica plug was then washed with dichloromethane to dissolve the product. The crude product was chromatographed on silica gel with 50-70% dichloromethane in hexane to and then sublimed to yield 1.7 g (43%) of Compound 1146 as a yellow solid. The product was confirmed by HPLC (99.5% pure) and LC/MS.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having the formula:

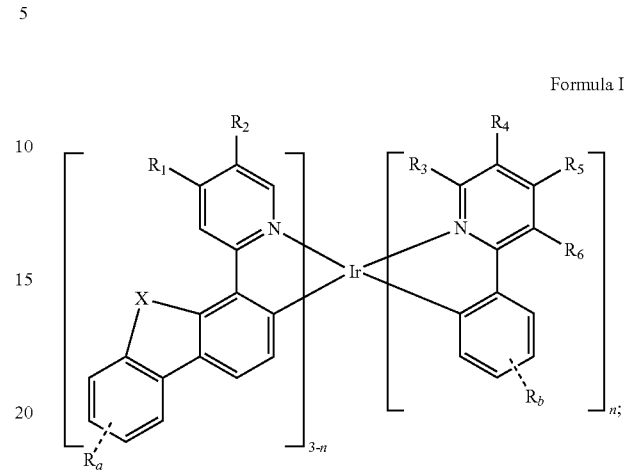

Formula I wherein the sum of the number of carbon atoms in R$_1$ is at least 2;

wherein R$_3$, R$_4$, R$_5$, R$_6$ are optionally linked;

wherein R$_a$ and R$_b$ represent mono-, di-, tri- or tetra-substitution;

wherein X is selected from the group consisting of BR, NR, PR, O, S, Se, C=O, S=O, SO$_2$, CRR', SiRR', and GeRR';

wherein R$_a$, R$_b$, R, R', R$_3$, R$_4$, R$_5$, and R$_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein n is 1 or 2, and wherein R$_1$ is alkyl or cycloalkyl, and R$_2$ is hydrogen or deuterium.

2. The compound of claim 1, wherein n is 2.

3. The compound of claim 1, wherein X is O.

4. The compound of claim 1, wherein R$_1$ is branched alkyl, cyclic alkyl, bicyclic alkyl, and multicyclic alkyl.

5. The compound of claim 1, wherein R$_1$ is iso-propyl.

6. The compound of claim 1, wherein R$_1$ or R$_2$ contains one or more deuterium atoms.

7. The compound of claim 1, wherein R$_1$ and R$_2$ contain one or more deuterium atoms.

8. The compound of claim 1, wherein R$_3$, R$_4$, R$_5$ and R$_6$ are independently selected from the group consisting of hydrogen, deuterium, alkyl, aryl, and combinations thereof.

9. The compound of claim 1, wherein at least one of R$_3$, R$_4$, R$_5$ and R$_6$ comprises a branched alkyl, cyclic alkyl, bicyclic alkyl, or a multicyclic alkyl.

10. The compound of claim 1, wherein R$_3$, R$_4$, R$_5$ or R$_6$ contain one or more deuterium atoms.

11. The compound of claim 1, wherein the compound is selected from the group consisting of:
Compound 625
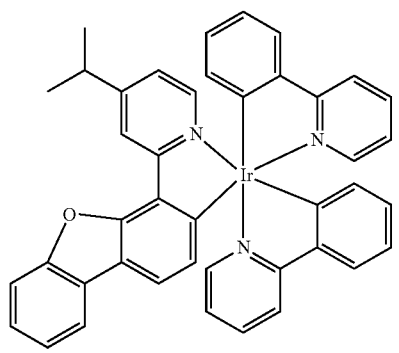
Compound 626
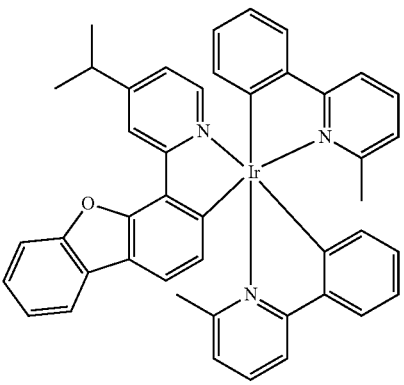
Compound 627
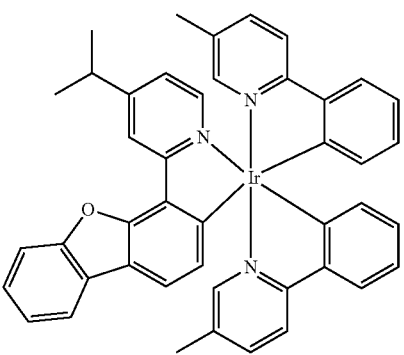
Compound 628
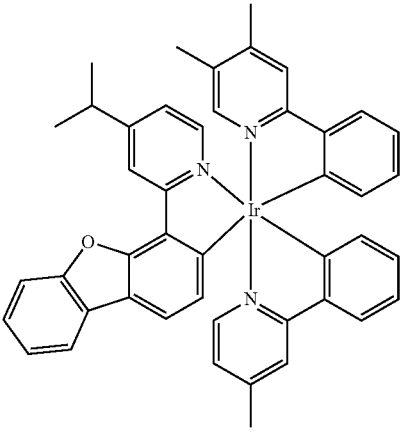
-continued
Compound 633
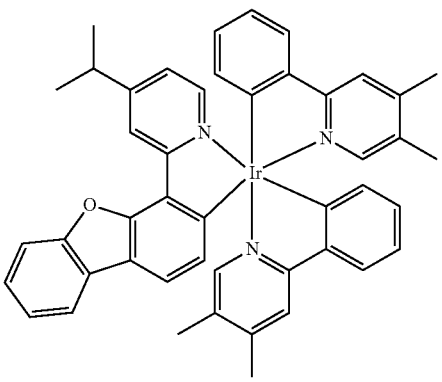
Compound 643
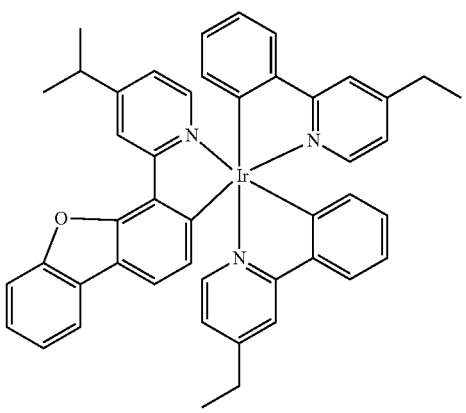
Compound 652
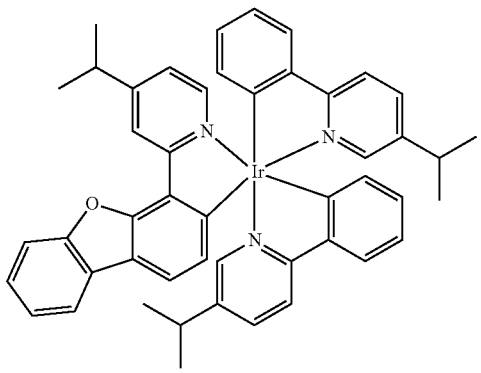
Compound 653

-continued

Compound 1145

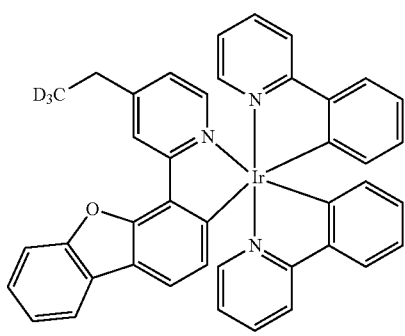

Compound 1146

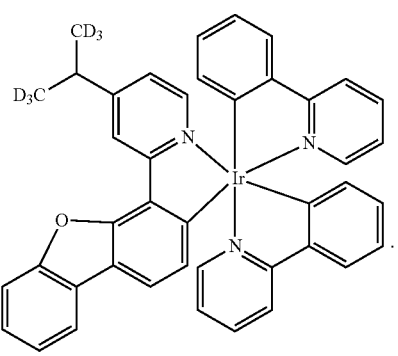

12. A first device comprising a first organic light emitting device, comprising:
an anode;
a cathode; and
an organic layer, disposed between the anode and the cathode, comprising a compound having the formula:

Formula I

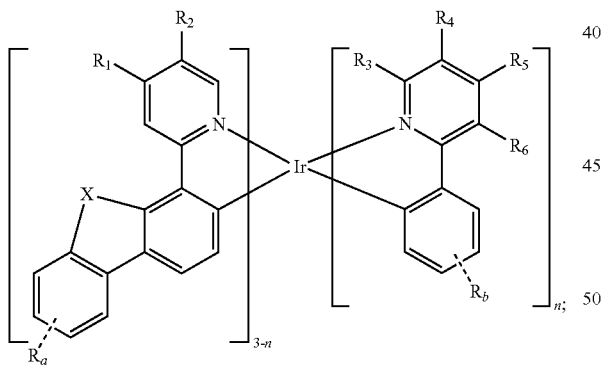

wherein the sum of the number of carbon atoms in $R_1$ is at least 2;
wherein $R_3$, $R_4$, $R_5$, $R_6$ are optionally linked;
wherein $R_a$ and $R_b$ represent mono-, di-, tri- or tetra-substitution;
wherein X is selected from the group consisting of BR, NR, PR, O, S, Se, C=O, S=O, $SO_2$, SiRR', and GeRR';
wherein $R_a$, $R_b$, R, R', $R_3$, $R_4$, $R_5$, and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein n is 1 or 2; and
wherein $R_1$ is alkyl or cycloalkyl, and $R_2$ is hydrogen or deuterium.

13. The first device of claim 12, wherein the first device is a consumer product.

14. The first device of claim 12, wherein the first device is an organic light-emitting device.

15. The first device of claim 12, wherein the first device comprises a lighting panel.

16. The first device of claim 12, wherein the organic layer is an emissive layer and the compound is an emissive dopant.

17. The first device of claim 12, wherein the organic layer is an emissive layer and the compound is a non-emissive dopant.

18. The first device of claim 12, wherein the organic layer further comprises a host.

19. The first device of claim 18, wherein the host comprises a triphenylene containing benzo-fused thiophene or benzo-fused furan;
wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2+1}$, $C\equiv CC_nH_{2n+1}$, $Ar_1$, $Ar_1$-$Ar_2$, and $C_nH_{2n}$-$Ar_1$;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.

20. The first device of claim 19, wherein the host has the formula:

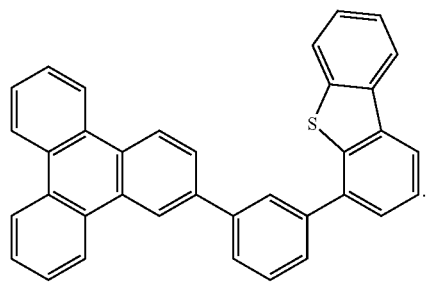 [SMILES: c1cc(-c2ccc3c4ccccc4c4ccccc4c3c2)cc(-c2cccc3c2sc2ccccc23)c1]

21. The first device of claim 18, wherein the host is selected from the group consisting of:

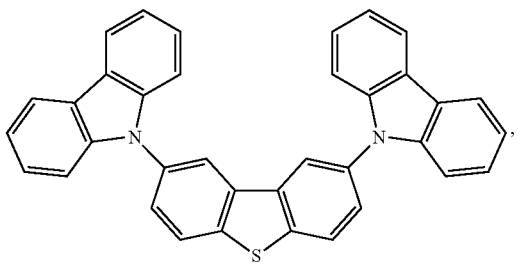

167
-continued
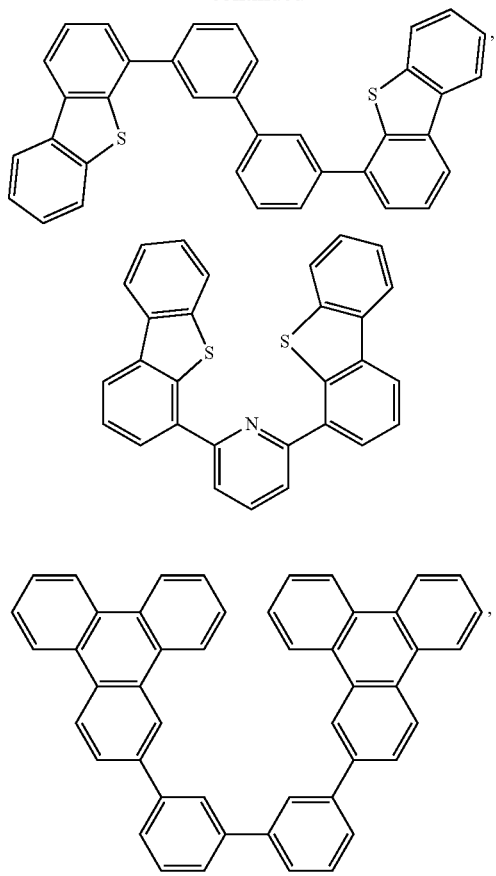
168
-continued
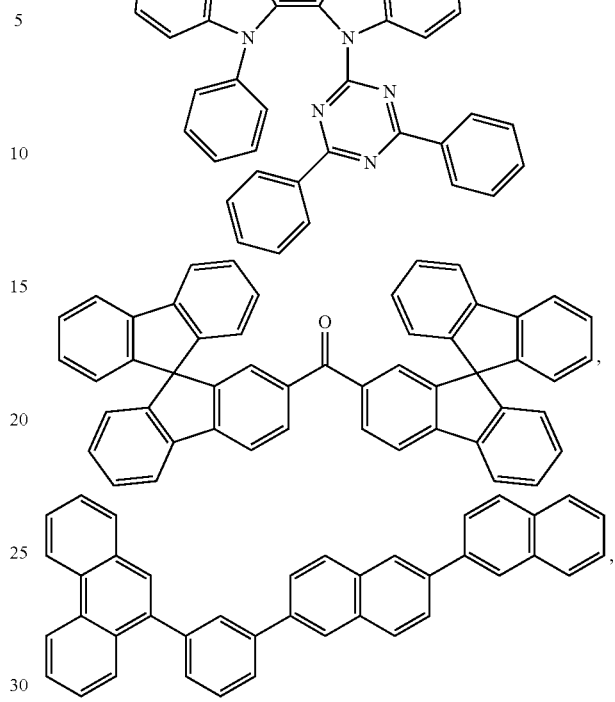
and combinations thereof.
22. The first device of claim 18, wherein the host is a metal complex.
* * * * *

UNITED STATES PATENT AND TRADEMARK OFFICE
CERTIFICATE OF CORRECTION

PATENT NO. : 9,184,397 B2  Page 1 of 1
APPLICATION NO. : 14/156808
DATED : November 10, 2015
INVENTOR(S) : Gregg Kottas et al.

It is certified that error appears in the above-identified patent and that said Letters Patent is hereby corrected as shown below:

In the Claims:

Claim 11, Column 163, Lines 49-65, delete

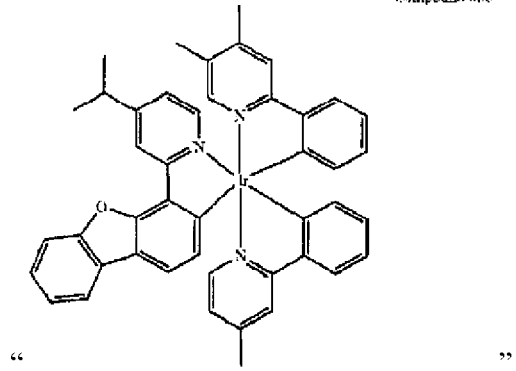

" "

and insert -- 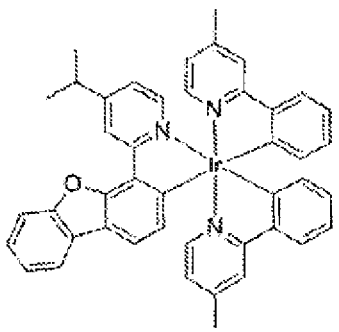 --

Signed and Sealed this
First Day of March, 2016

Michelle K. Lee
*Director of the United States Patent and Trademark Office*